(12) United States Patent
Zheng et al.

(10) Patent No.: US 10,039,729 B2
(45) Date of Patent: Aug. 7, 2018

(54) USE OF KUKOAMINE A AND KUKOAMINE B

(71) Applicants: Tianjin Chase Sun Pharmaceutical Co., Ltd., Tianjin (CN); The First Affiliated Hospital, Third Military Medical University, PLA, Chongqing (CN)

(72) Inventors: Jiang Zheng, Chongqing (CN); Xin Liu, Chongqing (CN); Xinchuan Zheng, Chongqing (CN); Hong Zhou, Chongqing (CN); Hongwei Cao, Chongqing (CN); Ning Wang, Chongqing (CN); Yongling Lu, Chongqing (CN)

(73) Assignees: Tianjin Chase Sun Pharmaceutical Co., Ltd, Tianjin (CN); The First Affiliated Hospital, Third Military Medical University, PLA, Shapingba District, Chongqing (CN)

( * ) Notice: Subject to any disclaimer, the term of this patent is extended or adjusted under 35 U.S.C. 154(b) by 25 days.

(21) Appl. No.: 15/379,626

(22) Filed: Dec. 15, 2016

(65) Prior Publication Data

US 2017/0189355 A1    Jul. 6, 2017

Related U.S. Application Data

(62) Division of application No. 13/638,966, filed as application No. PCT/CN2011/000478 on Mar. 21, 2011.

(30) Foreign Application Priority Data

Apr. 27, 2010 (CN) .......................... 2010 1 0156503

(51) Int. Cl.
 *A61K 31/165* (2006.01)
 *A61K 36/815* (2006.01)
(52) U.S. Cl.
 CPC .......... *A61K 31/165* (2013.01); *A61K 36/815* (2013.01)
(58) Field of Classification Search
 CPC ........................... A61K 31/165; A61K 36/815
 USPC ....................................................... 514/616
 See application file for complete search history.

(56) References Cited

U.S. PATENT DOCUMENTS

2005/0196478 A1* 9/2005 So ...................... A61K 36/815
 424/769
2013/0289112 A1 10/2013 Zheng et al.

OTHER PUBLICATIONS

Funayama et al. (Phytochemistry, (1995), vol. 38, pp. 1531.*
Funayama et al. (Tetrahedron Letters, (1980), vol. 21, pp. 1355-1356.*
Potterat. Planta Med (2010), vol. 76, pp. 7-19.*
Lui et al. Kukoamine B, a novel dual inhibitor of LPS and CpG DNA, is a potential candidate for sepsis treatment. (BJP (2011)) vol. 162, pp. 1274-1290.
Potterat. Planta Med Goji (Lycium barbarum and L. Chinense): Phytochemistry, Pharmacology, and Safety in the Perspective of Traditional Uses and Recent Popularity. 2010, vol. 76, pp. 7-19.
Hole's Human Anatomy and Physiology $10^{th}$ Edition (2004), Ed, Shiers et al. chapter 16, pp. 633.
Abreu et al. Innate immunity and Toll-Like Receptors: Clinical Implications of Basic Science Research. J Pediatr (2004), vol. 144, pp. 421-429).
Funayama et al. Kukoamine B, a spermine alkaloid from Lycium chinense. Phytochemistry (1995), vol. 38, pp. 1529-1531.
Funayama et al. Structure of Kukoamine A, A hypotensive Principle of Lycium Chinense Root Barks. Tetrahedron Lett. (1980), vol. 21, pp. 1355-1356.
Karigiannis et al. Simple Fragment Syntheses of All Four Isomers of the Spermine Alkaloid Kukoamine. Tetrahedron Letters (1998) vol. 39, pp. 5117-5120.

* cited by examiner

*Primary Examiner* — Melenie L McCormick
*Assistant Examiner* — Taina Del Mar Matos Negron
(74) *Attorney, Agent, or Firm* — Finnegan, Henderson Farabow, Garrett & Dunner, LLP

(57) ABSTRACT

The use of Kukoamine A and Kukoamine B in the preparation of drugs for the prevention and treatment of sepsis and autoimmune disease is disclosed. Bacterial endotoxin/lipopolysaccaride (LPS) and unmethylated DNA (CpG DNA) of bacteria, the major pathogen-associated molecular patterns in sepsis and autoimmune disease, are specifically targeted, while the disclosed use directionally isolates lead compounds from traditional Chinese medicine. These measures can overcome the major defects of uncertainty of pharmacological material basis and drug targets of extracts and constituents of traditional Chinese medicine. The disclosed use can help in developing a safe, effective and quality controllable drug for prevention and treatment of sepsis and autoimmune disease so as to help solve the present lack of effective drugs in clinical treatment.

5 Claims, 26 Drawing Sheets

Negative    KB 24 h

KB 48 h    KB 72 h

Liver

Negative    KB 24 h

KB 48 h    KB 72 h

Kidney

Cardiac muscle

USE OF KUKOAMINE A AND KUKOAMINE B

The present application is a divisional of U.S. patent application Ser. No. 13/638,966, filed Dec. 17, 2012, which is a national stage filing under 35 U.S.C. § 371 of International Application No. PCT/CN2011/000478, filed on Mar. 21, 2011, which claims priority of Chinese Patent Application No. 201010156503.X, filed Apr. 27, 2010. The contents of these applications are each incorporated herein by reference.

FIELD

The present invention relates to use of Kukoamine A and Kukoamine B in the preparation of drugs for the prevention and treatment of sepsis and autoimmune disease.

Sepsis and autoimmune disease are caused by body's excessive immune response, to which there were no reliable and effective drug strategies yet. Sepsis is an acute systemic inflammatory response syndrome, the mortality rate of which could be as high as 30%-70%, and it has been a serious threat to critically ill patients. According to incomplete statistics, over 3,000,000 people are diagnosed with sepsis every year in China, and more than half a million people died from it. Autoimmune disease is a chronic inflammation disease. As shown by epidemiological data, the incidence rate of autoimmune disease is about 3.2%-5.3% in China, and it has been one of the leading causes of death of women under 65. Therefore, appropriate prevention and treatment measures for sepsis and autoimmune disease have been a hot spot for clinical research.

At present, the treatment of sepsis and autoimmune disease is still very difficult, and empiric non-specific anti-inflammatory agents, such as glucocorticoids, are still the mainstay of treatment. However, these drugs not only rarely improve survival rates or survival quality of patients, but also may cause serious adverse reaction. In the past decades, the research of prevention and treatment of sepsis and autoimmune disease has been focused on inhibition of key molecules in immune response and correcting disorder of blood coagulation, complement, and etc. which are immediate cause of organ injury. Results of related studies show that it is not only difficult for these measures to achieve curative effect (immune response in vivo is a complicated network system which is difficult to regulate), these measures may also aggravate the disorder of immune system and cause further deterioration of pathogenetic condition. Accordingly, related studies have not got any breakthrough so far, and there are no reliable and effective new drugs entering clinical trails. All these facts indicate that we need to understand the nature of pathogenesis and trigger of sepsis and autoimmune disease, and look for specific curative drugs.

In recent years, impressive progress has been made in pathogenesis of sepsis and autoimmune disease. At present in addition to influence of endocrine, genetic and environmental factors, bacterial endotoxin/lipopolysaccharide (LPS) and unmethylated DNA (CpG DNA) of bacteria are considered as trigger factors which start an attack of sepsis and autoimmune disease. Many studies have confirmed that LPS and CpG DNA could induce sepsis together or separately, and they could also induce or aggravate symptoms of rheumatoid arthritis. In the course of acute infection, rapid invasion of pathogens may generate large amount of LPS and CpG DNA, which induce large number of expression and release of various inflammatory mediators, such as TNF-α, IL-1β, IL-6 etc., within a short period of time, leading to early organ dysfunction and late immune paralysis, and resulting in death of sepsis patients. For autoimmune disease, the persistence of LPS and CpG DNA may lead to persistence and chronic evolution of inflammatory reaction, and induce mass production of inflammatory mediators, immunoglobulins and rheumatoid factor etc., which form immune complex depositing on synovium, activate complement, product anaphylatoxin, resulting in inflammatory pathologic damage, and eventually leading to organ injury. Thus it can be seen that effective antagonism on LPS and CpG DNA could prevent and cure sepsis and autoimmune disease from the source. Related drug researches have confirmed that the blockade of irritant reaction of LPS and CpG DNA to immunocyte and the inhibition of release of inflammatory mediators, like TNF-α, have obvious therapeutic effects on sepsis and autoimmune disease. Therefore, antagonistic activity on LPS and CpG DNA could reflect preventive and therapeutic effects of certain drugs to sepsis and autoimmune disease.

Traditional Chinese herbs for clearing away the heat-evil and expelling superficial evils have long been used in immune system disorder, such as sepsis and autoimmune disease, and have a good curative effect in the clinical practice. Modern pharmacological studies have shown that there are certain compositions existed in traditional Chinese herbs, which could bind and antagonize the pathogen-associated molecular patterns, e.g. LPS and CpG DNA, and serve as important material basis in correcting immunologic derangement, preventing and curing sepsis and autoimmune disease. Da Chengqi decoction, Reduqing, Reduping and other agents can reduce levels of LPS, TNF-α, IL-1 and IL-6 in circulating blood of sepsis patients; *Lonicera japonica* Thunb., *Forsythia suspensa* (Thunb.) Vahl, *Scutellaria baicalensis* Georgi, *Artemisia annua* L. and other more than 20 kinds of Chinese herbal medicines have good antagonistic activity on pathogen-associated molecular patterns, e.g. LPS, in vitro experiments; decoction of *Atractylodis macrocephalae* rhizome can significantly reduce the elevated levels of LPS and TNF-α in serum of patients with rheumatoid arthritis, suppress the levels of IgG, IgA and IgM in serum, reduce RF (rheumatoid factor) positive rate, and thus achieve treatment of rheumatoid arthritis; Langchuang formula, which consists of 7 kinds of Chinese herbal medicines for heat-clearing and detoxicating, such as *Oldenlandia diffusa* (Willd.) Roxb., *Scutefiaria barbata* D. Don, *Arnebia enchroma* (Royle) Johnst., *Salvia miltiorrhiza* Bge., *Leonurus japonicus* Houtt. etc., can inhibit the activation of T cell and B cell, reduce the generation of IL-6, IL-10 and autoantibody, and play a role in the treatment of systemic lupus erythematosus. However, the complicated constituents and uncertainty of drug safety, to a significant degree, limit the use of traditional Chinese herbs in clinical treatment. Therefore, separation of monomer, which can antagonize LPS and CpG DNA, is of great significance in prevention and treatment of sepsis and autoimmune disease.

*Lycii cortex* is the dried root bark of *Lycium chinense* Mill, or *Lycium barbarum* L of the Solanaceae family. In traditional Chinese medicine theory, it has the effects of clearing away the heat-evil and expelling superficial evils. Modern pharmacological studies have found that *Lycii cortex* contains alkaloids, organic acids, anthraquinones and peptides, and it plays a pharmacological role of anti-hypertension, anti-hyperglycemia, relieving fever and analgesia. However, researches and applications on *Lycii cortex* antagonizing LPS and CpG DNA and treating sepsis and autoimmune disease have not been reported in domestic and foreign literatures and domestic invention patents up to now.

SUMMARY OF THE INVENTION

The purpose of present invention is to overcome the major defect of uncertainty of material basis and mechanisms of constituents and extractives in traditional Chinese medicine, develop a safe, effective, quality controllable drug for prevention and treatment of sepsis and autoimmune disease, and solve the lack of effective drugs in clinical treatment at present.

The technical solution of present invention is:

The invention relates to the use of Kukoamine A and Kukoamine B in the preparation of drugs for the prevention and treatment of bacterial sepsis and autoimmune disease.

Said Kukoamine A and Kukoamine B are extracted from *Lycii cortex* in traditional Chinese medicine.

Said drug is used for treatment of sepsis and autoimmune disease.

Said drug is used for antagonizing the key factors, e. g bacterial endotoxin/lipopolysaccharide (LPS) and unmethylated DNA of bacteria, which induce the development of sepsis and autoimmune disease.

Said *Lycii cortex* is the dried root bark of *Lycium chinense* Mill, or *Lycium barbarum* L. of the Solanaceae family.

methods of macroporous adsorptive resins, cation exchange and reversed-phase high-performance liquid chromatography; through pharmacological evaluation in vivo and in vitro, such as experiments of neutralization of LPS in vitro, experiments of inhibition on bindings of LPS and CpG DNA with cells, experiments of inhibition on inflammatory reaction caused by stimulations of LPS and CpG DNA, and experiments of protection of model animal with sepsis, eventually, two active constituents, Kukoamine A (KA) and Kukoamine B (KB), which have good antagonistic effect on LPS and CpG DNA, were screened out.

By means of activity tracking, the present invention separates active constituents antagonizing LPS and CpG DNA from traditional Chinese herbs, and provides safe, reliable and effective drugs for prevention and treatment of sepsis and autoimmune disease.

Said Kukoamine A and Kukoamine B are spermine-like alkaloids extracted from *Lycii cortex*. They are a pair of isomeride, with the same molecular formula of $C_{28}H_{42}N_4O_6$ and molecular weight of 530.66. Their

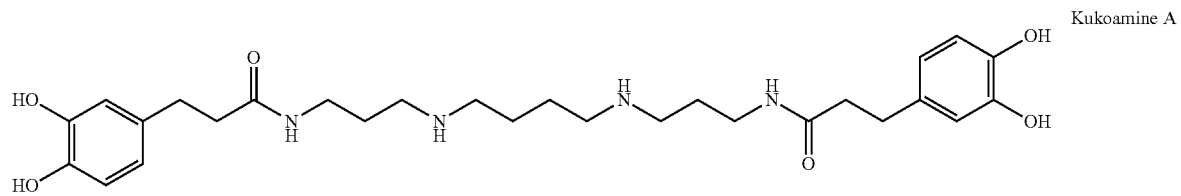 [SMILES: O=C(CCc1ccc(O)c(O)c1)NCCCNCCCCNCCCNC(=O)CCc1ccc(O)c(O)c1]

Kukoamine A chemical structures are respectively as follows:

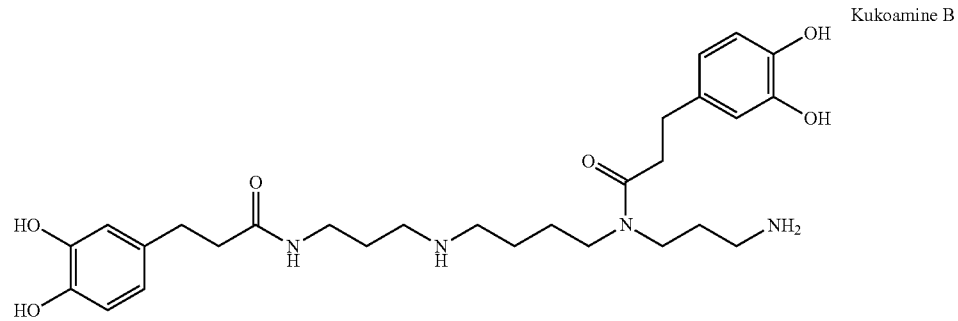 [SMILES: NCCCN(CCCCNCCCNC(=O)CCc1ccc(O)c(O)c1)C(=O)CCc1ccc(O)c(O)c1]

Kukoamine B

The applicant persists for a long time in drug research of antagonizing pathogen-associated molecular patterns targeting at LPS and CpG DNA. Through biosensor screening and tracking platform established, the applicant screens and directionally isolates the activated monomer, which has effects of binding and antagonizing LPS and CpG DNA, from traditional Chinese medicine for clearing away the heat-evil and expelling superficial evils.

The present invention uses *Lycii cortex* as raw material, establishes drug screening and directional separating platform targeting at lipid A and CpG DNA, and uses binding activity of Chinese herb extracts with lipid A and CpG DNA as screening indicators. Raw material was boiled with water; then, it was extracted, isolated and purified respectively with Kukoamine A and Kukoamine B of the present invention have a brilliant prospect of being effective drugs in treatment of sepsis and autoimmune disease. Specifically experiments in vitro demonstrated that Kukoamine A and Kukoamine B have high affinity with LPS and CpG DNA, can significantly neutralize LPS and CpG DNA, blockade their bindings with RAW264.7 cells (murine macrophages), inhibit the expression and release of inflammatory mediators (TNF-α, IL-6, etc.) in RAW264.7 cells induced by LPS and CpG DNA, and finally blockade the inflammatory activation of cells and prevent disorders of the immune response. It has been observed in vivo experiments that Kukoamine A and Kukoamine B can lower the levels of LPS and TNF-α in mice injected with heat-killed *Escherichia coli* (mimic vivo injection of LPS and CpG DNA), play a role in antagonism on LPS and CpG DNA, and improve survival rates of the mice.

DESCRIPTION OF THE DRAWINGS

FIG. 1a is a response curve of immobilization of lipid A. FIG. 1b is a response curve of immobilization of CpG DNA. FIG. 1c shows binding reaction of lipid A with *Lycii cortex* and other 6 kinds of traditional Chinese medicine. FIG. 1d shows binding reaction of CpG DNA with *Lycii cortex* and other 6 kinds of traditional Chinese medicine. The reference number in FIG. 1c and FIG. 1d separately denotes: 1. *Lycii cortex*; 2. *Paeonia suffruticosa* Andr; 3. *Cornus officinalis* Sieb. et Zucc.; 4. *Rheum palmatum* L.; 5. *Scutellaria baicalensis* Georgi; 6. *Cinnamomum cassia* Presl.

FIG. 2a is the chromatogram of constituents separation of CL-1~5. FIG. 2b shows binding reaction of CL-1~5 constituents with lipid A. FIG. 2c shows binding reaction of CL-1~5 constituents with CpG DNA.

FIG. 3a is chromatogram of constituents separation of CL-4a, -4b and -4c. FIG. 3b shows binding reaction of CL-4 constituents with lipid A. FIG. 3c shows binding reaction of CL-4 constituents with CpG DNA.

FIG. 5a shows the inhibition of CL-4b constituents on the release of TNF-α and IL-6 in RAW264.7 cells induced by LPS. FIG. 5b shows the inhibition of CL-4b constituents on the release of TNF-α and IL-6 in RAW264.7 cells induced by CpG DNA (CPG). In FIGS. 5a and 5b, the symbol * means $p<0.05$, and ** means $p<0.01$ vs LPS or CpG DNA (CpG).

FIG. 7a is a HPLC diagram of CL-4b$_1$ constituents. FIG. 7b is a HPLC diagram of CL-4b$_2$ constituents.

FIG. 8a shows the affinity detection of KA and KB with lipid A. FIG. 8b shows the affinity detection of KA and KB with CpG DNA.

FIG. 10a shows the inhibition of KA and KB on the binding of fluorescently-labeled LPS with RAW264.7 cells. FIG. 10b shows the inhibition of KA and KB on the binding of fluorescently-labeled CpG DNA (CpG) with RAW264.7 cells, and the symbol ** in FIGS. 10a and 10b means $p<0.01$ vs FITC-LPS or 5-FAM-CpG DNA.

FIG. 11a shows the inhibition of KA and KB on the release of TNF-α in RAW264.7 cells induced by LPS. FIG. 11b shows the inhibition of KA and KB on the release of TNF-α in RAW264.7 cells induced by CpG DNA. In FIG. 11a and 11b, the symbol * means $p<0.05$, and ** means $p<0.01$ vs LPS or CpG DNA.

FIG. 13a shows the influence of KA and KB on LPS level in blood of mice challenged by *E. coli*. FIG. 13b shows the influence of KA and KB on TNF-α level in blood of mice challenged by *E. coli*. In FIGS. 13a and 13b, the symbol * means $p<0.05$, and ** means $p<0.01$ vs *E. coli*.

FIG. 14a shows the affinity detection of KB and PMB with LPS. FIG. 14b shows the affinity detection of KB and PMB with CpG DNA.

FIG. 16a shows the inhibition of KB on the release of TNF-α in RAW264.7 cells stimulated by LPS and CpG DNA (CPG). FIG. 16b shows the inhibition of KB on the release of IL-6 in RAW264.7 cells stimulated by LPS and CpG DNA (CPG). In FIGS. 16a and 16b, the symbol ** means $p<0.01$ vs LPS, and ## means $p<0.01$ vs CpG DNA.

FIG. 17a shows the inhibition of KB and PMB on the release of TNF-α in RAW264.7 cells stimulated by LPS. FIG. 17b shows the inhibition of KB and PMB on the release of TNF-α in RAW264.7 cells stimulated by CpG DNA (CPG). FIG. 17c shows the inhibition of KB and PMB on the release of IL-6 in RAW264.7 cells stimulated by LPS. FIG. 17d shows the inhibition of KB and PMB on the release of IL-6 in RAW264.7 cells stimulated by CpG DNA (CPG). In FIGS. 17a, 17b, 17c and 17d, the symbol * means $p<0.05$, and ** means $p<0.01$ vs LPS or CpG DNA.

FIG. 18a shows the inhibition of KB and PMB on the release of TNF-α in murine peritoneal macrophages stimulated by LPS. FIG. 18b shows the inhibition of KB and PMB on the release of TNF-α in murine peritoneal macrophages stimulated by CpG DNA (CPG). FIG. 18c shows the inhibition of KB and PMB on the release of IL-6 in murine peritoneal macrophages stimulated by LPS. FIG. 18d shows the inhibition of KB and PMB on the release of IL-6 in murine peritoneal macrophages stimulated by CpG DNA (CPG). In FIGS. 18a, 18b, 18c and 18d, the symbol * means $p<0.05$, and ** means $p<0.01$ vs LPS or CpG DNA.

FIG. 19a shows the inhibition of KB on the mRNA expression of TNF-α in RAW264.7 cells stimulated by LPS and CpG DNA (CPG). FIG. 19b shows the inhibition of KB on the mRNA expression of IL-6 in RAW264.7 cells stimulated by LPS and CpG DNA (CPG). FIG. 19c shows the inhibition of KB on the mRNA expression of iNOS in RAW264.7 cells stimulated by LPS and CpG DNA (CPG). FIG. 19d shows the inhibition of KB on the mRNA expression of COX-2 in RAW264.7 cells stimulated by LPS and CpG DNA (CPG). In FIGS. 19a, 19b, 19c and 19d, the symbol * means p<0.05, and ** means p<0.01 vs LPS or CpG DNA.

FIG. 20a shows the inhibition of KB on the mRNA expression of TNF-α in murine peritoneal macrophages stimulated by LPS and CpG DNA (CPG). FIG. 20b shows the inhibition of KB on the mRNA expression of IL-6 in murine peritoneal macrophages stimulated by LPS and CpG DNA (CPG). In FIGS. 20a and 20b, the symbol * means p<0.05, and ** means p<0.01 vs LPS or CpG DNA.

FIG. 21a shows the dose-dependent effects of KB antagonism on LPS and CpG DNA (CPG). FIG. 21b shows the time-dependent effects of inhibition of KB on TNF-α release in RAW264.7 cells induced by LPS. FIG. 21c shows the time-dependent effects of inhibition of KB on TNF-α release in RAW264.7 cells induced by CpG DNA (CPG). In FIG. 21a the symbol * means p<0.05, and ** means p<0.01 vs LPS or CpG DNA.

FIG. 22a shows the inhibition of KB on TNF-α release in RAW264.7 cells induced by LPS and CpG DNA (CPG), in which KB was loaded after preincubation with LPS or CpG DNA (CPG). FIG. 22b shows the inhibition of KB on TNF-α release in RAW264.7 cells induced by LPS and CpG DNA (CPG), in which KB was loaded at various time points. FIG. 22c shows the inhibition of KB on TNF-α release in RAW264.7 cells induced by LPS and CpG DNA (CPG), in which KB was loaded under serum-free conditions. In FIG. 22c, the symbol * means p<0.05 and ** means p<0.01 vs LPS or CpG DNA.

FIG. 23a shows the inhibition of KB on TNF-α release in RAW264.7 cells induced by various pathogen-associated molecular patterns. FIG. 23b shows the inhibition of KB on IL-6 release in RAW264.7 cells induced by various pathogen-associated molecular patterns.

FIG. 24a shows the influence of KB on mean fluorescence intensity of LPS on RAW264.7 cell surface. FIG. 24b shows the influence of KB on mean fluorescence intensity of CpG DNA (CPG) on RAW264.7 cell surface. In FIGS. 24a and 24b, the symbol * means p<0.05, and ** means p<0.01 vs FITC-LPS or 5-FAM-CpG DNA.

FIG. 25a shows the KB influence on binding and cellular internalization of LPS to RAW264.7 cells. FIG. 25b shows the KB influence on mean fluorescence intensity of 5-FAM-CpG DNA on RAW264.7 cell surface.

FIG. 26a shows the inhibition of KB on the up-regulated expression of TLR4 mRNA induced by LPS and CpG DNA (CPG). FIG. 26b shows the inhibition of KB on the up-regulated expression of TLR9 mRNA induced by LPS and CpG DNA (CPG). The symbol ** in FIGS. 26a and 26b means p<0.01 vs LPS or CpG DNA.

FIG. 27a shows the degradation of $I_\kappa B$-α in RAW264.7 cells after stimulated by LPS, CpG DNA (CPG), TNF-α and IL-1β for different time (15, 30, 45, and 60 mins). FIG. 27b shows the inhibition of KB on up-regulated phosphorylation of signaling molecules p38 induced by LPS, CpG DNA (CPG), TNF-α and IL-1β, and the inhibition of KB on degradation and phosphorylation of $I_\kappa B$-α, in RAW264.7 cells.

FIG. 28a shows the inhibition of KB on up-regulation of NF-kB p65 subunit in RAW264.7 cell nucleus induced by LPS and CpG DNA (CPG). FIG. 28b shows assay of KB inhibition on NF-kB activation in RAW264.7 cells induced by LPS and CpG DNA (CPG) using a luciferase reporter gene assay. The symbol ** in FIGS. 28a and 28b means p<0.01 vs LPS or CpG DNA.

FIG. 29a shows KB inhibition on up-regulated expression of TLR4 and TLR9 mRNA in RAW264.7 cells induced by LPS and CpG DNA (CPG). FIG. 29b shows KB inhibition on up-regulated expression of MyD88 mRNA in RAW264.7 cells induced by LPS and CpG DNA (CPG). FIG. 29c shows KB inhibition on activation of NF-kB in RAW264.7 cells induced by LPS and CpG DNA (CPG).

FIG. 30a shows the influence of KB on vitality of RAW264.7 cells. FIG. 30b shows the influence of the combination of KB with LPS or CpG DNA (CPG) on vitality of RAW264.7 cells. FIG. 30c shows the influence of KB on vitality of murine peritoneal macrophages. FIG. 30d shows the influence of the combination of KB with LPS or CpG DNA (CPG) on vitality of murine peritoneal macrophages.

FIG. 31a shows the protection of single dose of KB (30 mg/kg) on mice challenged by lethal dose of heat-killed *Escherichia coli*. FIG. 31b shows the protection of single dose of KB (15, 30 and 60 mg/kg) on mice challenged by lethal dose of heat-killed *Escherichia coli*. FIG. 31c shows the protection of multiple dosing of KB (1.25, 2.5 and 5 mg/kg) on mice challenged by lethal dose of heat-killed *Escherichia coli*. In FIGS. 31a, 31b and 31c, the symbol * means p<0.05, and ** means p<0.01 vs *E. coli*. (EC).

FIG. 32a shows the influence of KB on LPS levels in plasma of mice challenged by sublethal dose of heat-killed

*Escherichia coli.* FIG. 32*b* shows the influence of KB on TNF-α levels in serum of mice challenged by sublethal dose of heat-killed *Escherichia coli.* In FIGS. 32*a* and 32*b*, the symbol * means p<0.05, and ** means p<0.01 vs *E. coli.* (EC).

* In FIG. 33, the symbol * means p<0.05, and ** means p<0.01 vs *E. coli.* (EC).

FIG. 34*a* shows the lung morphology of mice after KB injection. FIG. 34*b* shows the liver morphology of mice after KB injection. FIG. 34*c* shows the kidney morphology of mice after KB injection. FIG. 34*d* shows the cardiac muscle morphology of mice after KB injection.

DETAILED DESCRIPTION

Figure 1A:
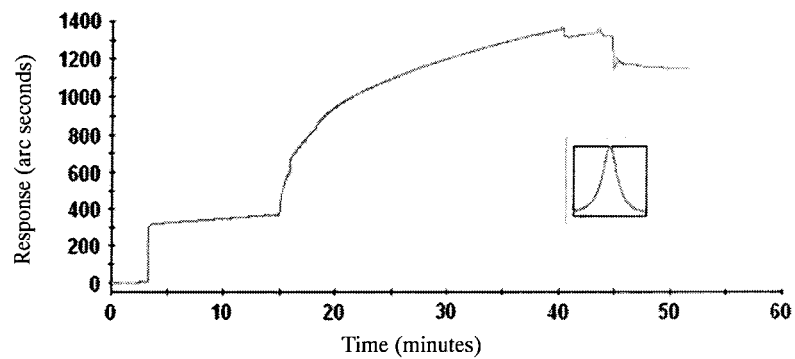
FIG. 1a, 1b, 1c and 1d show the response curve of immobilization of lipid A and CpG DNA, and the binding curve of 6 kinds of traditional Chinese medicine decoction with lipid A and CpG DNA.

Because LPS and CpG DNA are key factors inducing sepsis and autoimmune disease, antagonistic activity on LPS and CpG DNA can reflect preventive and therapeutic effects of certain drugs to sepsis and autoimmune disease. The research models selected in the detailed description are all used to evaluate the binding and antagonistic activity of KA and KB on LPS and CpG DNA, and to reflect treatment effect of KA and KB to sepsis and autoimmune disease. The present invention will be further described through following embodiments. It should be pointed out that the following embodiments are intended to illustrate rather than limit the disclosure.

The source of traditional Chinese herbs, reagent and materials in the detailed description 1. The source of 114 kinds of traditional Chinese herbs: name and origin, see Table 1

TABLE 1

Name and origin of 114 kinds of traditional Chinese herbs

| Latin name | Origin | Latin name | Origin | Latin name | Origin |
|---|---|---|---|---|---|
| *Holboellia latifolia* Wall. | Sichuan Province | *Cinnamomum cassia* Presl | Guangxi Province | *Fraxinus rhynchophylla* Hance | Sichuan Province |
| *Patrinia scabiosaefolia* Fisch. | Sichuan Province | *Piper kadsura* (Choisy) Ohwi | Zhejiang Province | *Gentiana macrophylla* Pall. | Gansu Province |
| *Lobelia chinensis* Lour. | Sichuan Province | *Nelumbo nucifera* Gaertn. | Sichuan Province | *Artemisia annua* L. | Hubei Province |
| *Scutellaria barbata* D. Don | Sichuan Province | *Phellodendron chinense* Schneid. | Sichuan Province | *Senecio scandens* Buch.-Ham. | Sichuan Province |
| *Isatis indigotica* Fort. (Isatidis Radix) | Anhui Province | *Coptis chinensis* Franch. | Sichuan Province | *Polygonum bistorta* L. | Sichuan Province |
| *Heterosmilax japonica* Kunth | Sichuan Province | *Scutellaria baicalensis* Georgi | Sichuan Province | *Cinnamomum cassia* Presl | Guangxi Province |
| *Bletilla striata* (Thunb.) Reichb.f. | Sichuan Province | *Dioscorea bulbifera* L. | Hubei Province | *Sophora tonkinensis* Gagnep. | Sichuan Province |
| *Pulsatilla chinensis* (Bge.) Regel | Jiangxi Province | *Sargentodoxa cuneata* (Oliv.) Rehd et Wils. | Sichuan Province | *Cornus officinalis* Sieb. et Zucc. | Guangxi Province |
| *Oldenlandia diffusa* (Willd.) Roxb. | Jiangxi Province | *Saxifraga stolonifera* Curt. | Sichuan Province | *Crataegus pinnatifida* Bge. var. major N. E. Br. | Hebei Province |
| *Dictamnus dasycarpus* Turcz. | Liaoning Province | *Sophora japonica* L. (Sophorae flos) | Sichuan Province | *Cremastra appendiculata* (D. Don) Makino | Sichuan Province |
| *Ampelopsis japonica* (Thunb.) Makino | Sichuan Province | *Sophora japonica* L. (Sophorae fructus) | Henan Province | *Phytolacca acinosa* Roxb. | Sichuan Province |
| *Cynanchum atratum* Bge. | Anhui Province | *Cannabis sativa* L. | Sichuan Province | *Cnidium monnieri* (L.) Cuss. | Guangdong Province |
| *Mentha haplocalyx* Briq. | Zhejiang Province | *Playtycodon grandiflorum* (Jacq.) A.DC. | Hebei Province | *cimmicifuga heracleifolia* Kom. | Sichuan Province |
| *Buplerum chinense* DC. | Sichuan Province | *Schizonepeta tenuifolia* Briq. | Sichuan Province | *Punica granatum* L. | Sichuan Province |
| *Amomum tsao-ko* Crevost et Lemarie | Guandong Province | *Fagopyrum dibotrys* (D.Don) Hara | Sichuan Province | *Prunus persica* (L.) Batsch | Sichuan Province |

TABLE 1-continued

Name and origin of 114 kinds of traditional Chinese herbs

| Latin name | Origin | Latin name | Origin | Latin name | Origin |
| --- | --- | --- | --- | --- | --- |
| *Dichroa febrifuga* Lour. | Sichuan Province | *Lonicere japonica* Thunb. | Sichuan Province | *Asparagus cochinchinensis* (Lour.) Merr. | Henan Province |
| *Platycladus orientalis* (L.) Franco | Sichuan Province | *Tinospora sagittata* (Oliv.) Gagnep. | Sichuan Province | *Trichosanthes kirilowii* Maxim. | Hunan Province |
| *Artemisia argyi* Lévl. et Vant. | Sichuan Province | *Cassia obtusifolia* L. | Hubei Province | *Semiaquilegia adoxoides* (DC.) Makino | Sichuan Province |
| *Fritillaria cirrhosa* D. Don | Sichuan Province | *Chrysanthemun morifolium* Ramat. | Zhejiang Province | *Clematis chinensis* Osbeck | Sichuan Province |
| *Iris tectorum* Maxim. | Hubei Province | *Aspongopus chinensis* Dallas | Sichuan Province | *Prunus mume* (Sieb.) Sieb. et Zucc. | Sichuan Province |
| *Andrographis paniculata* (Burm.f.) Nees | Guangdong Province | *Sophora flavescens* Ait. | Sichuan Province | *Scrophularia ningpoensis* Hemsl. | Sichuan Province |
| *Sdeum sarmentosum* Bunge | Sichuan Province | *Tripterygium wilfordii* Hook.f. | Sichuan Province | *Terminalia chebula* Retz. (Purchased from Guangdong Province) | Guangdong Province |
| *Paeonia lactiflora* Pall. | Inner Mongolia | *Nelumbo nucifera* Gaertn. | Sichuan Province | *Prunella vulgaris* L. | Sichuan Province |
| *Isatis indigotica* Fort. (Isatidis folium) | Anhui Province | *Forsythia suspensa* (Thunb.) Vahl | Henan Province | *Asarum heterotropoides* Fr. Schmidt var. *mandshuricum* (Maxim). Kitag. | Liaoning Province |
| *Rheum palmatum* L. | Sichuan Province | *Gentiana manshurica* Kitag. | Jilin Province | *Commelina communis* L. | Sichuan Province |
| *Salvia Miltiorrhiza* Bge. | Gansu Province | *Solanum nigrum* L. | Sichuan Province | *Brucea javanica* (L.) Merr. | Sichuan Province |
| *Hypericum japonicum* Thumb. | Sichuan Province | *Rhaponticum uniflorum* (L.) DC. | Sichuan Province | *Chrysanthemum indicum* L. | Sichuan Province |
| *Kochia scoparia* (L.) Schrad. | Sichuan Province | *Phragmites communis* Trin. | Sichuan Province | *Houttuynia cordata* Thunb. | Sichuan Province |
| *Lycii Cortex* | Gansu Province | *Lasiophaera fenzlii* Reich. | Inner Mongolia | *Stellaria dichotoma* L. var. *lanceolata* Bge. | Inner Mongolia |
| *Sanguisorba officinalis* L. | Jiangsu Province | *Portulaca oleracea* L. | Sichuan Province | *Artemisia capillaris* Thunb. | Shaanxi Province |
| *Eugenia caryophyllata* Thunb. | Yunnan Province | *Verbena officinalis* L. | Sichuan Province | *Amebia enchroma* (Royle) Johnst. | Liaoning Province |
| *Cassia angustifolia* Vahl | Sichuan Province | *Ilex pubescens* Hook.et Arn. | Sichuan Province | *Viola yedoensis* Makino | Sichuan Province |
| *Stephania tetrandra* S. Moore | Guangdong Province | *Paeonia suffruticosa* Andr. | Henan Province | *Citrus aurantium* L. | Sichuan Province |
| *Poria cocos* (Schw.) Wolf | Hubei Province | *Folium Hibisci Mutabilis* | Sichuan Province | *Terminalia chebula* Retz. (Purchased from Yunnan Province) | Yunnan Province |
| *Aconitum carmichaelii* Debx. | Sichuan Province | *Equisetum hiemale* L. | Shaanxi Province | *Paris polyphylla* Sm. | Sichuan Province |
| *Alpihia officinarum* Hance | Guangxi Province | *Rumex nepalensis* Spreng. | Sichuan Province | *Anemarrhena asphodeloides* Bge. | Inner Mongolia |
| *Pueraria lobata* (Willd.) Ohwi | Guangxi Province | *Arctium lappa* L. | Sichuan Province | *Gardenia jasminoides* Ellis | Sichuan Province |

TABLE 1-continued

Name and origin of 114 kinds of traditional Chinese herbs

| Latin name | Origin | Latin name | Origin | Latin name | Origin |
| --- | --- | --- | --- | --- | --- |
| *Dryopteris crassirhizoma* Nakai | Sichuan Province | *Taraxacum mongolicum* Hand.-Mazz. | Hebei Province | *Gleditsia senensis* Lam. | Sichuan Province |

2. Reagent and Materials

Absolute ethyl alcohol (EtOH) and disodium hydrogen phosphate ($Na_2HPO_4$) were purchased from Chongqing Chuandong (Group) Chemical Factory Co. Ltd.; AB-8 Macroporous adsorption resin and D001 cation exchange gel column were purchased from Chemical Plant of NanKai University in Tianjin; Trifluoroacetic acid (TFA) was purchased from Tianjin Guangfu Fine Chemical Research Institute; methanol (MeOH) was purchased from Hyclone company (USA); GIBCO®DMEM culture medium was purchased from Invitrogen company (USA); fetal calf serum (NCS) was purchased from Hyclone company (USA); PBS (20 mM, pH 7.2) was purchased from WuHan Boster Biological Technology, LTD; hydrochloric acid (HCl) was purchased from Chongqing Chuandong chemical plant (Group) Co., Ltd.; RAW264.7 cells and reference strain *Escherichia coli*. were purchased from American Type Culture Collection (ATCC); LPS, Poly I:C, polymyxin B (PMB), lipid A, FITC-labeled LPS, 5-FAM CpG DNA and 3-(4,5)-dimethylthiahiazo(-z-y1)-3,5-di phenytetrazolium-romide (MTT) was purchased from Sigma company (USA); Pam3csk4 was purchased from Invitrogen company (USA); recombinant murine TNF-α and IL-6 were purchased from PeproTech company (USA); the biosensor cuvette and immobilized reagents are purchased from Thermo company (USA); Tachypleus amebocyte lysate and LPS-free water were purchased from A&C Biological Ltd, Zhanjiang, China; murine TNF-α and IL-6 ELISA Kits were purchased from R&D company (USA); NF-κB ELISA Kit was purchased from Active Motif company (Japan); real-time PCR Kit was purchased from TOYOBO company (Japan); antibody was purchased from Santa Cruz company (USA) and CST company (USA); ECL Western Blotting Kit was purchased from pierce company (USA); luciferase reporter gene plasmid and Kit were purchased from Promega company (USA); KM mice (SPF grade) was purchased from the Experimental Animal Center of the Third Military Medical University.

Embodiment 1: Binding Assay of 114 Kinds of Traditional Chinese Medicine Decoction with Lipid A and CpG DNA 1.1. Methods Immobilization of lipid A and CpG DNA: Using Optically-Based Affinity Biosensors technology, Lipid A, the biologic active centres of LPS, and CpG DNA were respectively, immobilized on the reacting surfaces of cuvettes in an IAsys plus affinity biosensor according to the manufacturer's instructions of IAsys Affinity Sensor. The end of hydrophobic side chain of lipid A was immobilized on cuvette with hydrophobic surface, and the phosphate group (active group of lipid A) at the other end was floating and exposing to the outside, which act as target spot of binding with active constituents for disease treatment in traditional Chinese medicine. The active constituents in solution were binded to lipid A through electrostatic interaction. Biotinylated CpG DNA was immobilized on the surface of a biotin cuvette by linking to avidin, which had been coated on the surface of a biotin cuvette, and then the unlabeled group of CpG DNA was floating and exposing to the outside, which act as target spot of binding with active constituents for disease treatment in traditional Chinese medicine. The active constituents in solution were binded to CpG DNA through the electrostatic interaction and embodiment.

Detection of the aqueous herbal extract: The crude drugs of 114 traditional Chinese herbs were pulverized. 1 g of each powder was added with 10 ml distilled water, boiled at 100° C. for 1.5 h, centrifuged at 4000 rpm for 20 min, filtrated and then collected the supernatant. 5 μl of aqueous herbal extracts of each herb were used to detect their binding with lipid A or CpG DNA. Here are the steps: Binding reaction: 45 μl PBS was added in cuvette; then 5 μl samples was added in cuvette; liquid were draw-out after binding response reach a plateau; Dissociation: Cuvette was washed thrice in 50 μl PBS; liquid were draw-out after dissociation reach a plateau; Regeneration: Cuvette was washed thrice in 50 μl 0.1N HCl; liquid were draw-out after regeneration reach a plateau; Cuvette was washed thrice in 50 μl PBS; next cycle was started to detect new sample after curves back to baseline levels and smoothed. Data analysis was performed using the FASTplot software after detection finished.

Figure 1B:
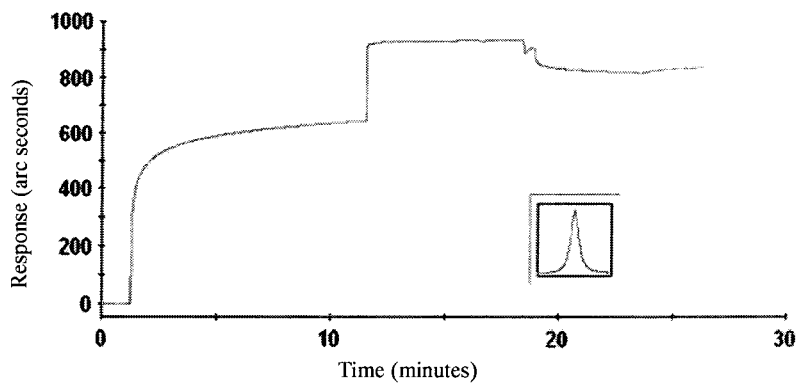
Figure 1C:
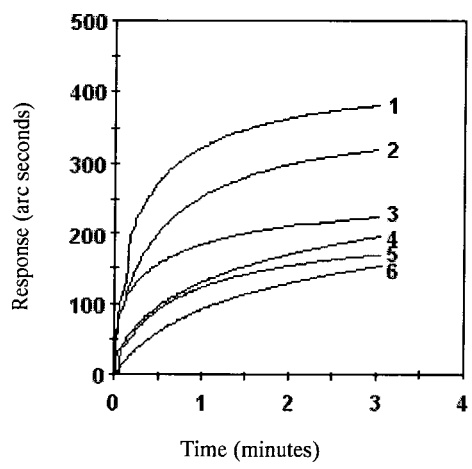
Figure 1D:
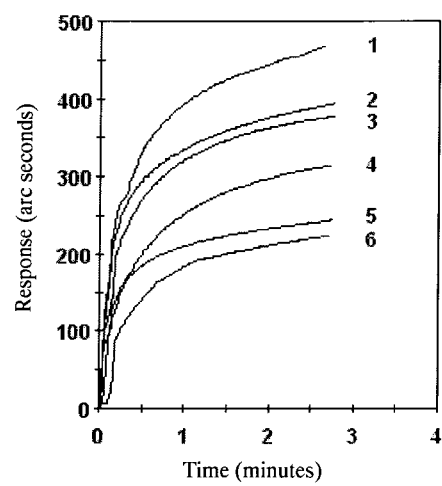

1.2. Results: In the 114 kinds of traditional Chinese herbs, 6 kinds of herbs such as *Lycii cortex* have high affinity with both lipid A and CpG DNA, among which, *Lycii cortex* has the highest affinity. The results suggest that *Lycii cortex* has greater potential of containing active constituents antagonizing LPS and CpG DNA than other traditional Chinese herbs, so it was selected as study object of extraction and separation. The results were shown in FIG. 1. Wherein FIG. 1a is a response curve of immobilization of lipid A; FIG. 1b is a response curve of immobilization of CpG DNA; FIG. 1c shows binding reaction of lipid A with *Lycii cortex* and other 6 kinds of traditional Chinese herbs; FIG. 1d shows binding reaction of CpG DNA with *Lycii cortex* and other 6 kinds of traditional Chinese herbs.

Embodiment 2: Extraction and Separation of Kukoamine A and Kukoamine B, Active Constituents Antagonizing LPS and CpG DNA in *Lycii cortex*

2.1 Separation Via Macroporous Adsorption Resins and Screening of the Active Site 2.1.1 Methods: 500 g *Lycii cortex* was added with 5 L distilled water, soaked for 24 h, boiled at 100 for 1 h, filtered by coarse filter paper, and centrifuged at 8000 rpm/min for 30 min, and the supernatant was collected and concentrated to 1 L under reduced pressure. The supernatant was loaded onto AB-8 Macroporous adsorption resin, and eluted with distilled water and gradient ethanol (10%, 20%, 40% and 100%) successively. The eluted fractions were separately collected, and lyophilized after concentrated under reduced pressure. Five constituents were obtained, and named CL-1 to -5 according to their elution order. CL constituents were separately dissolved in PBS to make 1.0 mg/ml solution, 5 μl of which were loaded. Their binding activity with lipid A and CpG DNA were detected according to methods of embodiment 1.

Figure 2A:
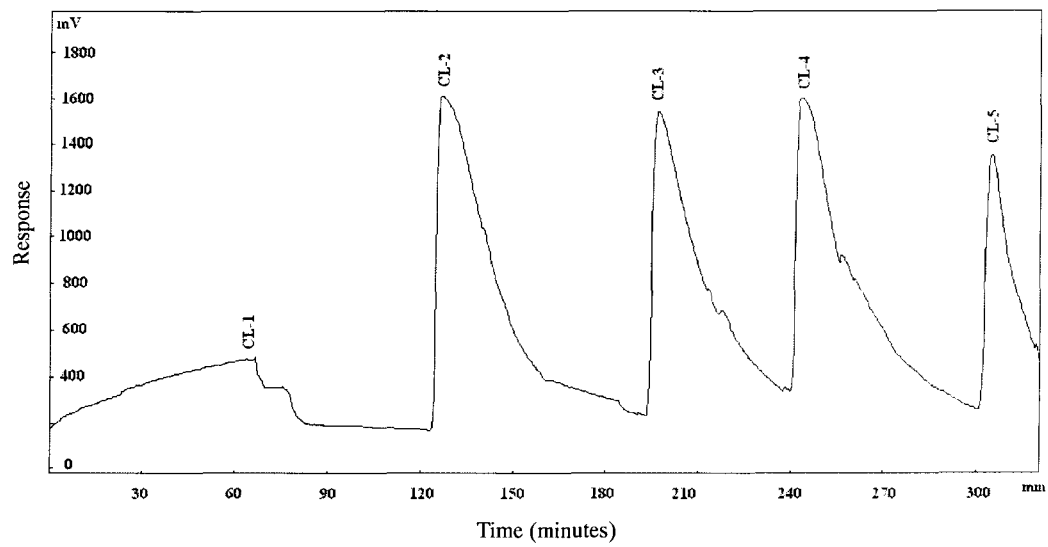
FIGS. 2a, 2b, and 2c show constituents separation of CL-1~5 and their binding reactions with lipid A and CpG DNA.
Figure 2B:
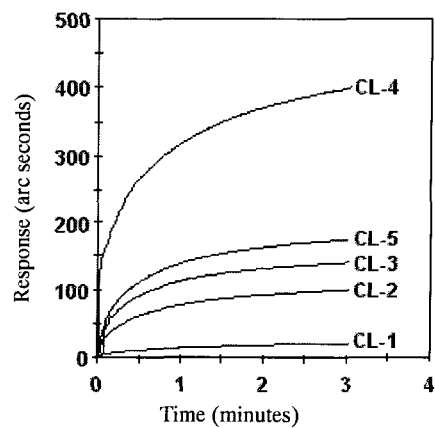
Figure 2C:
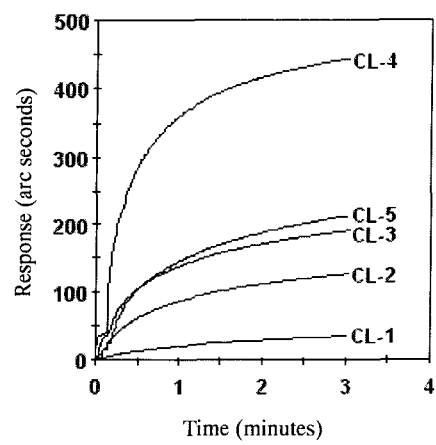

2.1.2 Results: Among the 5 constituents, CL-4 has the highest affinity with lipid A and CpG DNA. The results suggest that CL-4 is the main active site of CL constituents, therefore, CL-4 was selected for further separation. The results were shown in FIG. 2. Wherein FIG. 2a is the chromatogram of constituent separation of CL-1 to -5; FIG. 2b shows binding reaction of CL-1 to -5 constituents with lipid A; FIG. 2c shows binding reaction of CL-1 to -5 constituents with CpG DNA.

2.2 Separation Via Cation Exchange Gel Column and Screening of the Active Site 2.2.1 Methods: CL-4 lyophilization powder was diluted into ultrapure water to make 100 mg/ml solution, filtered by a 0.45 μm filter membrane, loaded onto D001 cationic exchange gel column, and eluted with distilled water, 0.3 M Na2HPO4 and 0.5 M Na2HPO4 successively. The eluted fractions were separately collected, and lyophilized after concentrated under reduced pressure. Three constituents were obtained, and named CL-4a, -4b and -4c according to their elution order. CL-4 constituents were separately dissolved in PBS to make 1.0 mg/ml solution, 5 μl of which were loaded. Their binding activity with lipid A and CpG DNA were detected according to methods of embodiment 1.

Figure 3A:
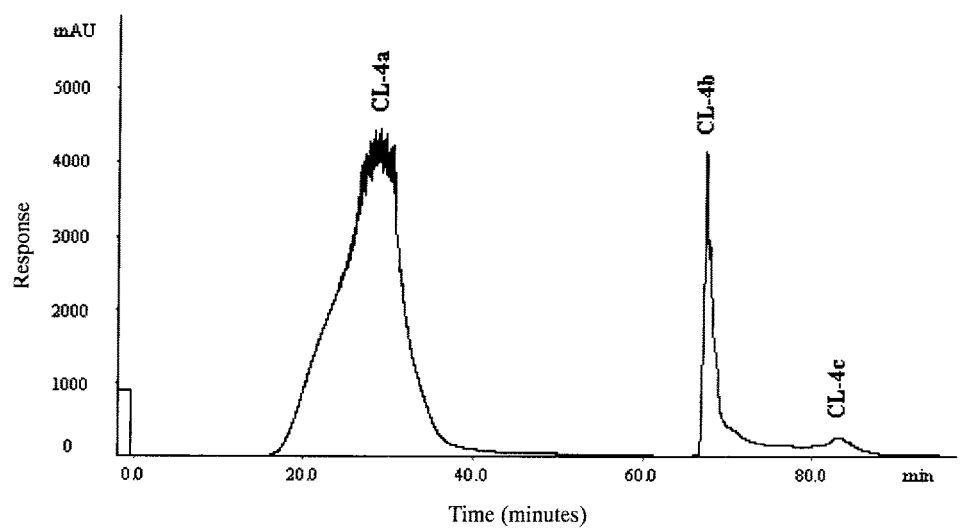
FIGS. 3a, 3b, and 3c show constituents separation of CL-4a, -4b and -4c and their binding reactions with lipid A and CpG DNA.
Figure 3B:
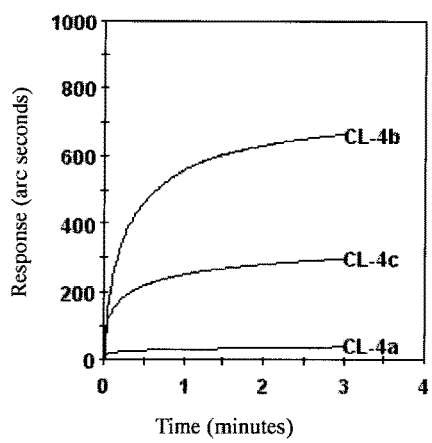
Figure 3C:
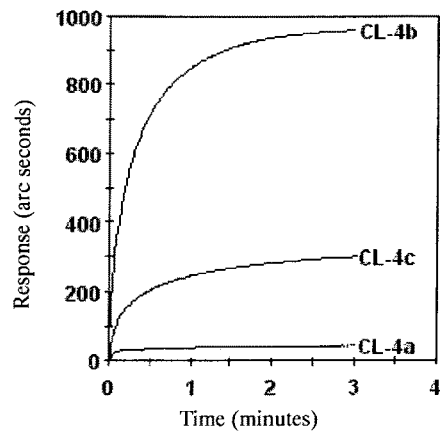

2.2.2 Results: Three constituents were obtained, CL-4a, -4b and -4c. Among which CL-4b has the highest affinity with lipid A and CpG DNA. The results were shown in FIG. 3. Wherein FIG. 3a is chromatogram of constituents separation of CL-4a, -4b and -4c; FIG. 3b shows binding reaction of CL-4 constituents with lipid A; FIG. 3c shows binding reaction of CL-4 constituents with CpG DNA.

2.3 Identification of CL-4b Antagonistic Activities on LPS or CpG DNA 2.3.1 LPS-Neutralization of CL-4b In Vitro 2.3.1 Methods: CL-4b was dissolved into LPS-free water to make 8 μg/ml solution, and incubated with equal volume of LPS (1 ng/mL) at 37° C. for 30 min. Subsequently, 100 μl mixed solution of CL-4b and LPS was added with equal volume of the quantitative TAL reagents dissolved in LPS-free water, gently shaked to mix the contents, and reacted at 37° C. for 60 min in kinetic tube reader. The agglutination of TAL reagent induced by the existence of non-neutralized LPS was measured. The mixture of LPS and equal volume of LPS-free water act as positive control. Each group contained three repeated tubes. The result was expressed in EU/ml, the endotoxin unit of LPS. Operation was performed according to the manufacturer's instructions of EDS-99 Bacterial Endotoxin Detecting system.

Figure 4:
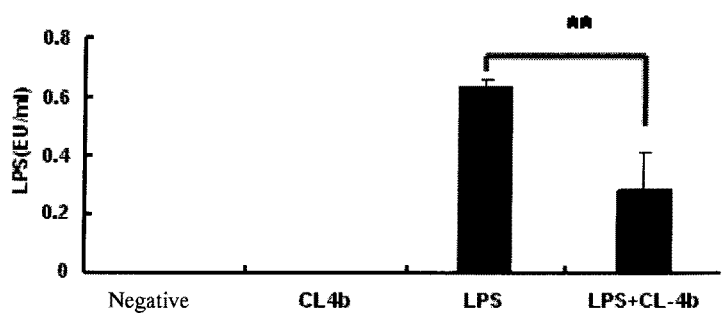
FIG. 4 shows the neutralization of CL-4a constituents with LPS in vitro, and the symbol ** in FIG. 4 means $p<0.01$ vs LPS.

2.3.1.2 Results: Cl-4b can not lead to TAL agglutination by itself, but it can significantly reduce the agglutination induced by LPS after incubated with LPS for 30 min. The result suggests that CL-4b has neutralizing activity on LPS. The results were shown in FIG. 4.

2.3.2 Inhibition of CL-4b on TNF-α Release in RAW264.7 Cells Induced by LPS and CpG DNA 2.3.2.1 Methods: RAW 264.7 cells were adjusted to $1\times10^6$/ml in DMEM supplemented with 10% NCS (v/v), transferred into 96-well plate (200 μl per well), cultured at 37° C. in a 5% CO2 humidified incubator for 4 h, and loaded after cells attachment; for the purpose of the experiment three groups were established: medium group, stimulation group and drug treatment group, and each group contained three repeated wells; medium group was added with no reagent; stimulation group was added with LPS (final concentration of 100 ng/ml) or CpG DNA (final concentration of 10 μg/ml); drug treatment group was added with CL-4b (final concentration of 200 μg/ml), as well as LPS (final concentration of 100 ng/ml) or CpG DNA (final concentration of 10 μg/ml); cells were cultured at 37° C. in a 5% CO2 humidified incubator for 24 h, and the supernatant was collected for further detection. Detections of TNF-α and IL-6 were performed according to the manufacturer's instructions of ELISA kit, and the result was expressed by means of mean±standard deviation.

Figure 5A:
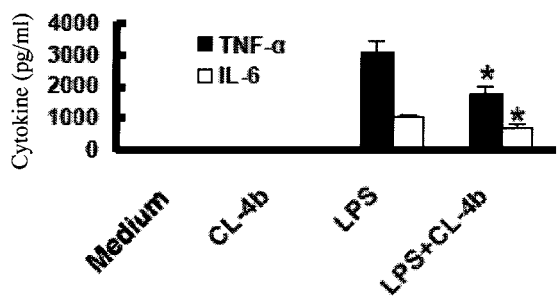
FIGS. 5a and 5b show the inhibition of CL-4b constituents on TNF-α release in RAW264.7 cells induced by LPS and CpG DNA (CpG).
Figure 5B:
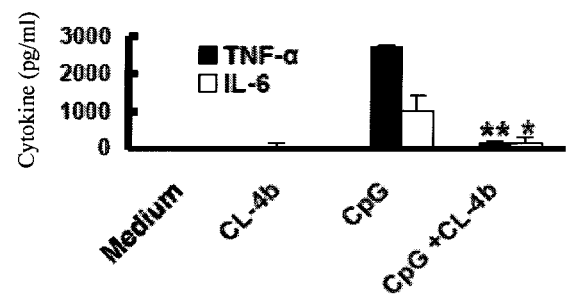

2.3.2.2 Results: CL-4b does not induce the release of TNF-α and IL-6 in RAW264.7 cell by itself, but it can significantly reduce the release of TNF-α and IL-6 in RAW264.7 cell induced by LPS and CpG DNA. The result suggested that CL-4b has antagonistic activity on LPS or CpG DNA in vitro. The results were shown in FIG. 5. Wherein FIG. 5a shows the inhibition of CL-4b on the release of TNF-α and IL-6 in RAW264.7 cells induced by LPS, and FIG. 5b shows the inhibition of CL-4b on the release of TNF-α and IL-6 in RAW264.7 cells induced by CpG DNA.

2.3.3 CL-4b Protection on Mice Challenged by Lethal Dose of Heat-Killed *Escherichia coli*

2.3.3.1 Methods:

Preparation of heat-killed *Escherichia coli* (*E. coli*) ATCC 35218: Bacteria culture was performed according to Clinical Laboratory Procedures. Single bacterial colony of *E. coli* from LB agar plates were picked and transferred into 10 mL sterile liquid of LB broth using a sterile inoculating loop, and cultivated at 37° C. in a shaker (250 rpm). After medium become turbid, these culture medium were then transferred to 2000 mL of fresh LB medium and cultivated at 37° C. in a shaker (250 rpm) for 12 h. The suspension was collected, transferred into 1000 ml centrifuge tube, and centrifuged at 5000 rpm for 15 min. The supernatant was discarded. The bacteria were collected, washed and resuspended into sterile saline, and then centrifuged again under the same condition. Above-mentioned process was repeated thrice. The bacteria pellet was resuspended with a pipet in 50 ml sterile saline, transferred into 100 ml saline bottle, and boiled in electric furnace for 30 min. Then the suspension of heat-killed *Escherichia coli* was obtained. The suspension of *E. coli* was diluted by 100 fold, and measured OD value at 600 nm on nucleic acid protein analyzer. Conversion was made according to the regression equation of OD value and concentration, and the suspension was diluted according to the conversion result. Then the operating fluids for mice injection were obtained.

Observation of CL-4b protection on mice challenged by heat-killed *Escherichia coli*: A total of 40 Kunming mice (18~20 g), half male and half female, were divided into three groups randomly: CL-4b control group, heat-killed *E. coli* group and CL-4b treatment group. Each group has 10 mice, half male and half female. CL-4b control group was injected with CL-4b (60 mg/kg) and sterile saline; heat-killed *E. coli* group was injected with heat-killed *Escherichia coli* ($1.0\times10^{10}$ CFU/ml) and sterile saline; CL-4b treatment group was injected with CL-4 (60 mg/ml) at 10 min after heat-killed *E. coli* injection. The injection volume of each solution was 200 μl per 20 g body weight via tail vein. Injection volume of each mouse was 200 μl per 20 g body weight. The general status and mortality rate of mice were observed for 7 days, and survival differences between CL-4b control group and CL-4b treatment group were compared.

Figure 6:
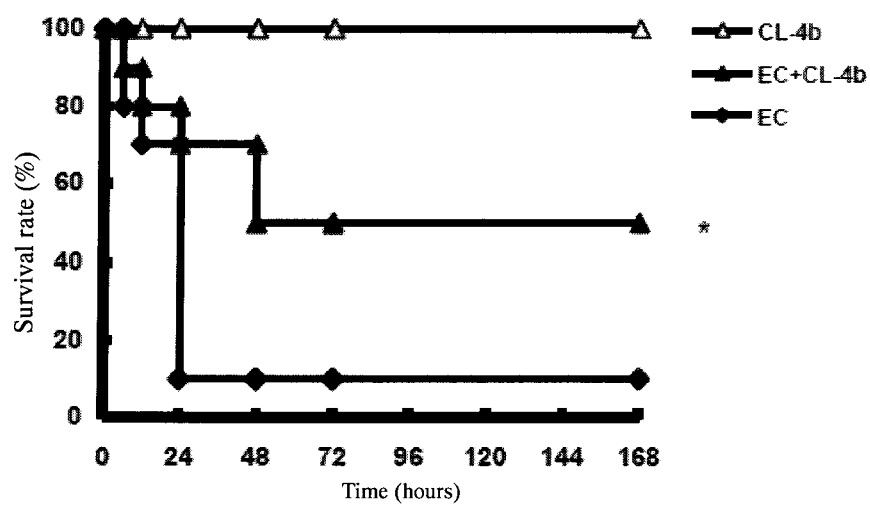
FIG. 6 shows the protection of CL-4b constituents on mice challenged by lethal dose of heat-killed *Escherichia coli* (EC) and the symbol * in FIG. 6 means $p<0.05$ vs *E. coli*. (EC).

2.3.3.2 Results: Nothing but CL-4b (60 mg/kg) and sterile saline have no influence on general status and survival rates of mice; The mortality rate of heat-killed *E. coli* group was 90% at 3 days; Intervention with CL-4b (60 mg/kg) while injecting heat-killed *E. coli* can decrease the mortality rate of mice challenged by heat-killed *E. coli* to 50%. The results show that CL-4b has a significant protective effect on mice challenged by lethal dose of heat-killed *E. coli*. The results were shown in FIG. 6.

2.4 Isolation by Preparative High-Performance Liquid Chromatography 2.4.1 Methods:

The choice of chromatographic conditions: An Agilent Technology 1200 Series analytical HPLC system was used for composition analysis; CL-4b was diluted with mobile phase (A (0.1% TFA): B (MeOH)=80:20, v/v) to make 0.5 mg/ml solution; the analysis was carried out with an Agilent XDB-C18 analytical column (150 mm×4.6 mm, 5 μm) packed with the octadecyl silane chemically bonded silica; the detection wavelength was 280 nm; flow rate was at 1 ml/min; column temperature was 25; sample size was 10 μl;

Preparation of high performance liquid chromatography: An Agilent Technology 1100 Series preparative HPLC system was used for isolation; CL-4b was diluted with mobile phase (A (0.1% TFA): B (MeOH)=80:20, v/v) to make 20 mg/ml solution; the analysis was carried out with an Agilent KF-C18 column (200 mm×20 mm, 10 μm) packed with the octadecyl silane chemically bonded silica; the detection wavelength was 280 nm; flow rate was at 10 ml/min; column temperature was room temperature; sample size was 20 ml; the Chromatographic peak eluates of retention time 16 to 20 and 20 to 30 min, were separately collected and dried under reduced pressure; two components were obtained and named CL-4b$_1$ and CL-4b$_2$ according to the order of their retention time; CL-4b$_1$ and CL-4b$_2$ were dissolved in PBS to make 1.0 mg/ml solution, 5 μl of which were loaded onto HPLC; their binding activity with lipid A and CpG DNA were detected according to methods of embodiment 1.

Figure 7A:
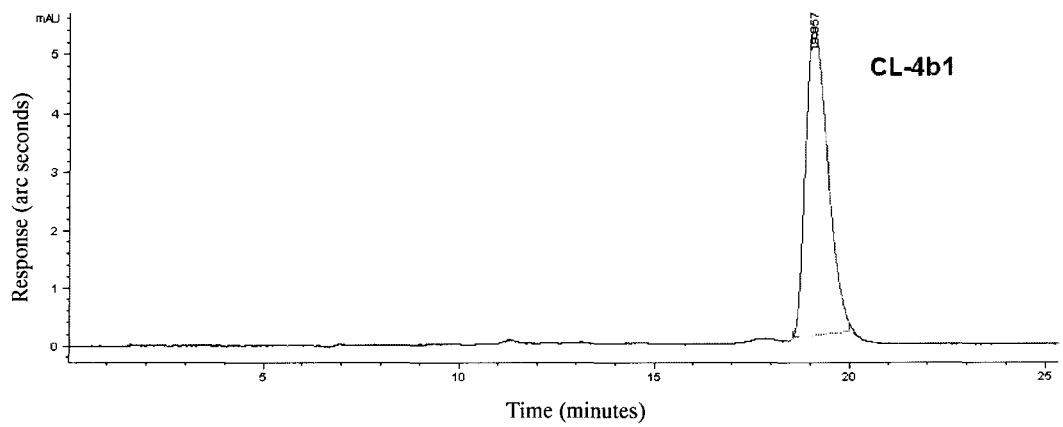
FIGS. 7a and 7b show diagrams of high efficiency liquid chromatography (HPLC) analysis of CL-4b constituents.
Figure 7B:
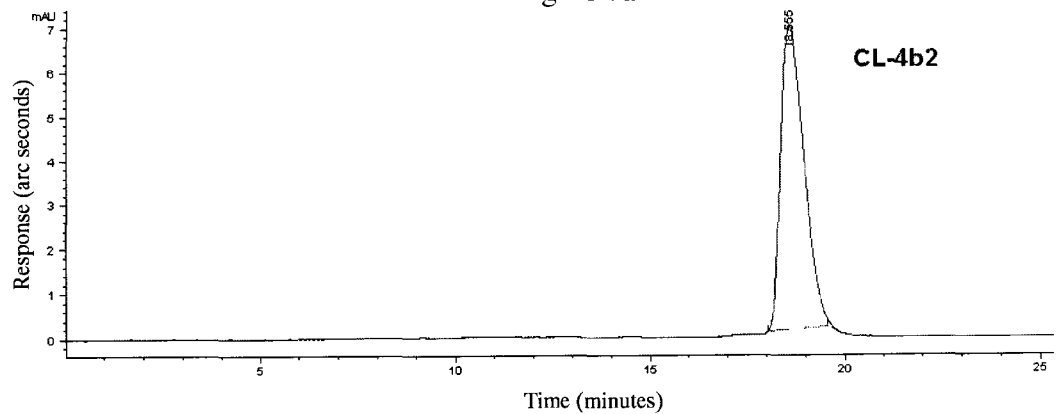

2.4.2 Results: Two major components, CL-4b$_1$ and CL-4b$_2$, were obtained by HPLC analysis and preparation. The chromatogram was shown in FIG. 7. Wherein FIG. 7*a* is a HPLC diagram of CL-4b$_1$ component, FIG. 7*b* is a HPLC diagram of CL-4b$_2$ component. These two components were preliminarily recognized as single compound by peak purity analysis in HPLC.

2.5 Identification of the Chemical Structure of CL-4b$_1$ and CL-4b$_2$ 2.5.1 Methods: CL-4b$_1$ and CL-4b$_2$ were analyzed by UV spectrum, IR spectrum, NMR spectrum and mass spectrum.

2.5.2 Results: CL-4b$_1$ and CL-4b$_2$ are both pale yellow crystals. UV spectrum detection shows that the absorption peaks ($\lambda_{max}$) of the two components are both at point 281 nm (methanol); and results of ESI-MS of the two components are both [M+H]$^+$ m/z 531, which suggests that they are a pair of isomeride. The results of NMR spectrum are shown in Table 2:

TABLE 2

NMR spectrum detection results of kukoamine A and kukoamine B

| | | Kukoamine A | | Kukoamine B | |
|---|---|---|---|---|---|
| | | C | H | C | H |
| 2 | t | 34.9 | 3.25 | 38.50 | 3.18 |
| 3 | m | 25.6 | 1.75 | 28.41 | 1.68 |
| 4 | t | 44 | 2.79 | 47.46 | 2.55 |
| 6 | t | 46.5 | 2.88 | 50.10 | 2.75 |

TABLE 2-continued

NMR spectrum detection results of kukoamine A and kukoamine B

| | | Kukoamine A | | Kukoamine B | |
|---|---|---|---|---|---|
| | | C | H | C | H |
| 7 | m | 22.4 | 1.75 | 25.75 | 1.48 |
| 8 | m | 22.4 | 1.75 | 27.97 | 1.37 |
| 9 | t | 46.5 | 2.88 | 50.56 | 3.23 |
| 11 | t | 44 | 2.79 | 45.55 | 3.38 |
| 12 | m | 25.6 | 1.75 | 27.88 | 1.82 |
| 13 | t | 34.9 | 3.25 | 39.78 | 2.82 |
| 1' | — | 131.9 | | 135.9 | |
| 2' | d | 115.2 | 6.66 | 119.1 | 6.76 |
| 3' | — | 144.1 | | 146.8 | |
| 4' | — | 142.7 | | 145.2 | |
| 5' | d | 115.4 | 6.69 | 119.2 | 6.83 |
| 6' | dd | 119.8 | 6.55 | 123.6 | 6.67 |
| 7' | t | 30.3 | 2.68 | 33.28 | 2.82 |
| 8' | t | 36.6 | 2.51 | 39.78 | 2.55 |
| 9' | — | 174.8 | | 179.2 | |
| 1" | — | 131.9 | | 136.5 | |
| 2" | d | 115.2 | 6.66 | 119.3 | 6.78 |
| 3" | — | 144.1 | | 146.9 | |
| 4" | — | 142.7 | | 145.3 | |
| 5" | d | 115.4 | 6.69 | 119.4 | 6.84 |
| 6" | dd | 119.8 | 6.55 | 123.8 | 6.68 |
| 7" | t | 30.3 | 2.68 | 33.65 | 2.82 |
| 8" | t | 36.6 | 2.51 | 37.00 | 2.68 |
| 9" | — | 174.8 | | 178.9 | |

By structural analysis, CL-4b$_1$ was identified as Kukoamine A (KA), and CL-4b$_2$ was identified as Kukoamine B (KB).

Embodiment 3: Affinity Detection of KA and KB with Lipid A and CpG DNA in Vitro 3.1 Methods: KA and KB were separately dissolved to make 100 μM operating solution; 5 μl of the solution was loaded; their binding activity with lipid A and CpG DNA were detected according to methods of embodiment 1.

Figure 8A:
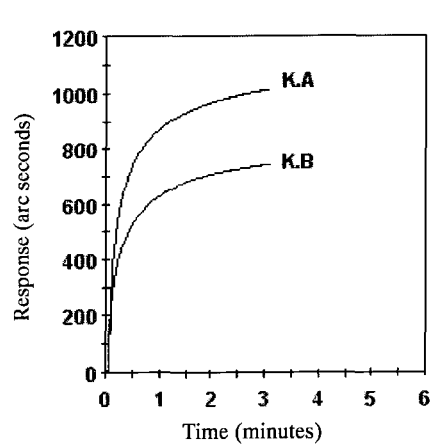
FIGS. 8a and 8b show binding curves of KA and KB with lipid A and CpG DNA in vitro.
Figure 8B:
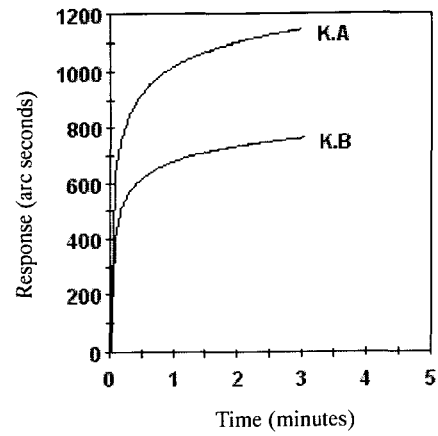

3.2 Results: KA and KB both have high affinity with lipid A and CpG DNA. The results were shown in FIG. 8. Wherein FIG. 8*a* shows the affinity detection of KA and KB with lipid A, and FIG. 8*b* shows the affinity detection of KA and KB with CpG DNA.

Embodiment 4: Neutralizing Activity of KA and KB with LPS In Vitro 4.1 Methods: KA and KB (1, 2 and 4 μg/ml) were separately mixed with equal volume of LPS (2.0 ng/ml) and pre-incubated at 37 for 30 min; LPS control group was added with equal volume of nonpyrogenic water; LPS value was detected by kinetic turbidimetric limulus test after incubation; detection of each concentration was repeated three times; LPS content was expressed by means of mean±standard deviation; operation was performed according to the manufacturer's instructions of EDS-99 Bacterial Endotoxin Detecting system.

Figure 9:
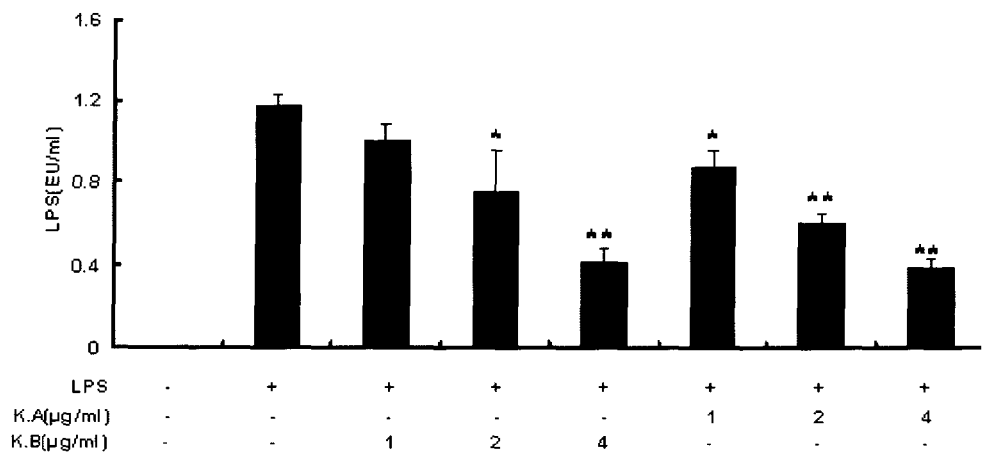
FIG. 9 shows the neutralization of KA and KB with LPS in vitro. The symbol * in FIG. 9 means $p<0.05$, and ** means $p<0.01$ vs LPS.

4.2 Results: Both KA and KB has neutralizing activity with LPS. Statistical analysis showed that KA and KB have significant neutralizing activity with LPS ($p<0.05$ or $p<0.01$), and there is an obvious dose-dependent relationship between them, which suggests that KA and KB can antagonize LPS effectively and thus play a role in the prevention and treatment of sepsis and autoimmune disease. The results were shown in FIG. 9.

Embodiment 5: Influence of KA and KB on the Binding of Fluorescently-Labeled LPS and CpG DNA with RAW264.7 Cells 5.1 Methods: RAW264.7 cells were diluted to $1\times10^6$/ml in DMEM supplemented with 10% (v/v) NCS, added into 24-well cell culture plates, cultured at 37° C. in a 5% CO2 humidified incubator for 4 h, added with KA and KB (0, 200 μg/ml) after cells attachment, and then added with FITC-labeled LPS (final concentration of 400 ng/ml) and 5-FAM CpG DNA (final concentration of 10 μg/ml); at the same time, medium group without any reagent was established; subsequently, RAW264.7 cells were incubated for 30 min, washed thrice in PBS, resuspended with a pipet and transferred into EP tube, and immobilized with 4% paraform for 10 min; then cells were washed thrice in PBS, made into cell suspension, and detected by flow cytometry; the detections of each group were repeated thrice. Mean fluorescence intensity was expressed by means of Mean±standard deviation.

Figure 10A:
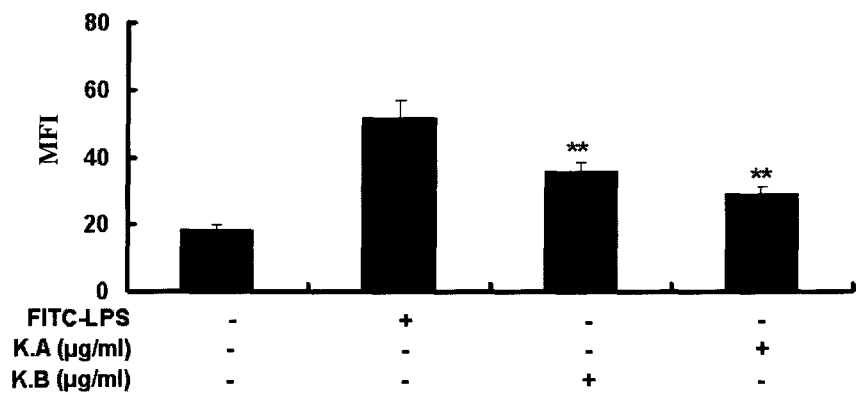
FIGS. 10a and 10b show the inhibition of KA and KB on the binding of fluorescently-labeled LPS and CpG DNA (CpG) with RAW264.7 cells.
Figure 10B:
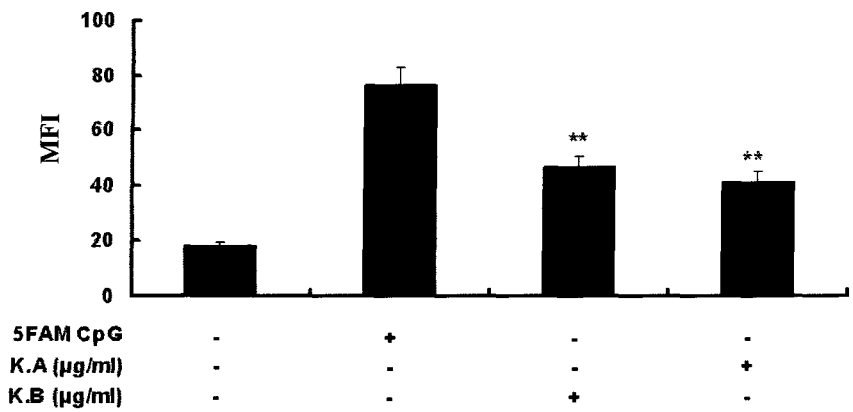

5.2 Results: KA and KB can significantly decrease the fluorescence intensity of LPS and CpG DNA ($p<0.01$) in RAW264.7 cells, which suggested that they can influence the binding of LPS and CpG DNA with RAW264.7 cells, effectively inhibit the excessive immune response induced by LPS and CpG DNA, prevent injury to the body, and thus play a role in the prevention and treatment of sepsis and autoimmune disease. The results were shown in FIG. 10. Wherein FIG. 10a shows the influence of KA and KB on the binding of fluorescently-labeled LPS with RAW264.7 cells, and FIG. 10b shows the influence of KA and KB on the binding of fluorescently-labeled CpG DNA with RAW264.7 cells.

Embodiment 6: Influence of KA and KB on Release of TNF-α in RAW264.7 Cells Induced by LPS and CpG DNA 6.1 Methods: RAW264.7 cells were diluted to $1\times10^6$/ml in DMEM supplemented with 10% (v/v) NCS, added into 96-well plates (200 μl per well), and cultured at 37° C. in a 5% CO2 humidified incubator for 4 h until cells adhere to the wall; culture medium were replaced with fresh culture medium, added with KA and KB (final concentrations of 0, 50 and 100 ng/ml), and added with LPS (final concentration of 100 ng/ml) and CpG DNA (final concentration of 10 μg/ml); at the same time, medium group without any reagent was established; subsequently, RAW264.7 cells were incubated for 4 h; and the supernatant was collected for further detection; detection of the TNF-α concentration was performed according to the manufacturer's instructions of ELISA kit. Result was expressed by means of mean±standard deviation.

Figure 11A:
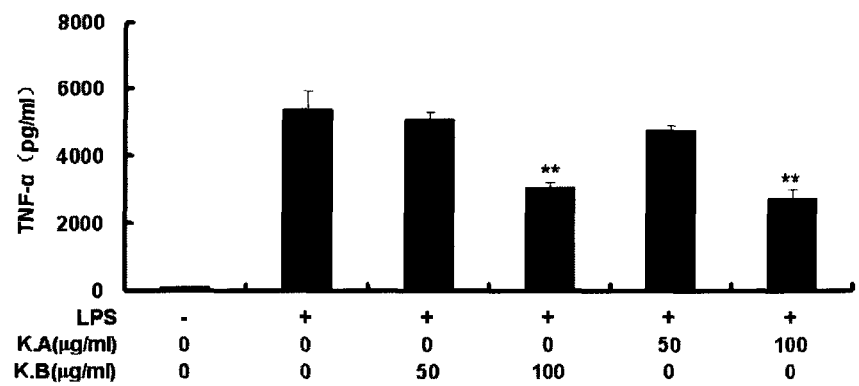
FIG. 11a and 11b show the inhibition of KA and KB on TNF-α release in RAW264.7 cells induced by LPS and CpG DNA (CpG).
Figure 11B:
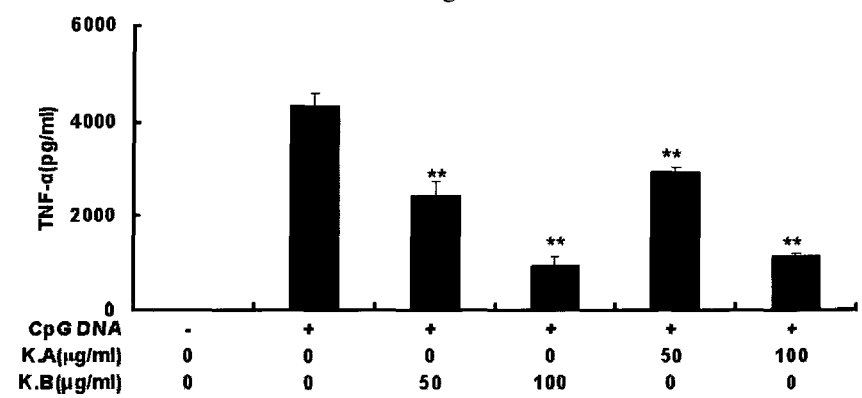

6.2 Results: KA and KB can inhibit the release of TNF-α induced by LPS and CpG DNA in a dose-dependent manner, which has significant difference compared with control group ($p<0.01$). Extended release of a large amount of TNF-α play an important role in the pathological damage in sepsis and autoimmune disease, therefore inhibition on TNF-α release can effectively prevent and cure sepsis and autoimmune disease. The results were shown in FIG. 11. Wherein FIG. 11a shows the influence of KA and KB on the release of TNF-α in RAW264.7 cells induced by LPS, FIG. 11b shows the influence of KA and KB on the release of TNF-α in RAW264.7 cells induced by CpG DNA.

Embodiment 7: Detection of Influence of KA and KB on Cell Vitality (MTT Assay)

7.1 Methods: MTT assay were adopted for cell vitality detection; RAW264.7 cells were diluted to $1\times10^6$/ml in DMEM medium, added into 96-well plates (200 μl per well), and cultured at 37° C. in a 5% CO2 humidified incubator for 4 h; treatment group was successively added with KA and KB (final concentration of 200 μg/ml); no reagent was added in medium group; each group has 6 parallel wells; subsequently, RAW264.7 cells were cultured for 24 h; the supernatant was discarded; each well was added with 180 μl culture medium and 20 μl MTT solution (5 mg/ml), and cultured for 4 h; the supernatant was removed; 150 μl of dimethyl sulphoxide was added into each well; the 96-well plates were shook for 10 min for the dissolution of the crystals; RAW264.7 cells vitality was expressed as absorbance values at 550 nm (OD550) of each well; the absorbance values between treatment group and medium group were compared.

Figure 12:
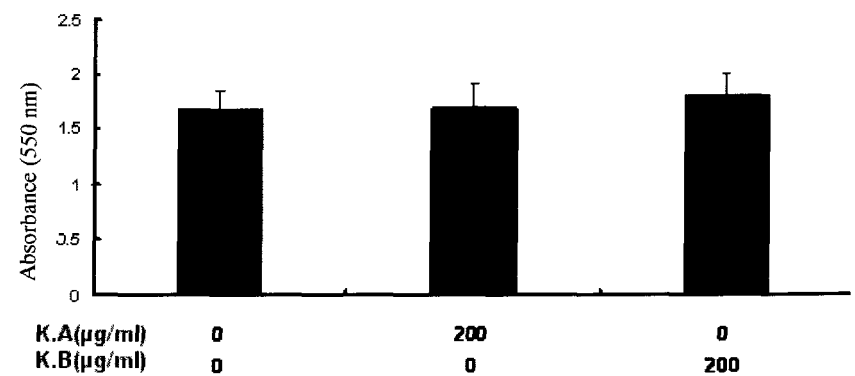
FIG. 12 shows the influence of KA and KB on RAW264.7 cells vitality.

7.2 Results: Result of MTT assay shows that KA and KB (200 μg/ml) have no influence on RAW264.7 cells vitality ($p>0.05$), which suggests that inhibition of KA and KB (200 μg/ml) on the release of TNF-α in RAW264.7 cells is not induced by their cytotoxicity. The results were shown in FIG. 12.

Embodiment 8: Antagonism of KA and KB on LPS and CpG DNA In Vivo 8.1 Methods: Supernatant of heat-killed E. coli was prepared according to 2.3.3 items of embodiment 2; absorbance values of the supernatant were assayed at 600 nm ($OD_{600}$ value $1.0\approx1.0\times10^{10}$ CFU/ml); a total of 84 Kunming mice, half male and half female, were divided into three groups randomly: heat-killed E. coli control group, KA (40 mg/kg) plus heat-killed E. coli group and KB (40 mg/kg) plus heat-killed E. coli group; each group has 28 mice; after animals were weighed, heat-killed E. coli control group was injected with heat-killed E. coli($1.1\times10^{10}$ CFU/Kg); the other two groups were respectively injected with KA or KB (40 mg/kg) at 10 min after injection of heat-killed E. coli($1.1\times10^{10}$ CFU/Kg); the total injection of each animal was 200 μl per 20 g body weight; orbital venous blood of mice was collected at time point of 0, 2, 4, 8, 12, 24, 48 and 72 h after injection; LPS level was assayed by kinetic turbidimetric limulus test, and TNF-α was assayed by ELISA.

Figure 13A:
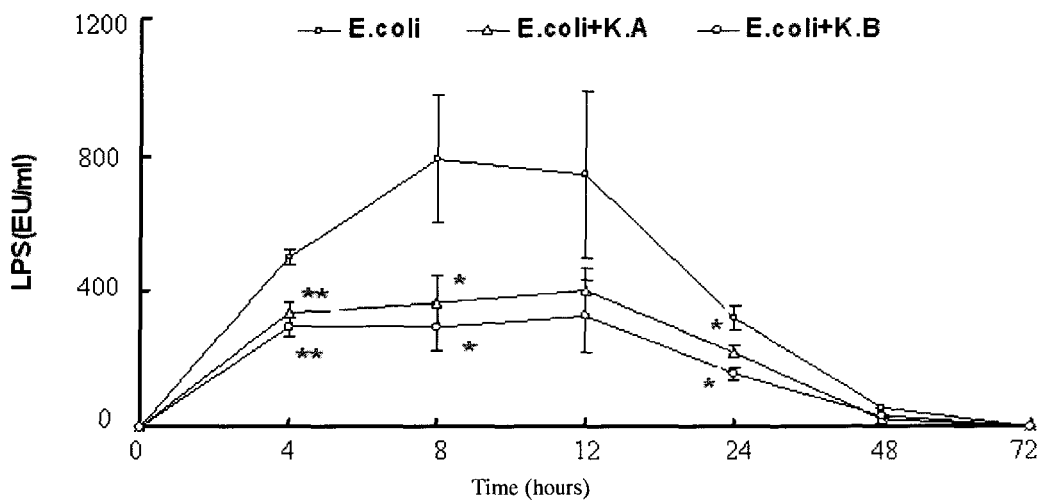
FIGS. 13a and 13b show the influence of KA and KB on LPS and TNF-α levels in blood of mice challenged by heat-killed *Escherichia coli* (*E. coli*) ATCC 35218.
Figure 13B:
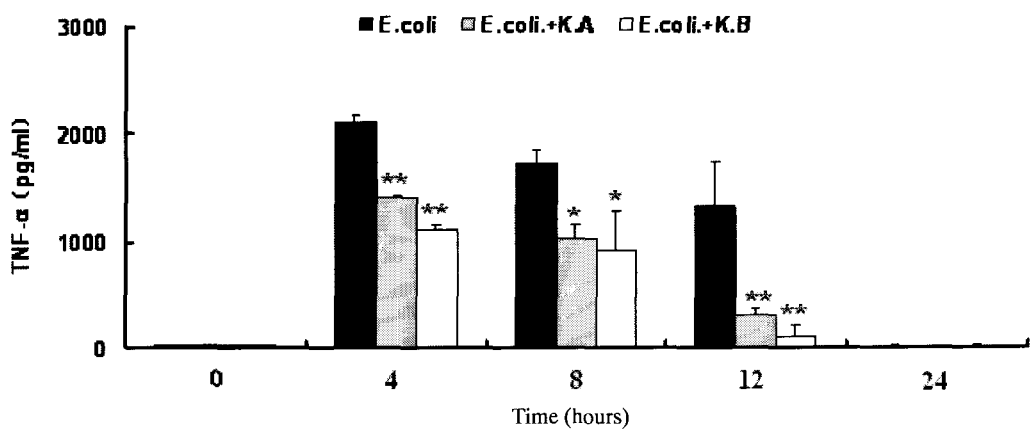

8.2 Results: Heat-killed E. coli has no proliferative activity, but it contains large amount of LPS and CpG DNA, which can simulate the stimulation of LPS and CpG DNA in vivo. The LPS and TNF-α level in mice blood of heat-killed E. coli control group began to increase rapidly 4 h after injection, and fell back to initial state within 24 to 48 h. As compared with heat-killed E. coli control group, the LPS and TNF-α level in mice blood of KA or KB treatment group at various time points were significantly decreased ($p<0.05$ or $p<0.01$). The results suggested that, KA and KB can effectively antagonize LPS and CpG DNA, inhibit extended release of a large amount of TNF-α through inhibiting the stimulation of LPS and CpG DNA, and then effectively prevent and cure sepsis and autoimmune disease. The results were shown in FIG. 13. Wherein FIG. 13a shows the influence of KA and KB on LPS level in blood of mice challenged by E. coli, and FIG. 13b shows the influence of KA and KB on TNF-α level in blood of mice challenged by E. coli.

Embodiment 9: Assessment of Affinity Constants (Dissociation Equilibrium Constant) of KB with LPS and CpG DNA 9.1 Methods: KB was separately diluted with PBS to make solutions of 0.25, 0.5, 1, 2 and 4 µM; 5 µl of each solution was separately loaded; binding reaction of KB of various concentration with LPS and CpG DNA was assayed according to the methods in embodiment 1. The dissociation equilibrium constant ($K_D$) of KB with LPS and CpG DNA was calculated using the IAsys FASTfit software.

9.2 Results: The dissociation equilibrium constant ($K_D$) of KB with LPS and CpG DNA is respectively 1.24 µM and 0.66 µM. The results were shown in Table 3.

TABLE 3

Dissociation equilibrium constant ($K_D$) of KB with LPS and CpG DNA

|  | association rate constant ($k_{ass}$) | dissociation rate constant ($k_{diss}$) | dissociation equilibrium constant ($K_D = k_{ass}/k_{diss}$) |
|---|---|---|---|
| LPS | 0.0204448 ± 0.0031071 | 16531.5 ± 648.0 | $1.23672 \times 10^{-6}$M |
| CpG DNA | 0.0419045 ± 0.0031342 | 63119.0 ± 672.4 | $6.63897 \times 10^{-7}$M |

Embodiment 10: Detection and Comparation of Binding Reaction of Polymyxin B (PMB) with LPS and CpG DNA 10.1 Methods: KB and PMB were separately diluted with PBS to make a 4 µM solution; 5 µl of each solution was loaded respectively; affinity of KB and PMB with LPS and CpG DNA was respectively assayed according to the methods in embodiment 1.

Figure 14A:
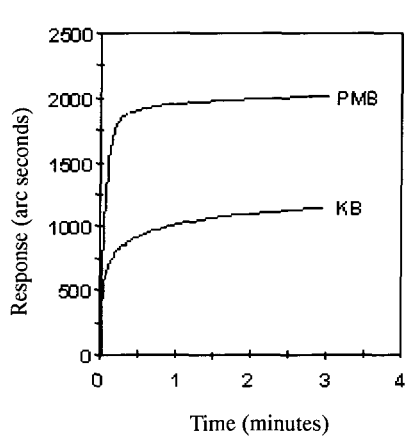
FIGS. 14a and 14b show binding reactions of KB and PMB with LPS and CpG DNA.
Figure 14B:
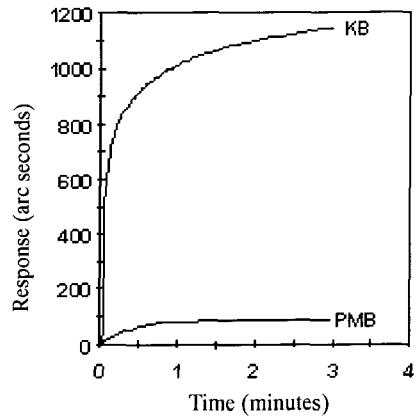

10.2 Result: PMB is an antagonistic drug of LPS. In biosensor detection, PMB has high affinity with LPS, and its binding force with LPS is almost 2 times as much as that of KB. But PMB almost has no binding effects on CpG DNA. However, KB has high affinity with CpG DNA, which suggests that KB can bind to both LPS and CpG DNA. The results were shown in FIG. 14. Wherein FIG. 14a shows the affinity detection of KB and PMB with LPS, and FIG. 14b shows the affinity detection of KB and PMB with CpG DNA.

Embodiment 11: Detection and Comparation of Neutralizing Activity of KB and PMB with LPS and CpG DNA 11.1 Methods: KB and PMB were separately diluted with LPS-free water to make solutions of 0.5, 1, 2, 4, 8, 16, 32, 64 and 128 µM; according to the methods in embodiment 4, above solutions were separately mixed with equal volume of LPS (2 ng/ml), and neutralizing activity was assayed.

Figure 15:
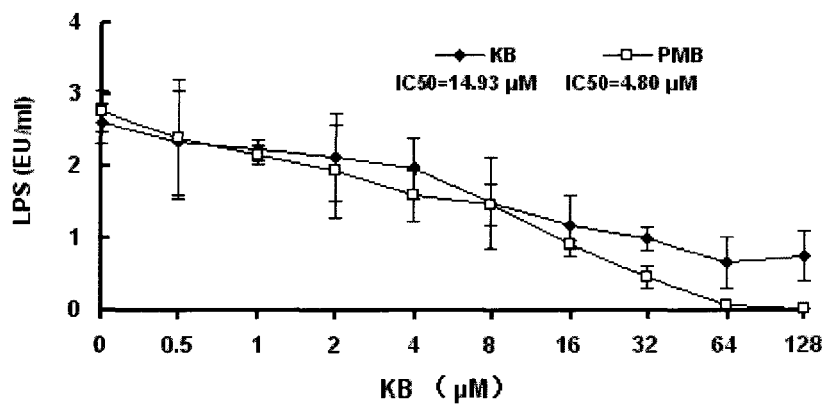
FIG. 15 shows the neutralization of KB and PMB with LPS in vitro.

11.2 Results: LPS-neutraliztion of KB is similar to PMB, which also presents a dose-dependent relationship. But inhibition effect of KB is weaker than PMB. Half inhibitory concentration ($IC_{50}$) of KB and PMB on LPS (2 ng/ml) was 14.93 µM and 4.80 µM separately. The results were shown in FIG. 15.

Embodiment 12: Inhibition of KB on the Release of TNF-α and IL-6 in RAW264.7 Cells Induced by LPS and CpG DNA 12.1 Methods: According to the method in embodiment 6, KB was dissolved in DMEM supplemented with 10% (v/v) NCS, subsequently transferred into Culture medium of RAW264.7 cells to achieved final concentrations of 100 and 200 µM, added with LPS (final concentration of 100 ng/ml) and CpG DNA (final concentration of 10 µg/ml), incubated for 24 h, and then collected supernatant; the concentration of TNF-α and IL-6 of each group was detected according to the manufacturer's instructions of ELISA kit; result was expressed by means of mean±standard deviation.

Figure 16A:
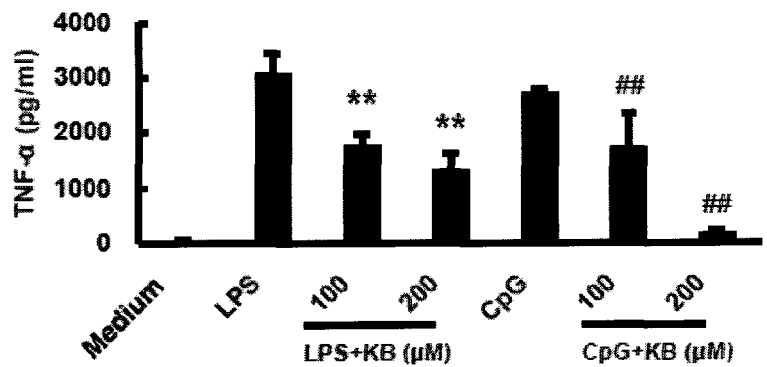
FIGS. 16a and 16b show the inhibition of KB on the release of TNF-α and IL-6 in RAW264.7 cells induced by LPS and CpG DNA (CPG).
Figure 16B:
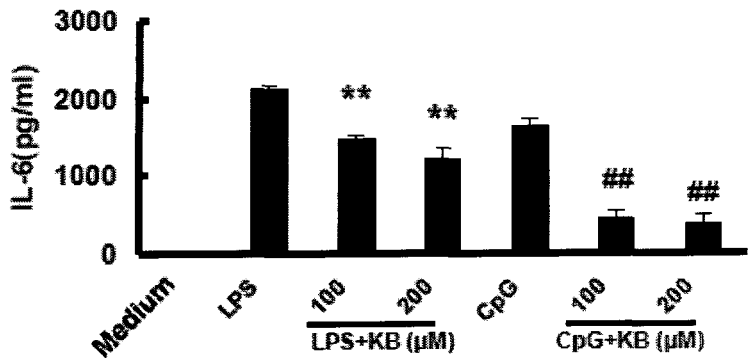

12.2 Results: KB can inhibit the release of TNF-α and IL-6 induced by both LPS and CpG DNA. The results were shown in FIG. 16. Wherein FIG. 16a shows the inhibition of KB on the release of TNF-α in RAW264.7 cells stimulated by LPS and CpG DNA, and FIG. 16b shows the inhibition of KB on the release of IL-6 in RAW264.7 cells stimulated by LPS and CpG DNA.

Embodiment 13: Comparation of the Influence of KB and PMB on the Release of TNF-α and IL-6 in RAW264.7 Cells Induced by LPS and CpG DNA 13.1 Methods: According to the method in embodiment 6, KB and PMB were separately dissolved in DMEM supplemented with 10% (v/v) NCS, subsequently transferred into culture medium of RAW264.7 cells to achieved final concentrations of 50, 100 and 200 µM, and then added with LPS (final concentration of 100 ng/ml) and CpG DNA (final concentration of 10 µg/ml); RAW264.7 cells continued to be incubated; the supernatant were collected four hours later for TNF-α detection; the supernatant were collected 12 hours later for IL-6 detection; the concentration of TNF-α and IL-6 of each group was detected according to the manufacturer's instructions of ELISA kit; result was expressed by means of mean±standard deviation.

Figure 17A:
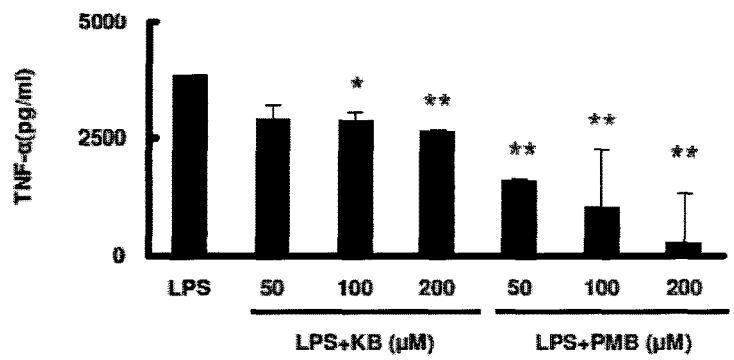
FIGS. 17a, 17b, 17c and 17d show the inhibition of KB and PMB on the release of TNF-α and IL-6 in RAW264.7 cells induced by LPS and CpG DNA (CPG).
Figure 17B:
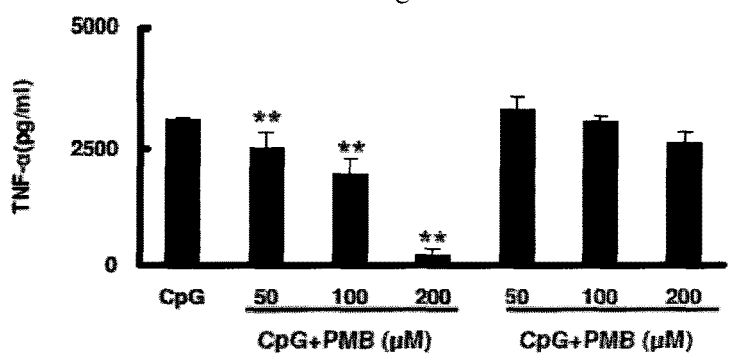
Figure 17C:
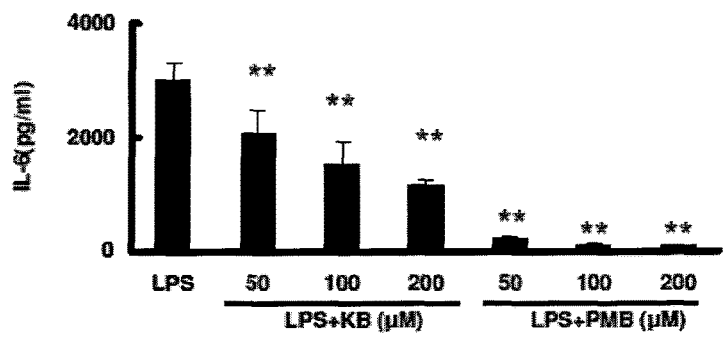
Figure 17D:
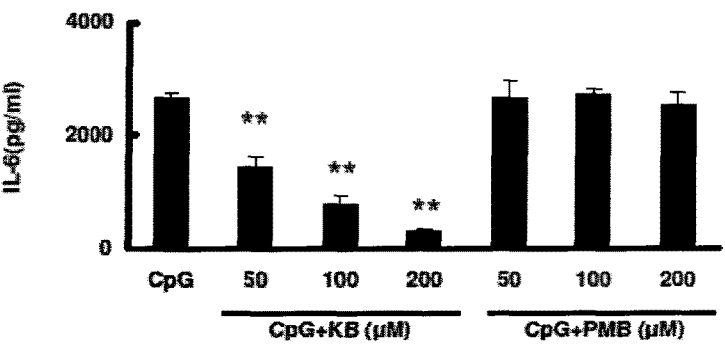

13.2 Result: KB can inhibit the release of TNF-α and IL-6 induced by both LPS and CpG DNA, and PMB can only inhibit the release of TNF-α and IL-6 induced by LPS. The results were shown in FIG. 17. Wherein FIG. 17a shows the inhibition of KB and PMB on the release of TNF-α in RAW264.7 cells stimulated by LPS; FIG. 17b shows the inhibition of KB and PMB on the release of TNF-α in RAW264.7 cells stimulated by CpG DNA; FIG. 17c shows the inhibition of KB and PMB on the release of IL-6 in RAW264.7 cells stimulated by LPS; FIG. 17d shows the inhibition of KB and PMB on the release of IL-6 in RAW264.7 cells stimulated by CpG DNA.

Embodiment 14: Effect of KB on the Release of TNF-α and IL-6 in Murine Peritoneal Macrophages Induced by LPS and CpG DNA 14.1 Methods:

Separation and culture of murine peritoneal macrophages: KM mice were killed by cervical dislocation and immediately immersed in 75% ethanol for skin degerming; then abdominal skin was aseptically cut open; precooling DMEM cell culture medium was slowly injected in exposed peritoneum with a 5 ml syringe; murine abdomen was gently massaged for sufficient cell collection; subsequently, DMEM was withdrew, transferred into 10 ml centrifuge tube, centrifuged at 500 rpm for 5 min, resuspended in DMEM supplemented with 10% (v/v) NCS, transferred into cell culture bottle, and then cultured at 37° C. in a 5% $CO_2$ humidified incubator for 2 h; culture medium was replaced with fresh culture medium to remove unattached cells; over 95% of the remained cells were murine peritoneal macrophages, which continued to be cultured and proliferated.

Loading and detection: According to the method in embodiment 6, KB and PMB were separately diluted in DMEM supplemented with 10% (v/v) NCS and transferred into culture medium of RAW264.7 cells to achieved final concentrations of 50, 100 and 200 μM; RAW264.7 cells continued to be incubated; the supernatant was collected four hours later for TNF-α detection; the supernatant at were collected 12 hours later for IL-6 detection; the concentration of TNF-α and IL-6 of each group was detected according to the manufacturer's instructions of ELISA kit; result was expressed by means of mean±standard deviation.

Figure 18A:
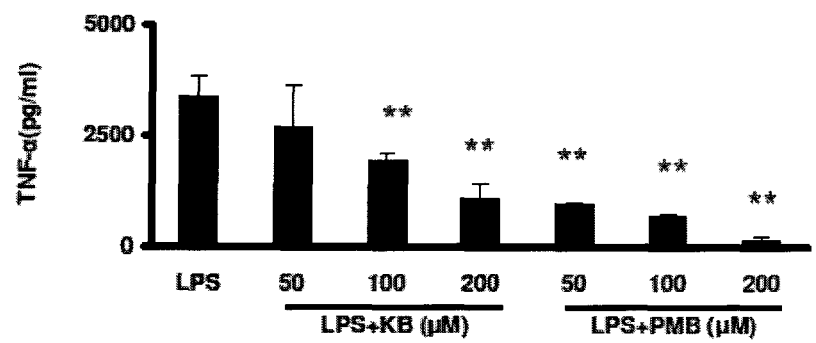
FIGS. 18a, 18b, 18c and 18d show the inhibition of KB and PMB on the release of TNF-α and IL-6 in murine peritoneal macrophages induced by LPS and CpG DNA (CPG).
Figure 18B:
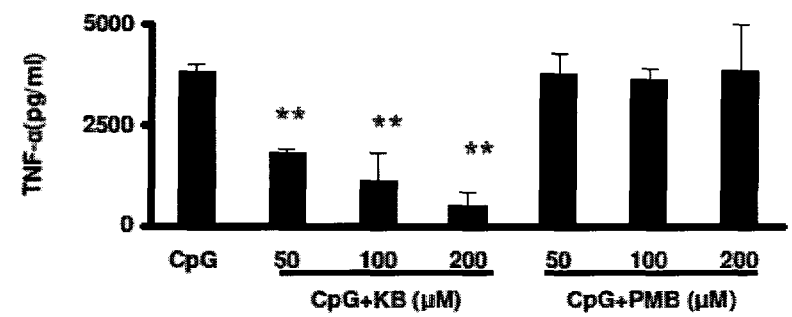
Figure 18C:
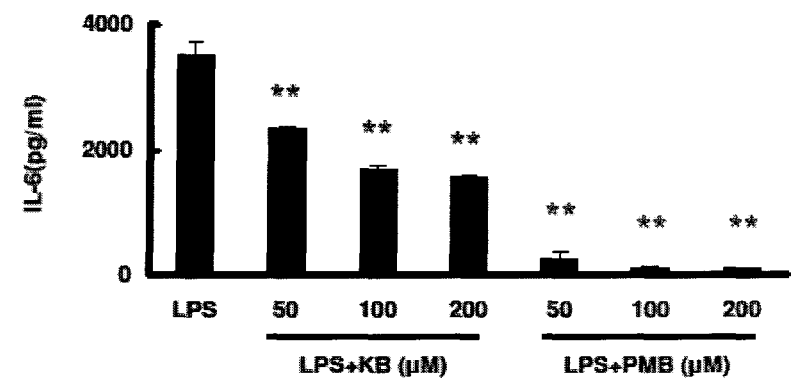
Figure 18D:
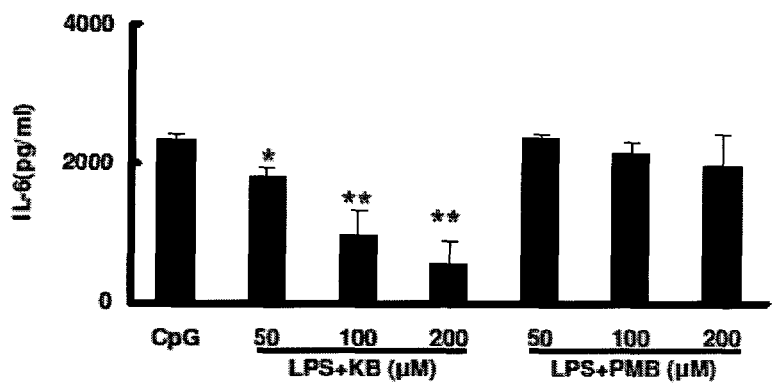

14.2 Result: Observed results were in basic agreement with observations in RAW264.7 cells. KB can inhibit the release of TNF-α and IL-6 induced by both LPS and CpG DNA, and PMB can only inhibit the release of TNF-α and IL-6 induced by LPS. The results were shown in FIG. 18. Wherein FIG. 18a shows the inhibition of KB and PMB on the release of TNF-α in murine peritoneal macrophages stimulated by LPS; FIG. 18b shows the inhibition of KB and PMB on the release of TNF-α in murine peritoneal macrophages stimulated by CpG DNA; FIG. 18c shows the inhibition of KB and PMB on the release of IL-6 in murine peritoneal macrophages stimulated by LPS; and FIG. 18d shows the inhibition of KB and PMB on the release of IL-6 in murine peritoneal macrophages stimulated by CpG DNA.

Embodiments 15: Influence of KB on the mRNA Expressions of TNF-α, IL-6, iNOS and COX-2 in RAW264.7 Cells Stimulated by LPS and CpG DNA 15.1 Methods:
Cells preparation: Cells suspension was adjusted to $1 \times 10^6$/ml in DMEM supplemented with 10% (v/v) NCS; 2 ml of the above suspension was added into 6-well plates and cultured at 37° C. in a 5% $CO_2$ humidified incubator for 2 h; for the purpose of experiment four groups were established: medium group, KB control group, stimulation group and KB treatment group; no reagent was added in medium group; KB control group was added with KB (200 μM); stimulation group was added with LPS (100 ng/ml) and CpG DNA (10 μg/ml); KB treatment group was added with KB (concentrations of 100 and 200 μM) in the meantime of adding LPS and CpG DNA; cells were cultured for 4 h and collected.

RNA extraction: Supernatant was sucked and discarded; 1 ml tripure was added into each well and resuspended with a pipet to make cells completely lysed; the lysate was transferred into 1.5 ml EP tube and incubated at room temperature for 5 min to ensure completed separation of ribonucleoprotein complex; 0.2 ml chloroform was added into EP tube; tube cap was closed and mixed by inversion for 15 sec; EP tube was incubated at room temperature for 10 min until layering of the liquid in tube, then centrifuged at 12000 g at 4_for 15 min; solution was separated into the three-phase; the upper solution (colorless liquid, approximately 0.4 ml) in EP tube was transferred into a new EP tube (DEPC treated); 0.5 ml isopropyl alcohol was added into EP tubes and the liquid was mixed by inversion for several times; EP tube was incubated at room temperature for 10 min to promote RNA precipitating, and centrifuged at 12000 g at 4_for 10 min; the supernatant was discarded; RNA precipitate was added with 1 ml 75% ethanol, vortex washed, and centrifuged at 12000 g at 4 for 10 min; then the supernatant was discarded; EP tube was dried at room temperature for 15 min to remove excessive ethanol; RNA precipitate was diluted with 20 μl ddH2O treated with DEPC, resuspended by pipetting in and out several times, incubated at 55 to 60 for 10 min, and then stored at −70.

Reverse transcription: Reverse-transcription reaction mixture (include: Rnase-free $H_2O$, 10 μl; 5×RT buffer, 4 μl; dNTP mixture, 2 μl; RNase inhibitor, 1 μl; Oligo(dT)20, 1 μl; RNA, 1 μl; ReverTra Ace, 1 μl) was prepared on ice bath, mixed, incubated at 42° C. for 1 h and at 99° C. for 5 min, stored at −20.

PCR amplification: Primers were designed using Primer Premier 5 software by ourselves, and synthesized by Shanghai Sangon Biological Engineering Technology & Services Co., Ltd. The relevant primer sequences are as follows

| | Sequences |
|---|---|
| Mouse TNF-α | Upstream primer: 5-CAGGTTCTGTCCCTTTCACTCACT-3<br>Downstream primer: 5-GTTCAGTAGACAGAAGAGCGTGGT-3 |
| Mouse IL-6 | Upstream primer: 5'-TGGAGTACCATAGCTACCTGGAGT-3'<br>Downstream primer: 5'-TCCT-TAGCCACTCCTTCTGTGACT-3' |
| Mouse iNOS | Upstream primer: 5'-TCCTACACCACACCAAAC-3'<br>Downstream primer: 5'-CTCCAATCTCTGCCTATCC-3' |
| Mouse COX-2 | Upstream primer: 5'-TAGCAGATGACTGCCCAACT-3'<br>Downstream primer: 5'-CACCTCTCCACCAATGACCT-3' |
| Mouse β-actin | Upstream primer: 5'-GGGAAATCGTGCGTGACATCAAAG-3'<br>Downstream primer: 5'-CATACCCAAGAAGGAAGGCTGGAA-3' |

Reaction mixture, which includes 1.5 μl cDNA, 10.0 μl 2×SYBR Green Master Mix 0.5 μl upstream primer (10 μM), 0.5 μl downstream primer (10 μM) and 7.5 μl RNase-free $H_2O$, was added into 0.2 ml PCR tube.

Amplification programs are as follows:

| Step | Temperatures | Time | Velocity | Cycles |
|---|---|---|---|---|
| Initial denaturation | 95° | 60 sec | | 1 |
| PCR (Polymerase Chain Reaction) | 95° | 30 sec | | 40 |
| | 58° | 30 sec | | |
| | 72° | 60 sec | | |
| Melting Curve Assay | 95° | 60 sec | | 1 |
| | 54° | 60 sec | | 1 |
| | 55° | 10 sec | 0.05_/sec | 80 |

Results were expressed as CT value, and converted into ratio of β-actin, the internal reference items, according to $2^{-\Delta\Delta CT}$ methods. Result was expressed by means of mean±standard deviation.

Figure 19A:
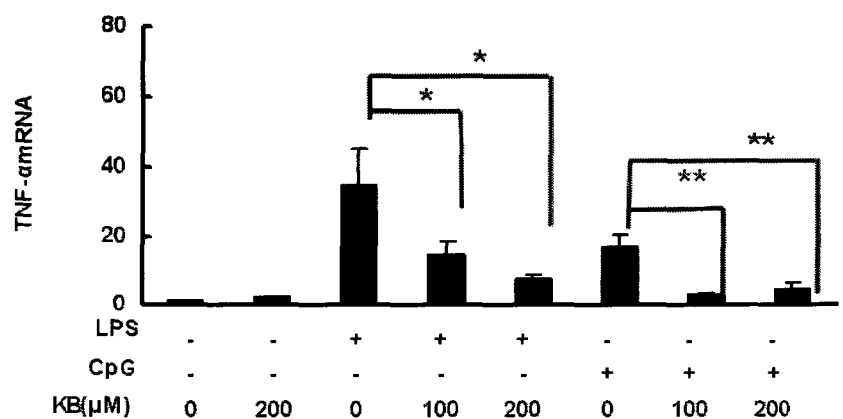
FIGS. 19a, 19b, 19c and 19d show the influence of KB on the mRNA expressions of TNF-α, IL-6, iNOS and COX-2 in RAW264.7 cells stimulated by LPS and CpG DNA (CPG).
Figure 19B:
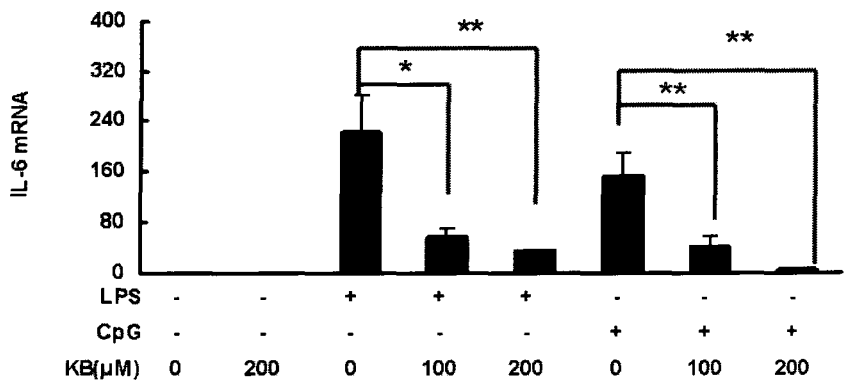
Figure 19C:
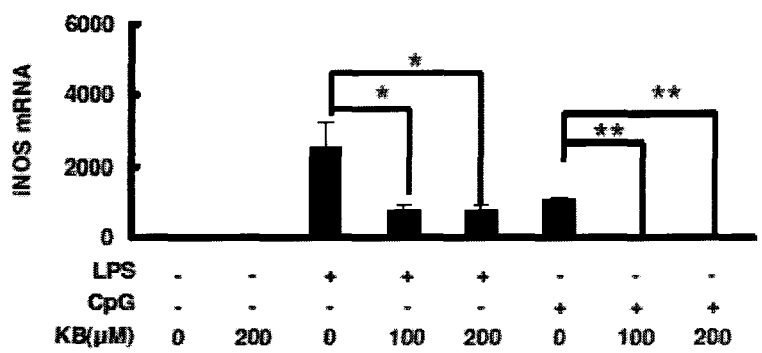
Figure 19D:
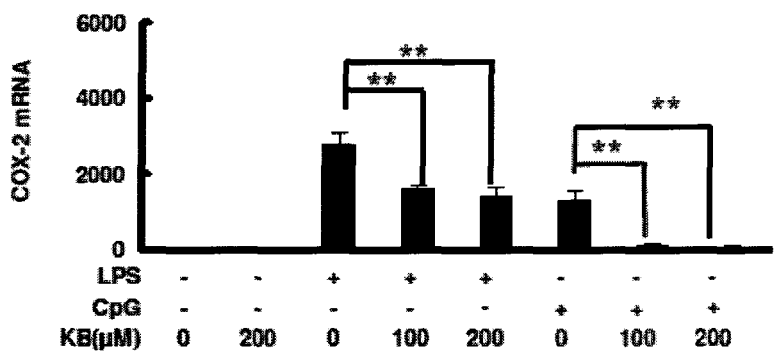

15.2 Results: When murine RAW264.7 cells are not stimulated by LPS or CpG DNA, mRNA expressions of TNF-α, IL-6, iNOS and COX-2 are at low levels; LPS (100 ng/ml) or CpG DNA (10 μg/ml) can significantly up-regulated the expression of above inflammatory mediators in RAW 264.7 cells; KB (100, 200 μM) can significantly inhibit the mRNA expressions of TNF-α, IL-6, iNOS and COX-2 up-regulated by LPS and CpG DNA, and present a dose-dependent relationship with them. The results were shown in FIG. 19. Wherein FIG. 19a shows the inhibition of KB on the mRNA expression of TNF-α in RAW264.7 cells stimulated by LPS and CpG DNA; FIG. 19b shows the inhibition of KB on the mRNA expression of IL-6 in RAW264.7 cells stimulated by LPS and CpG DNA; FIG. 19c shows the inhibition of KB on the mRNA expression of iNOS in RAW264.7 cells stimulated by LPS and CpG DNA; and FIG. 19d shows the inhibition of KB on the mRNA expression of COX-2 in RAW264.7 cells stimulated by LPS and CpG DNA.

Embodiment 16: Influence of KB on the mRNA Expression of TNF-α and IL-6 in Murine Peritoneal Macrophages Stimulated by LPS and CpG DNA 16.1 Methods: Influence of KB on the mRNA expression of TNF-α and IL-6 in murine peritoneal macrophages stimulated by LPS and CpG DNA was observed. Methods were the same as embodiment 15.

Figure 20A:
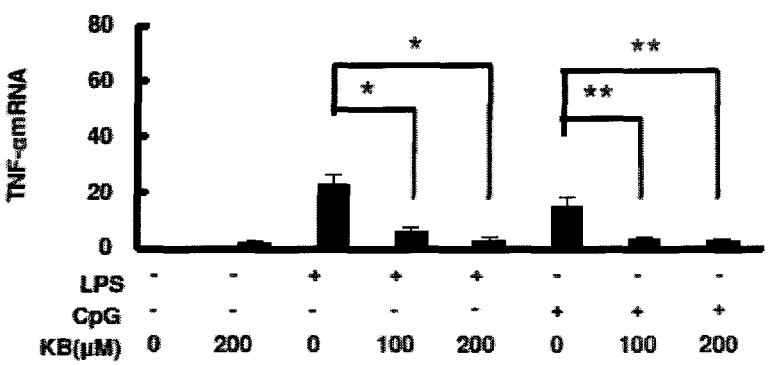
FIGS. 20a and 20b show the influence of KB on the mRNA expression of TNF-α and IL-6 in murine peritoneal macrophages stimulated by LPS and CpG DNA (CPG).
Figure 20B:
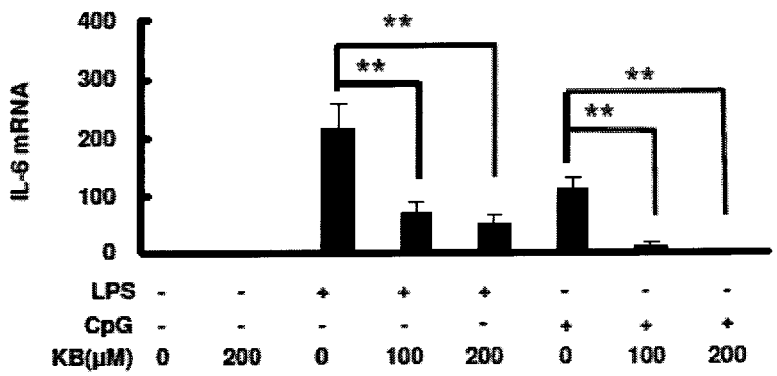

16.2 Results: Observed results were in basic agreement with observations in RAW264.7 cells. KB (100, 200 μM) can significantly inhibit the mRNA expressions of TNF-α and IL-6 up-regulated by LPS and CpG DNA, and present a dose-dependent relationship with them. The results were shown in FIG. 20. Wherein FIG. 20a shows the inhibition of KB on the mRNA expression of TNF-α in murine peritoneal macrophages stimulated by LPS and CpG DNA, and FIG. 20b shows the inhibition of KB on the mRNA expression of IL-6 in murine peritoneal macrophages stimulated by LPS and CpG DNA.

Embodiment 17: Observation of Time and Dose Dependent Effects of KB on TNF-α Release in RAW264.7 Cells Induced by LPS and CpG DNA 17.1 Methods: RAW264.7 cells was diluted to 1×10⁶/ml in DMEM supplemented with 10% (v/v) NCS, transferred into 96-well plates (200 μl per well) and cultured at 37° C. in a 5% CO2 humidified incubator for 4 h.

(1) Observation of dose-dependent effects: For the purpose of experiment a medium group and a KB treatment group were established; each group included three repeated wells; medium group was added with no reagent; KB treatment group was added with KB (final concentrations of 12.5, 25, 50, 100 and 200 μM) in each well, and subsequently added with LPS (final concentration of 100 ng/ml) or CpG DNA (final concentration of 10 μg/ml); cells were cultured at 37° C. in a 5% $CO_2$ humidified incubator for 12 h; the supernatant was collected for further detection; operations were performed according to the manufacturer's instructions of ELISA kit, and the result was expressed by means of mean±standard deviation.

(2) Observation of time-dependent effects: For the purpose of experiment a medium group, a stimulation group and a KB treatment group were established; each group contained three repeated wells; medium group was added with no reagent; stimulation group was added with LPS and CpG DNA; KB treatment group was added with LPS and CpG DNA, in the meantime added with KB (final concentration of 200 μM); cells continued to be cultured at 37° C. in a 5% $CO_2$ humidified incubator; the supernatant at time point of 0, 2, 4, 8, 12 and 24 h after stimulation was separately collected for further detection; detection of TNF-α concentration was performed according to the manufacturer's instructions of ELISA kit, and the result was expressed by means of mean±standard deviation.

Figure 21A:
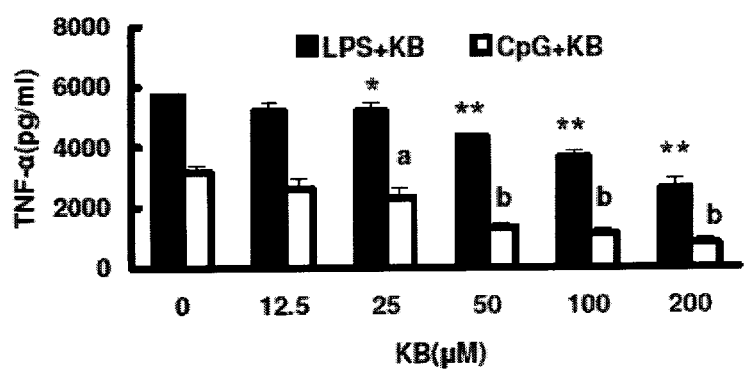
FIGS. 21a, 21b, and 21c show time and dose dependent effects of KB on TNF-α release in RAW264.7 cells induced by LPS and CpG DNA (CPG).

17.2 Results: (1) Observation of dose-dependent effects: After RAW264.7 cells were given with LPS (100 ng/ml) and CpG DNA (10 μg/ml), the release of TNF-α significantly increased, reaching 5710.85±98.03 μg/ml and 3126.39±237.67 μg/ml respectively. After KB treatment, the release of TNF-α in RAW264.7 cells was inhibited by varying degrees; Wherein at the KB concentration of 12.5 μM, the difference of RAW264.7 cells activation between KB treatment group and LPS group or CpG DNA group has no statistic significance (p>0.05); at the KB concentration of 25 μM and above, the inhibitory activity of KB on TNF-α release in RAW264.7 cells induced by LPS and CpG DNA significantly increased (p<0.05 or p<0.01). The inhibition of KB on TNF-α release in RAW264.7 cells induced by CpG DNA showed a dose-dependent relationship. The results were shown in FIG. 21a.

Figure 21B:
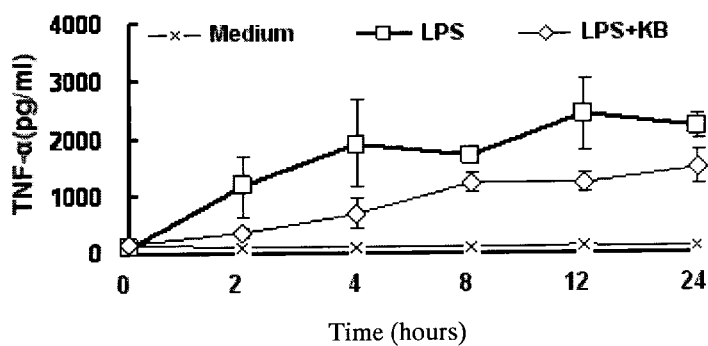
Figure 21C:
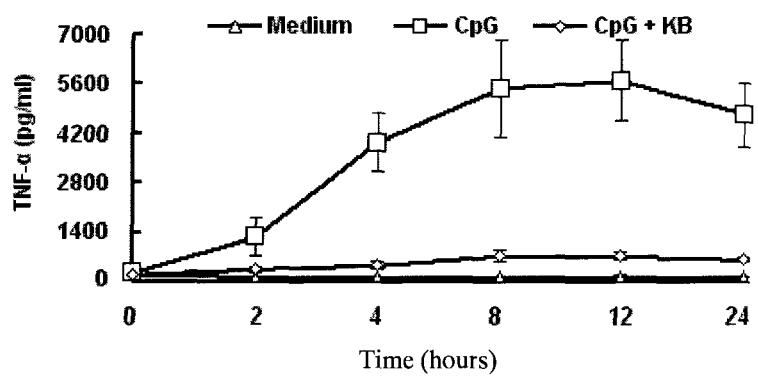

(2) Observation of time-dependent effects: When RAW264.7 cells were not given with any treatment, only basal levels of TNF-α were detected at time point of 0, 2, 4, 8, 12 and 24 h, and there were no significant difference of TNF-α level between various time points. After stimulation by LPS (100 ng/ml) alone, TNF-α levels in supernatant began to increase rapidly at the 2-h time point, and became steady after 4-h time point. If cells were given with 200 μM KB at the meantime, TNF-α levels at various time points were all decreased. After stimulation by CpG DNA (10 μg/ml) alone, the time duration of TNF-α levels increasing in supernatant was basically consistent with LPS group, and TNF-α levels peaked at 12-h time point. If cells were given with 200 μM KB at the meantime, increased TNF-α levels induced by CpG DNA at various time points were all decreased. The antagonism of KB to CpG DNA was stronger than antagonism to LPS. The results were shown in FIG. 21b and FIG. 21c. Wherein FIG. 21b shows the time-dependent effects of inhibition of KB on TNF-α release in RAW264.7 cells induced by LPS, and FIG. 21c shows the time-dependent effects of inhibition of KB on TNF-α release in RAW264.7 cells induced by CpG DNA.

Embodiment 18: Influence of Different Loading Patterns on Inhibition of KB on TNF-α Release in RAW264.7 Cells Induced by LPS and CpG DNA 18.1 Methods: RAW264.7 cells were diluted to 1×10⁶/ml in DMEM supplemented with 10% (v/v) NCS, transferred into 96-well plates (200 μl per well) and cultured at 37° C. in a 5% CO2 humidified incubator for 4 h.

(1) KB was loaded after preincubation with LPS or CpG DNA: KB was diluted in DMEM supplemented with 10% (v/v) NCS to make 400 μM solution; 500 μl of the above KB solution or PBS were mixed with equal volume of LPS (200 ng/ml) or CpG DNA (20 μg/ml) respectively, and incubated at 37 for 20 min and 40 min; RAW264.7 cells culture medium in the 96-well plate was replaced with the above solutions respectively, and continued to be cultured for 12 h; then the supernatant was collected; the concentration of TNF-α was detected according to the manufacturer's instructions of ELISA kit; result was expressed by means of mean±standard deviation.

(2) KB was loaded at various time points: The time point of adding LPS (200 ng/ml) or CpG DNA (20 μg/ml) was 0-min time point; KB (200 μM) was separately added at 40 min and 20 min before the 0-min time point, and 0, 20, 40, 60 and 120 min after the 0-h time point; cells continued to be cultured for 12 h; then the supernatant was collected; the concentration of TNF-α was detected according to the manufacturer's instructions of ELISA kit; result was expressed by means of mean±standard deviation.

(3) Cells stimulation under serum-free conditions: RAW 264.7 culture medium was replaced with serum-free DMEM; KB (50, 100 and 200 μM) and LPS (100 ng/ml) or CpG DNA (10 μg/ml) were added at the meantime; cells were continued to be cultured for 12 h; then the supernatant was collected; the concentration of TNF-α was detected according to the manufacturer's instructions of ELISA kit; result was expressed by means of mean±standard deviation.

Figure 22A:
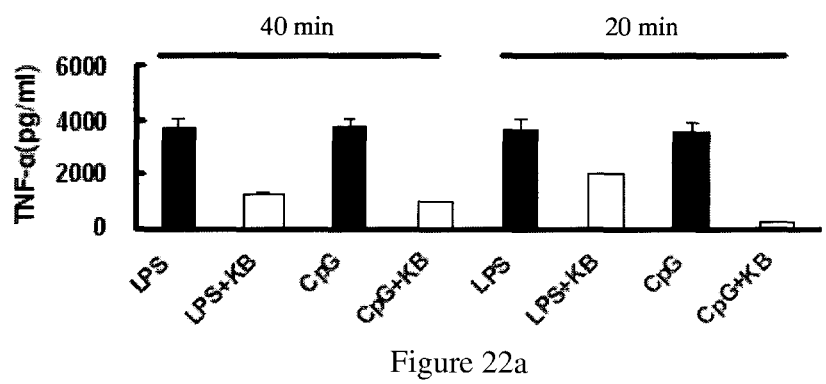
FIGS. 22a, 22b, and 22c show the influence of different loading patterns on inhibition of KB on TNF-α release in RAW264.7 cells induced by LPS and CpG DNA (CPG).
Figure 22B:
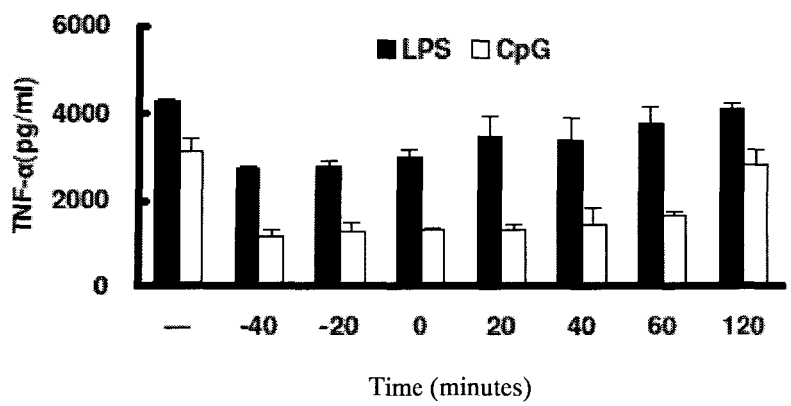
Figure 22C:
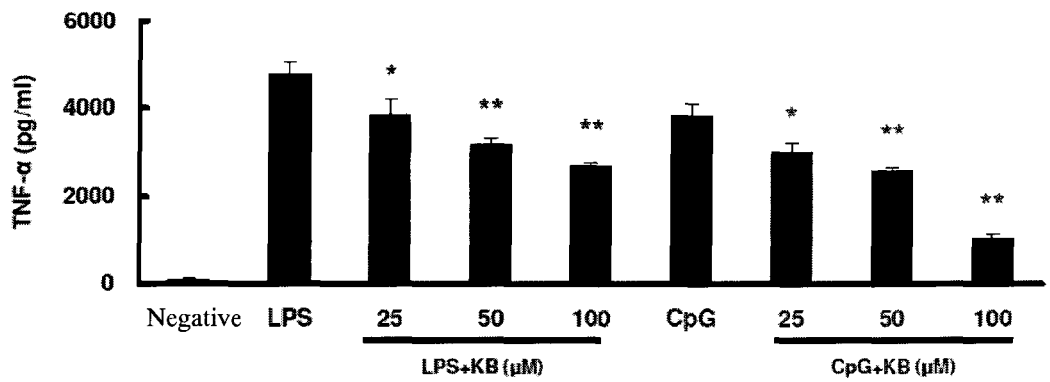

18.2: Results: When LPS or CpG DNA was loaded after preincubation with PBS or KB for 20 min or 40 min, the inhibition of KB on TNF-α release induced by LPS and CpG DNA was significantly enhanced. And then, when the time point of adding LPS (200 ng/ml) or CpG DNA (20 μg/ml) was 0-min time point, and KB (200 μM) was separately added at 40 min and 20 min before the 0-min time point, and 0, 20, 40, 60 and 120 min after the 0-h time point, the results show that, there was no significant difference between the group in which KB was added before the stimulations of LPS and CpG DNA and the group in which KB was added at the mean time of the stimulations of LPS and CpG DNA; when KB was added at 60 min after stimulation, there are still inhibition on TNF-α release induced by LPS and CpG DNA; when KB was added more than 120 min after stimulation, it would no longer have inhibitory activity on TNF-α release. In addition, under serum-free conditions, KB can still inhibit the release of TNF-α in RAW264.7 cells induced by LPS and CpG DNA in a dose-dependant manner, which eliminated the possibility that KB play an indirect role in inhibition on LPS and CpG DNA by acting on the serum protein. The results were shown in FIG. 22. Wherein FIG. 22*a* shows the inhibition of KB on TNF-α release in RAW264.7 cells induced by LPS and CpG DNA, in which KB was loaded after preincubation with LPS or CpG DNA; FIG. 22*b* shows the inhibition of KB on TNF-α release in RAW264.7 cells induced by LPS and CpG DNA, in which KB was loaded at various time points; FIG. 22*c* shows the inhibition of KB on TNF-α release in RAW264.7 cells induced by LPS and CpG DNA, in which KB was loaded without serum.

Embodiment 19: Detection of Inhibitory Activity of KB on Release of TNF-α and IL-6 in RAW264.7 Cells Induced by Various Pathogen-Associated Molecular Patterns 19.1 Methods: RAW264.7 cells were stimulated by six pathogen-associated molecular patterns, LPS (100 ng/ml), CpG DNA (CpG, 10 μg/ml), Pam3CSK4 (Pam3, 10 μg/ml), Poly I:C (I:C, 20 μg/ml), TNF-α (50 ng/ml) and IL-1β (50 ng/ml), and added with KB (final concentration of 200 μM) in the meantime. According to the method in embodiment 6, the supernatant was collected. The concentration of TNF-α was detected according to the manufacturer's instructions of ELISA kit. Result was expressed by means of mean±standard deviation.

Figure 23A:
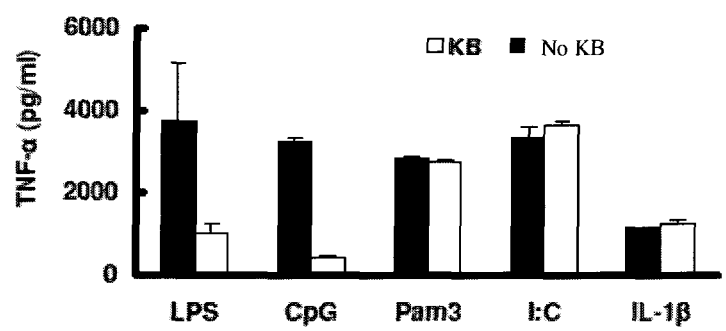
FIGS. 23a and 23b show the inhibition of KB on release of TNF-α and IL-6 in RAW264.7 cells induced by various pathogen-associated molecular patterns (LPS, CpG DNA, Pam3CSK4, Poly I:C, TNF-α and IL-1(β).
Figure 23B:
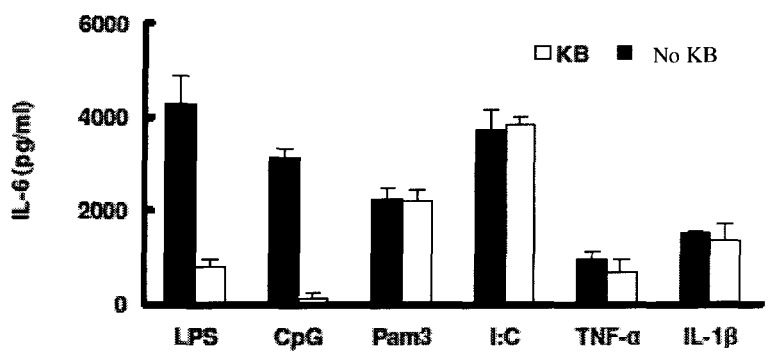

19.2 Results: KB (200 μM) intervention can only inhibit the release of TNF-α and IL-6 induced by LPS and CpG DNA, but has no antagonistic effect on other irritant. The result showed that KB effect only targets at LPS and CpG DNA. The result was shown in FIG. 23. Wherein FIG. 23*a* shows the inhibition of KB on TNF-α release in RAW264.7 cells induced by various pathogen-associated molecular patterns, and FIG. 23*b* shows the inhibition of KB on IL-6 release in RAW264.7 cells induced by various pathogen-associated molecular patterns.

Embodiment 20: Flow Cytometry Detection of KB Influence on the Binding of LPS and CpG DNA (CPG) with RAW264.7 Cells 20.1 Methods: RAW264.7 cells was diluted to $1\times10^6$/ml in DMEM supplemented with 10% (v/v) NCS; 2 ml of the above suspension was added into 24-well cell culture plates and cultured at 37° C. in a 5% CO2 humidified incubator for 4 h; for the purpose of experiment three groups were established: medium group, stimulation group and KB treatment group; no reagent was added into medium group; stimulation group was added with FITC-LPS (200 ng/ml) and 5-FAM-CpG DNA (10 μg/ml); KB treatment group was added with KB (final concentrations of 50, 100 and 200 μM) in the meantime of adding LPS and CpG DNA; cells continued to be cultured for 30 min, washed thrice with PBS, and stored in dark place until the fluorescence intensity of cell membrane surfaces was detected by flow cytometry.

Figure 24A:
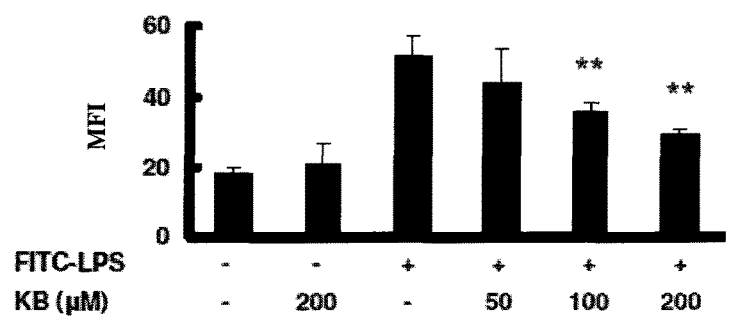
FIGS. 24a and 24b show the detection of KB influence on the binding of LPS and CpG DNA (CPG) with RAW264.7 cells using flow cytometry.
Figure 24B:
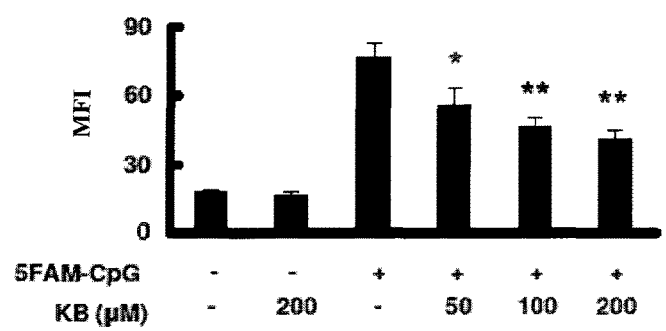

20.2 Result: With untreated RAW264.7 cells served as a negative control, the curve moved toward right after cells were treated with FITC-LPS and 5-FAM-CpG DNA; by plotting according to mean fluorescence intensity (MFI) of cell membrane, MFI was significantly increased after cell were treated with FITC-LPS and 5-FAM-CpG DNA, which suggested that LPS and CpG DNA had been binded with cell membrane receptor; while FITC-LPS and 5-FAM-CpG DNA was added, intervention by various concentration of KB can decrease the MFI of cell membrane in a dose-dependent manner, and inhibited the right shift of curve, which has statistical significance. The results were shown in FIG. 24. Wherein FIG. 24*a* shows the influence of KB on mean fluorescence intensity of LPS on RAW264.7 cell surface, and FIG. 24*b* shows the influence of KB on mean fluorescence intensity of CpG DNA on RAW264.7 cell surface.

Embodiment 21: Observation of KB Influences on Binding and Cellular Internalization of LPS and CpG DNA (CPG) to RAW264.7 Cells Under a Confocal Microscopy 21.1 Methods: RAW264.7 cells were cultured in 20 mm cell culture dishes for confocal microscopy applications, and diluted to $5\times10^5$/ml in DMEM supplemented with 10% (v/v) NCS; 1 ml of the above suspension was transferred into each cell culture dishes and cultured at 37° C. in a 5% $CO_2$ humidified incubator for 4 h; for the purpose of experiment three groups were established, medium group, stimulation group and KB treatment group; the concentration and loading patterns of each group were consistent with Embodiment 12; the cells were then fixed with 4% paraform for 10 min after 30 min of culture, and washed thrice with PBS; nucleus were stained with DAPI (100 ng·mL$^{-1}$) for 2 min, washed with PBS thrice, mounted with a solution of 50% glycerol and 50% PBS, and stored in dark place until intensity and distribution of fluorescence of LPS and CpG DNA on RAW264.7 cells surface were observed under a confocal microscopy.

Figure 25A:
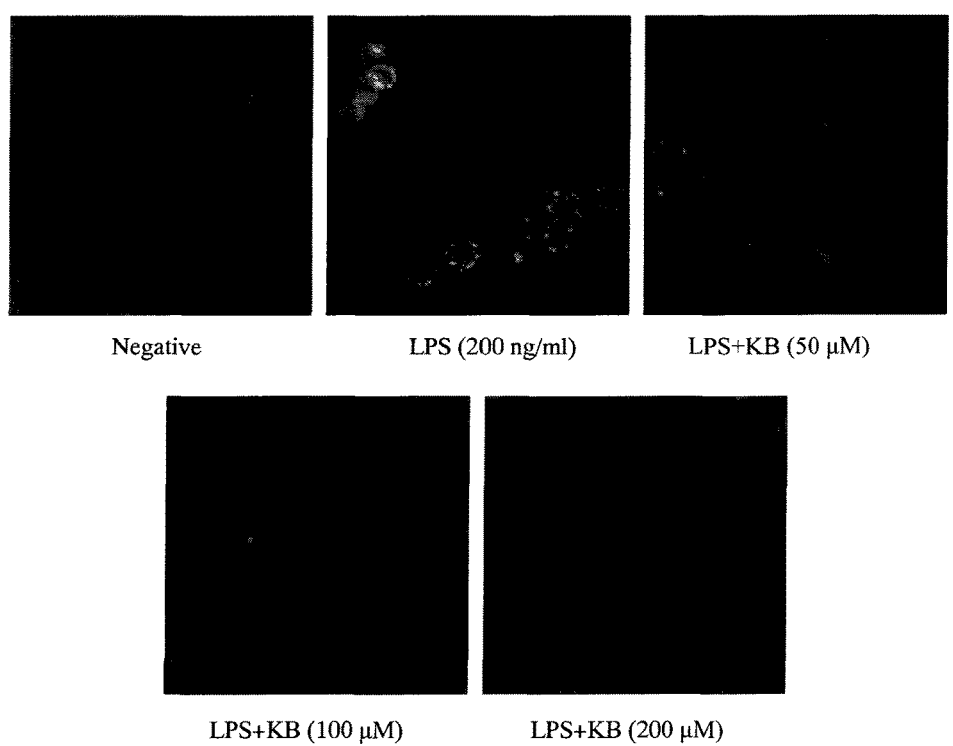
FIGS. 25a and 25b show the observation of KB influences on binding and cellular internalization of LPS and CpG DNA (CPG) to RAW264.7 cells under a confocal microscopy.
Figure 25B:
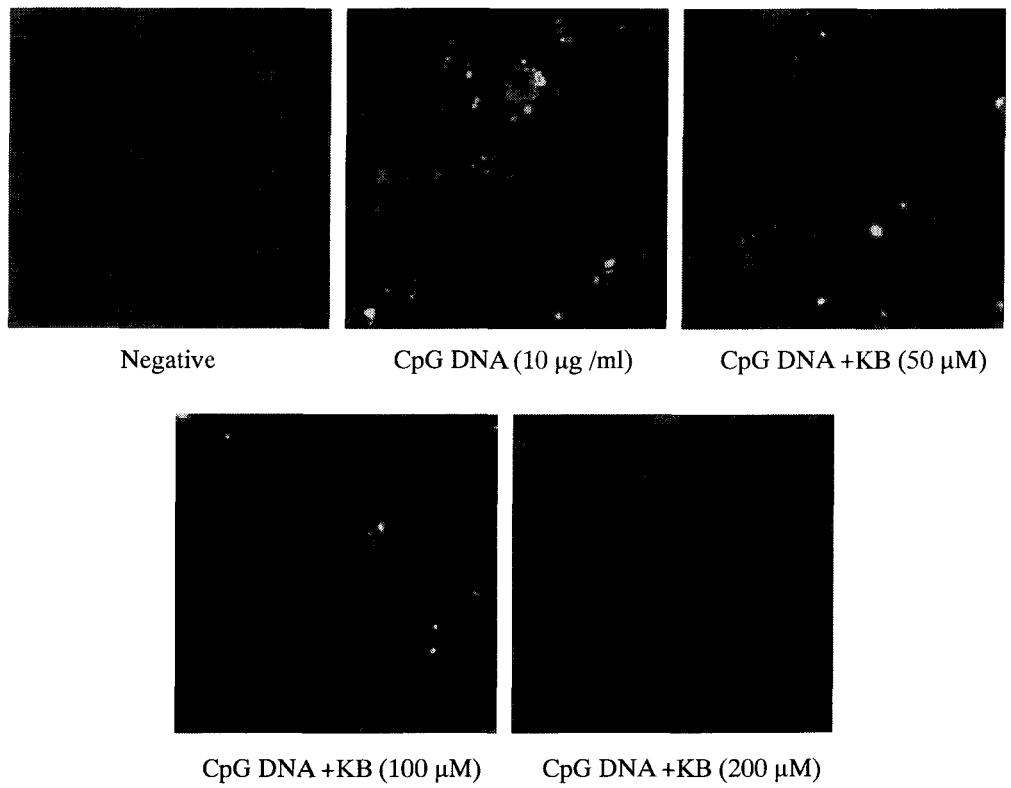

21.2 Results: Green fluorescence of FITC or 5-FAM can not be observed on the untreated RAW264.7 cells surface, and only the blue fluorescence of DAPI stain was observed. After FITC-LPS (200 ng/ml) or 5-FAM-CpG DNA (10 µg/ml) was added, the punctate distribution of fluorescence on the surface of and inside RAW264.7 cells significantly increased, which suggested that LPS or CpG DNA were binded to cell membrane receptor and internalized into the cells. After intervention with 50, 100 and 200 µM KB, the green fluorescence intensity of FITC or 5-FAM on the surface of and inside RAW264.7 cells was significantly weakened, and the inhibitory effect of KB showed obvious dose-dependent. The results were shown in FIG. 25. Wherein FIG. 25a shows the KB influence on binding and cellular internalization of LPS to RAW264.7 cells, and FIG. 25b shows the KB influence on mean fluorescence intensity of 5-FAM-CpG DNA on RAW264.7 cell surface.

Embodiment 22: Assay of KB Inhibition on the Up-Regulated Expression of TLR4 And TLR9 Induced by LPS and CpG DNA 22.1 Methods: The dose of KB, LPS and CpG DNA, specific steps, and the calculation and expression of results in the assay of expression of TLR4 and TLR9 were all consistent with methods of embodiment 15. Wherein the primer sequences of TLR4 and TLR9 are as follows:

|  | Sequences |
| --- | --- |
| Mouse TLR4 | Upstream primer: 5'-AAGGCATGGCATGGCTTACAC-3'<br>Downstream primer: 5'-GGCCAATTTTGTCTCCACAGC-3' |
| Mouse TLR9 | Upstream primer: 5'-TCGCTCAACAAGTACACGC-3'<br>Downstream primer: 5'-GCTCTGCATCATCTGCCTC-3' |
| Mouse β-actin | Upstream primer: 5'-GGGAAATCGTGCGTGACATCAAAG-3'<br>Downstream primer: 5'-CATACCCAAGAAGGAAGGCTGGAA-3' |

Figure 26A:
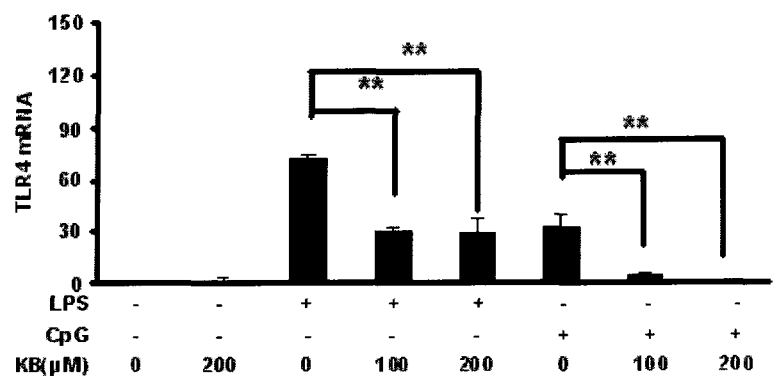
FIGS. 26a and 26b show the inhibition of KB on the up-regulated expression of TLR4 and TLR9 induced by LPS and CpG DNA (CPG).
Figure 26B:
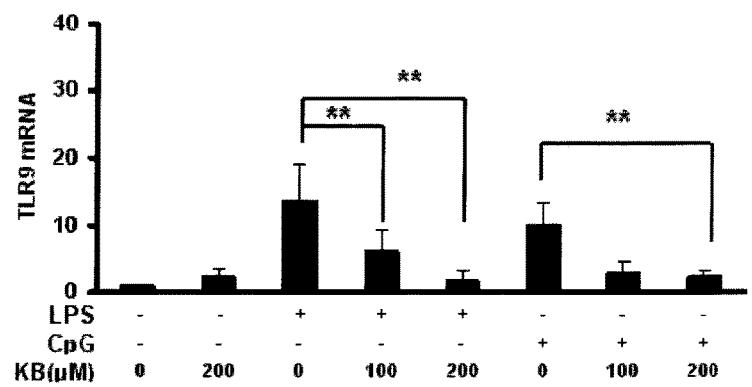

22.2 Result: Results of RT-PCR assay show that with the expressions of TLR4 and TLR9 in untreated RAW264.7 cells serving as a control, stimulation of LPS and CpG DNA can significantly up regulated the expression of TLR4 and TLR9; after intervention with 100 and 200 µM KB, the up-regulated expression of TLR4 and TLR9 was significantly inhibited, which suggested that KB can block the up-regulated expression of TLR4 and TLR9, and then inhibited further stimulation. The results were shown in FIG. 26. Wherein FIG. 26a shows the inhibition of KB on the up-regulated expression of TLR4 mRNA induced by LPS and CpG DNA, and FIG. 26b shows the inhibition of KB on the up-regulated expression of TLR9 mRNA induced by LPS and CpG DNA.

Embodiment 23: Inhibition of KB on Up-Regulated Phosphorylation of Signaling Molecules of IκB-a and p38 in RAW264.7 Cells Stimulated by LPS, CpG DNA, TNF-α and IL-1β

23.1 Methods:

Extraction of cytoplasmic protein: RAW264.7 cells were diluted to 1×10$^6$/ml in DMEM supplemented with 10% (v/v) NCS; 5 ml of the above suspension was transferred into cell culture bottles and cultured at 37° C. in a 5% CO2 humidified incubator for 4 h; a preliminary experiment was first performed, in which RAW264.7 cells were stimulated by LPS (100 ng/ml), CpG DNA (10 µg/ml), TNF-α (50 ng/ml) or IL-1β (50 ng/ml) for 15, 30, 45 and 60 min respectively; for the purpose of formal experiment a medium group, a KB control group, stimulation group (LPS, CpG DNA, TNF-α or IL-1β) and a KB treatment group (LPS+KB group, CpG DNA+KB group, TNF-α+KB group and IL-1β+KB group) were established; no reagent was added in medium group; KB control group was only added with KB (200 µM); stimulation group was added with LPS (100 ng/ml), CpG DNA (10 µg/ml), TNF-α (50 ng/ml) or IL-1β (50 ng/ml); KB treatment group was added with KB (100, 200 µM) in the meantime of adding LPS, CpG DNA, TNF-α or IL-1β; the duration time of cell culture was based on the preliminary experiment (30 min); cells were washed with PBS and centrifuged to collect cells; supernatant was sucked and discarded; the cell pellet was collected for further experiment; each 20 µl cell pellet was added with 200 µl cytoplasm protein extraction reagents supplemented with PMSF, shook vigorously for 5 seconds to completely suspend and disperse the cell pellet, chilled for 10 to 15 min in an ice bath, centrifuged at 12,000 g at 4° C. for 5 min; the supernatant was instantly transferred into a precooled plastic tube, which was the cytoplasmic protein obtained by extraction;

SDS-PAGE Gel Electrophoresis:

(1) Separating gel and stacking gel were prepared as follows:

| 10% separating gel (5.0 ml) | | 5% stacking gel (2.0 ml) | |
| --- | --- | --- | --- |
| Distilled water | 1.3 ml | Distilled water | 1.4 ml |
| 30% Acr-Bis(29:1) | 1.7 ml | 30% Acr-Bis(29:1) | 0.33 ml |
| 1M Tris-HCl(pH 8.8) | 1.9 ml | 1M Tris-HCl (pH 6.8) | 0.25 ml |
| 10% SDS | 0.05 ml | 10% SDS | 0.02 ml |
| 10% AP | 0.05 ml | 10% AP | 0.02 ml |
| TEMED | 0.002 ml | TEMED | 0.002 ml |

Figure 27A:
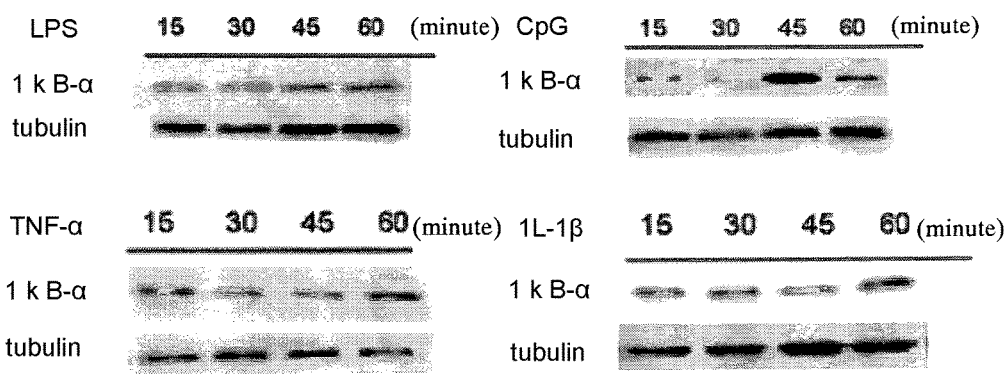
FIGS. 27a and 27b show the inhibition of KB on up-regulated phosphorylation of signaling molecules $I_\kappa B$-α and p38 in RAW264.7 cells stimulated by LPS, CpG DNA (CPG), TNF-α and IL-1β.
Figure 27B:
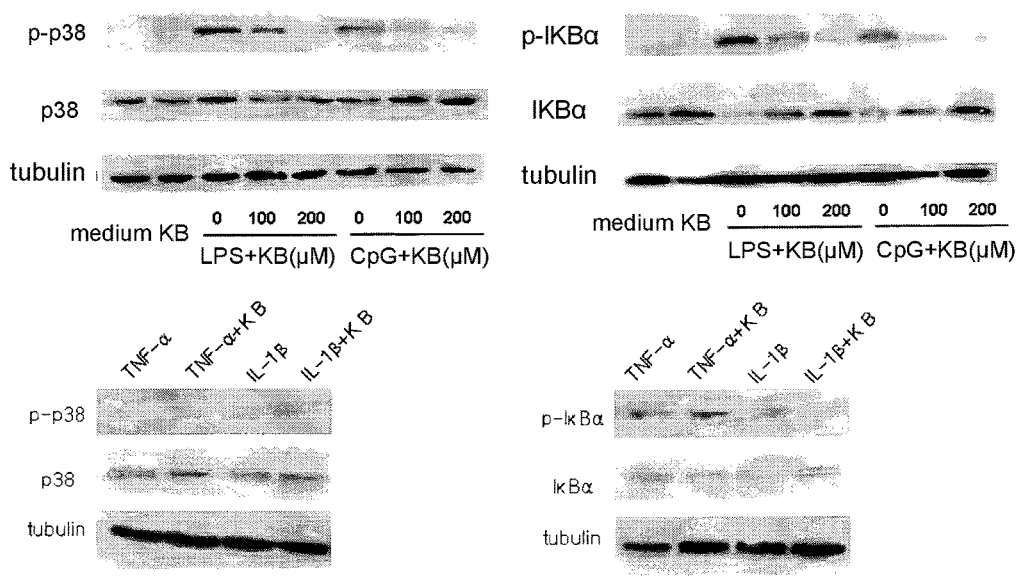

(2) Gel casting: Separating gel was cast to approximately 1.5 cm from the top of the upper panel; after separating gel was cast, dd H$_2$O was added into it until overflow; gel was kept horizontally at room temperature for 30 min; the dd H$_2$O was discarded and blotted up with filter paper after gelling; stacking gel was cast to the top of the upper panel;

a 10-well gel comb was inserted vertically into the gel, and pulled out gently and vertically after 30 min; gel wells were washed twice with dd $H_2O$ to remove remnant gel;

(3) Sample preparation: Protein sample was mixed with 5× concentrated loading buffer in proportion of 4:1, and denatured at 100° C. for 5 min;

(4) Prerunning: Gels were run at 120 V for 5 min with zero-load to remove the foreign substance in gel;

(5) Loading: Sample loading volume was adjusted according to protein concentration to ensure 20 μg protein content of each sample; samples were loaded with microsyringe (5 μl protein molecular weight marker were loaded);

(6) Electrophoresis: Gels were run at 80 V for 30 min (stacking), then 100 V for 60 min (separating), and then terminated when bromophenol blue indicator had reached 1 cm from the bottom of panel;

Membrane transfer: Wet transfer method was adopted, under the conditions of 200 mA, 60 min;

Block and Hybridization:

(1) Membrane was took out from electrophoretic transfer, washed with 0.05% PBST, and blocked at 200 rpm on a horizontal shaker for 1 h;

(2) Primary antibody concentrate was diluted with blocking buffer in proportion of 1:1000; the protein bands were placed on wax-plate; antibody was dropwise added until bands were completely covered, and incubated overnight at 4° C.;

(3) Bands were washed 5 times with PBST on a horizontal shaker at 200 rpm for 5 min each time;

(4) Type of Enzyme labeled secondary antibody were defined according to resource of the primary antibody; secondary antibody was diluted in proportion of 1:5000, added into culture dishes, and incubated at 37 for 30 min;

(5) Bands were washed 5 times with PBST on a horizontal shaker at 200 rpm for 5 min each time;

Identification of chemiluminescence: Equal volume of chemiluminescent substrates A and B were mixed to make working solution, which was dropwise added onto the membrane; the detection was performed by gel documentation systems using chemiluminescence, and the images were collected and saved;

23.2 Results: After LPS and CpG DNA were bound to receptors, intracellular signal transduction pathways were started, and signaling molecules related to inflammatory response were activated. Phosphorylated and total protein of IκB-α and p38 were detected using western blot. The detection results of p38 show that: the expression levels of p38 and tubulin internal reference in each group were basically in agreement; there were hardly any p-p38 expression in medium group and KB control group; p-p38 expression in LPS stimulation group and CpG stimulation DNA group was significantly up regulated; after intervention by KB (100 and 200 μM), p-p38 expression was significantly inhibited. The detection results of IκB-α show that: the expression levels of p38 and tubulin internal reference in each group were basically in agreement; with medium group serving as a control, addition of KB alone had no influence on the expression of IκB-α and p-IκB-α; stimulation of LPS and CpG DNA lead to the degradation of IκB-α (the degradation of IκB-α can not be detected after RAW264.7 cells were stimulated by LPS and CpG DNA for more than 45 min, therefore the stimulation time in formal experiment was chosen as 30 min) and the up-regulated expression of p-IκB-α; after intervention by KB at the same concentration, the degradation of IκB-α and the up-regulated expression of p-IκB-α both were significantly inhibited, which suggested that KB can neutralized LPS and CpG DNA and inhibited the activation of intracellular signaling molecules induced by them. The results were shown in FIG. 27. Wherein FIG. 27*a* shows the degradation of IκB-α in RAW264.7 cells after stimulated by LPS, CpG DNA, TNF-α and IL-1β for different time (15, 30, 45, and 60 mins), and FIG. 27*b* shows the inhibition of KB on up-regulated phosphorylation of signaling molecules p38 induced by LPS, CpG DNA, TNF-α and IL-1β, and the inhibition of KB on degradation and phosphorylation of IκB-α, in RAW264.7 cells.

Embodiment 24: Inhibition of KB on NF-κB Activation in RAW264.7 Cells Induced by LPS and CpG DNA 24.1 Methods:

(1) Extraction of nuclear protein: RAW264.7 cells was adjusted to $1\times10^6$/ml in DMEM supplemented with 10% (v/v) NCS; 5 ml of the above suspension was transferred into cell culture bottles and cultured at 37° C. in a 5% $CO_2$ humidified incubator for 4 h; for the purpose of experiment a medium group, a KB control group, a stimulation group (LPS or CpG DNA) and KB treatment group (LPS+KB group, CpG DNA+KB group) were established; no reagent was added in medium group; KB control group only added with KB (200 μM); stimulation group was added with LPS (100 ng/ml) or CpG DNA (10 μg/ml); KB treatment group was added with KB (100, 200 μM) in the meantime of adding LPS or CpG DNA; cells continued to be cultured for 2 h, then washed with PBS and centrifuged to collect cells; supernatant was sucked and discarded; the cell pellet was collected for further experiment; each 20 μl cell pellet was added with 200 μl cytoplasm protein extraction reagents A supplemented with PMSF, shook vigorously for 5 seconds to completely suspend and disperse the cell pellet, and chilled for 10 to 15 min in an ice bath; the suspension was added with 10 μl cytoplasm protein extraction reagents, shook vigorously for 5 seconds, chilled for 1 min in an ice bath, then shook vigorously for 5 seconds, and centrifuged at 12,000-16,000 g at 4° C. for 5 min; supernatant was sucked and discarded; the cell pellet was added with 50 μl cytoplasm protein extraction reagents supplemented with PMSF, shook vigorously for 20 seconds to completely suspend and disperse the cell pellet, then put in an ice bath, shook vigorously for 20 seconds every 1-2 min for approximately 30 min, and centrifuged at 12,000 g at 4° C. for 10 min; the supernatant was transferred into a precooled EP tube, which was the cytoplasmic protein obtained by extraction, and then stored at −70° C. for further detection;

Detection of NF-κB activation using ELISA: Each well was added with 30 μl binding solution (3.2 μl DTT and 16.2 μl Herring sperm DNA were diluted in 1.6 ml binding solutions); each sample well was added with 20 μl sample (contain 10 μg cytoplasmic protein obtained by extraction); positive control wells was added with 20 μl p50; blank control wells were added with 20 μl dissolution buffer (0.9 μl 1M DTT and 1.8 μl protease inhibitors was diluted in 177.3 μl dissolution buffer AM2); the microtiter plate was shaken for 30 seconds for completely mixing, incubated at room temperature for 1 h, and then washed thrice with 200 μl 1×wash solution (450 μl 10×wash solution were diluted in 4.05 ml dd$H_2O$) and gentle shaking for 5 min each time; each well was added with 100 μl NF-κB antibody (1:1000), incubated for 1 h, then washed thrice with 200 μl 1×wash solution and gentle shaking for 5 min each time; each well was added with 100 μl HRP antibody (1:1000), incubated for 1 h, then washed four times with 200 μl 1×wash solution and gentle shaken for 5 min each time; each well was added with 100 μl detection reagent, incubated for 5 min away from light, and then added with 100 μl stop solution; the absorbance value at 450 nm of each well was detected.

(2) Luciferase reporter gene assay: RAW 264.7 cells were co-transfected with plasmid pGL-luc2P/NF-κBRE and pGL-hRluc according to the manufacturer's instructions of Invitrogen Lipofectamine 2000 reagent. RAW264.7 cells were stimulated by LPS (100 ng/ml) or CpG DNA (10 μg/ml) 48 h after transfection, and intervened by KB (200 μM) simultaneously. After incubation for 6 h, detection was performed according to the manufacturer's instructions of Dual-Glo Luciferase assay kit.

Figure 28A:
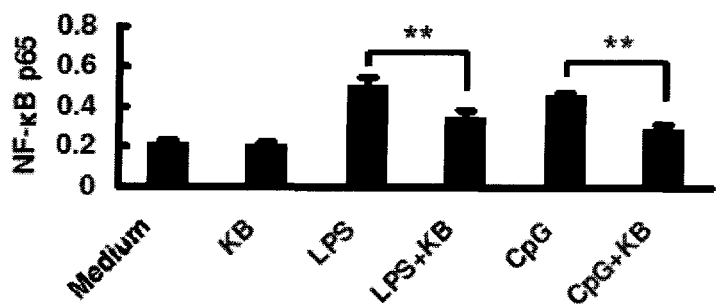
FIGS. 28a and 28b show the inhibition of KB on NF-kB activation in RAW264.7 cells induced by LPS and CpG DNA (CPG).
Figure 28B:
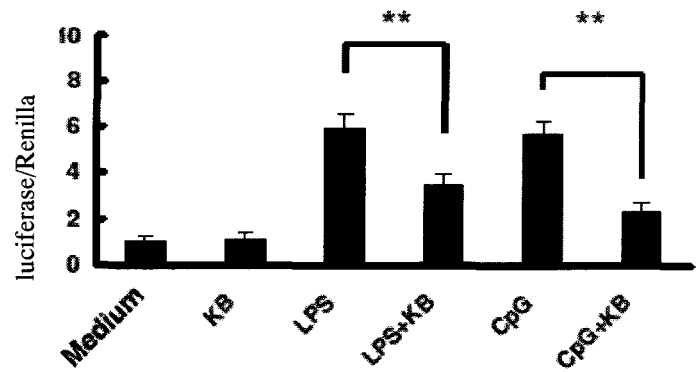

24.2 Result: Transcription factors such as NF-κB were activated by activation of signaling molecules induced by LPS and CpG DNA. P50 and p65, the subunit of NF-κB in nuclear proteins, were detected using ELISA. The results show that: As compared with the unstimulated RAW264.7 cells, KB alone has no influence on the expression of p50 and p65; the stimulation of LPS and CpG DNA can lead to a significant increase of p50 and p65 levels; after intervention of 200 μM KB, the increase of p50 and p65 levels in nuclear proteins was significantly inhibited. Results of luciferase reporter gene assay also show that KB can inhibit NF-κB activation in RAW264.7 cells induced by LPS and CpG DNA. The results were shown in FIG. 28a and FIG. 28b. FIG. 28a shows the inhibition of KB on up-regulation of NF-κB p65 subunit in RAW264.7 cell nucleus induced by LPS and CpG DNA; and FIG. 28b shows assay of KB inhibition on NF-κB activation in RAW264.7 cells induced by LPS and CpG DNA using a luciferase reporter gene assay.

Embodiment 25: Inhibition of KB on Up-Regulated Expression of TLR4, TLR9, MyD88 and NF-κB (p65) in RAW264.7 Cells Stimulated by LPS and CpG DNA 25.1 Methods:

(1) KB inhibition on up-regulated mRNA expression of TLR4, TLR9, MyD88 and NF-κB p65) in RAW264.7 cells stimulated by LPS and CpG DNA (Semi-Quantitative RT-PCR): RAW264.7 cells was adjusted to 1×10⁶/ml in DMEM supplemented with 10% (v/v) NCS; for the purpose of experiment a LPS or CpG DNA stimulation group, a KB treatment group and a medium group were established; LPS or CpG DNA stimulation group was separately added with LPS (100 ng/ml) or CpG DNA (10 μg/ml); KB treatment group was added with KB (200 μM) in the meantime of adding LPS (100 ng/ml) or CpG DNA (10 μg/ml); no reagent was added in medium group; cells continued to be cultured for 4 h after sample loading; total RNA extraction and reverse transcription were performed according to the procedure of embodiment 15; mRNA of TLR4, TLR9 and MyD88 were amplified by PCR; relevant primer sequences are as follows:

| | Sequences |
|---|---|
| Mouse TLR4 | Upstream primer: 5'-AAGGCATGGCATGGCTTACAC-3'<br>Downstream primer: 5'-GGCCAATTTTGTCTCCACAGC-3' |
| Mouse TLR9 | Upstream primer: 5'-TCGCTCAACAAGTACACGC-3'<br>Downstream primer: 5'-GCTCTGCATCATCTGCCTC-3' |
| Mouse MyD88 | Upstream primer: 5'-ACTCGCAGTTTGTTGGATG-3'<br>Downstream primer: 5'-CACCTGTAAAGGCTTCTCG-3' |
| Mouse GAPDH | Upstream primer: 5'-CTGCACCACCAACTGCTTAG-3'<br>Downstream primer: 5'-GTCTGGGATGGAAATTGTGA-3' |

Reaction mixtures were added into 0.2 ml PCR tubes. The reaction mixture included 1 μl cDNA, 10.0 μl 2×Taq Master Mix, 1 μl upstream primer (10 μM), 1 μl downstream primer (10 μM) and 7 μl RNase-free H₂O. PCR programs are as follows:

| Steps | Temperature | Times | Cycles |
|---|---|---|---|
| Initial denaturation | 94° | 3 min | |
| Denaturation | 94° | 30 sec | |
| Annealing | 58° | 30 sec | 26 |
| Extension | 72° | 1 min | |
| Final extension | 72° | 7 min | |
| Preservation | 4° | | |

Finally, the PCR products were detected by agarose gel electrophoresis; 1% agarose gel was prepared and cast; 5 μl PCR products of each tube were loaded, electrophoresed at 100 v for 30 min; then gel was took out and scanned; the images were analysed by Quantity One software.

(2) Inhibition of KB on activation of NF-κB p65 in RAW264.7 cells induced by LPS and CpG DNA: Methods are as above; nucleoprotein extraction continued to be incubated for 1 h after sample loading; then, NF-κB p65 in it was assayed using westernblot; the procedure of nucleoprotein extraction and westernblot were consistent with embodiment 23.

Figure 29A:
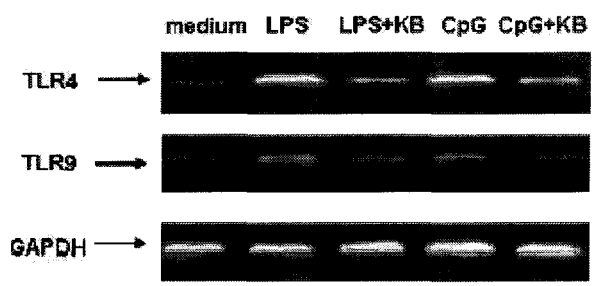
FIGS. 29a, 29b and 29c show KB inhibition on up-regulated expression of TLR4, TLR9 and MyD88, and KB inhibition on activation of NF-kB, in RAW264.7 cells stimulated by LPS and CpG DNA (CPG).
Figure 29B:
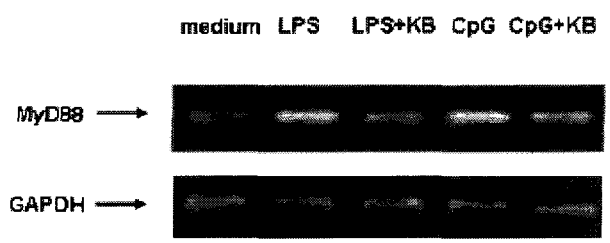
Figure 29C:
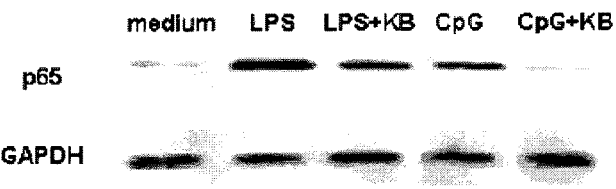

25.2 Results: (1) Assay of semi-quantitative RT-PCR shows that KB (200 μM) can inhibited up-regulated expression of TLR4, TLR9 and MyD88 in RAW264.7 cells stimulated by LPS and CpG DNA. Results were shown in FIGS. 29a and 29b. Wherein FIG. 29a shows the inhibition of KB on up-regulated expression of TLR4 and TLR9 mRNA in RAW264.7 cells induced by LPS and CpG DNA, and FIG. 29b shows the inhibition of KB on up-regulated expression of MyD88 mRNA in RAW264.7 cells induced by LPS and CpG DNA; (2) Results of western blot show that KB (200 μM) can inhibit the up-regulation of NF-κB p65 in RAW264.7 cell nucleus induced by LPS (100 ng/ml) and CpG DNA (10 μg/ml), which suggests that KB can inhibit the activation of NF-κB in RAW264.7 cells induced by stimulation of LPS and CpG DNA. The results were shown in FIG. 29c.

Embodiment 26: Influence of the Combination of KB with LPS or CpG DNA on Vitality of RAW264.7 Cells and Murine Peritoneal Macrophages (MTT Method)

26.1 Methods:

(1) Influence on vitality of RAW264.7 cells: According to embodiment 7, for the purpose of experiment a medium group, KB group (25, 50, 100, 200, 400 and 800 μM), a LPS (100 ng/ml)+KB (0, 100, 200 and 400 μM) group and a CpG DNA (10 μg/ml)+KB (0, 100, 200 and 400 μM) group were established; MTT was dissolved with PBS to make 5 mg/ml solution and filtered, which served as stock solution and stored at −20° C. for further detection; RAW264.7 cells were adjusted to $1\times10^6$/ml in DMEM medium, added into 96-well plates (200 μl per well), and cultured at 37° C. in a 5% $CO_2$ humidified incubator for 4 h; the specified concentration of LPS, CpG DNA and KB were separately loaded according to the grouping; cells were cultured at 37° C. in a 5% $CO_2$ humidified incubator for 24 h, centrifuged at 1000 rpm/min for 5 min; the supernatant was sucked and discarded; each well was added with 180 μl cell culture medium and 20 μl MTT stock solution, then cultured at 37° C. in a 5% $CO_2$ humidified incubator for 4 h, and centrifuged at 1000 rpm/min for 10 min; then the supernatant was sucked and discarded; each well was added with 150 μl DMSO, and shook for 10 min for the dissolution of the crystals; RAW264.7 cells vitality was expressed as absorbance values at 550 nm of each well, which were instantly assayed by ELIASA.

(2) Influence on vitality of murine peritoneal macrophages: Experiment methods are as above. Influences of the combination of KB with LPS or CpG DNA on vitality of murine peritoneal macrophages were assayed.

Figure 30A:
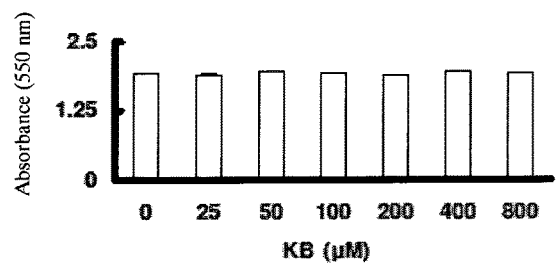
FIGS. 30a, 30b, 30c and 30d show the influence of the combination of KB with LPS or CpG DNA (CPG) on vitality of RAW264.7 cells and murine peritoneal macrophages.
Figure 30B:
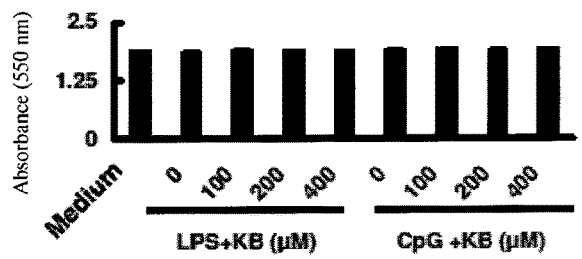
Figure 30C:
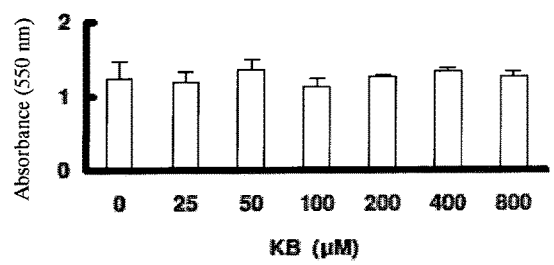
Figure 30D:
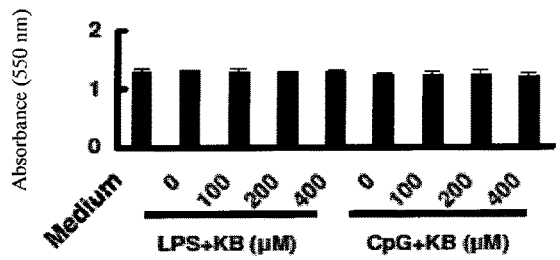

26.2 Result: After RAW264.7 cells were treated with KB or KB plus LPS or CpG DNA, there was no statistic difference on absorbance values between medium group and other groups, which suggests that the inhibition of KB on release of TNF-α and IL-6 in RAW264.7 cells was not caused by its cytotoxicity. The same result was also obtained from observation on the vitality of murine peritoneal macrophages, which suggested that KB antagonism on LPS and CpG DNA in primary cell was not induced by influence on vitality of murine peritoneal macrophages. The results were shown in FIG. 30. Wherein FIG. 30a shows the influence of KB on vitality of RAW264.7 cells; FIG. 30b shows the influence of the combination of KB with LPS or CpG DNA on vitality of RAW264.7 cells; FIG. 30c shows the influence of KB on vitality of murine peritoneal macrophages; and FIG. 30d shows the influence of the combination of KB with LPS or CpG DNA on vitality of murine peritoneal macrophages.

Embodiment 27: Observation of KB Protection (Dose-Dependent Relationship) on Mice Challenged by Lethal Dose of Heat-Killed *Escherichia coli*

27.1 Methods:

(1) Single dose experiment: Experiment 1: A total of 40 Kunming mice (18-20 g), half male and half female, were divided into two groups randomly, heat-killed *E. coli* control group and KB (30 mg/kg) treatment group; each group has 20 mice; after animal weighing, heat-killed *E. coli* group was injected with heat-killed *Escherichia coli* (200 μl per 20 g body weight) and sterile saline (200 μl per 20 g body weight); KB treatment group was injected with KB (200 μl per 20 g body weight) at 5 min after heat-killed *E. coli* was injected; the injection doses of heat-killed *E. coli* were $1.0\times10^{11}$ CFU/kg, and injection doses of KB were 30 mg/kg. After injection, mice in each group were housed separately and feed with sufficient and equivalent food and water. The general status (mental status, appetite, activity and response to stimuli), mortality rate and time of death, of mice in each group, were observed in 7 days after injection.

Experiment 2: KB was diluted to 1.5, 3.0 and 6.0 mg/ml with sterile saline, and heat-killed *E. coli* suspension was diluted to $1.0\times10^{10}$ CFU/ml with sterile saline for further detection; a total of 80 Kunming mice, half male and half female, were randomly divided into heat-killed *E. coli* control group, KB 15 mg/kg treatment group, KB 30 mg/kg treatment group and KB 60 mg/kg treatment group; each group has 16 mice; after animal weighing, heat-killed *E. coli* group was injected with heat-killed *Escherichia coli* (200 μl per 20 g body weight) and sterile saline (200 μl per 20 g body weight); KB treatment groups were injected with KB (200 μl per 20 g body weight) at concentrations of 1.5, 3.0 and 6.0 mg/ml respectively at 5 min after heat-killed *E. coli* injection. After injection, mice in each group were housed separately and feed with sufficient and equivalent food and water. The general status (mental status, appetite, activity and response to stimuli), mortality rate and time of death, of mice in each group, were observed in 7 days after injection.

(2) Multiple dose experiment: KB was diluted to 0.125, 0.25 and 0.5 mg/ml with sterile saline, and heat-killed *E. coli* suspension was diluted same as above. Experiment grouping was the same as above. The KB injection doses were 1.25, 2.5 and 5 mg/kg, and were administrated every 8 h for 3 days. The general status, mortality rate and time of death, of mice in each group, were observed in 7 days after injection.

Figure 31A:
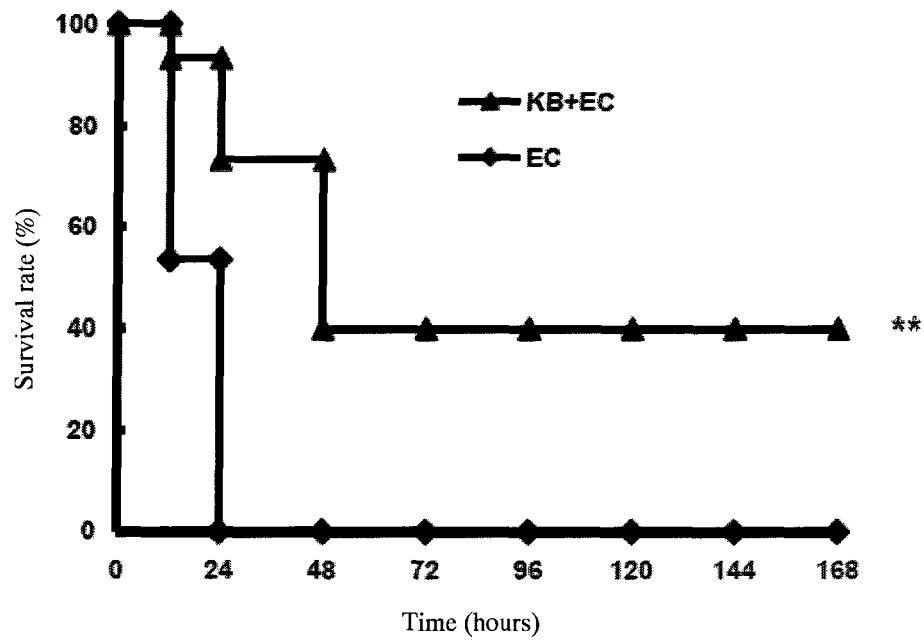
FIGS. 31a, 31b and 31c show the observation of KB protection (dose-dependent relationship) on mice challenged by lethal dose of heat-killed *Escherichia coli*.
Figure 31B:
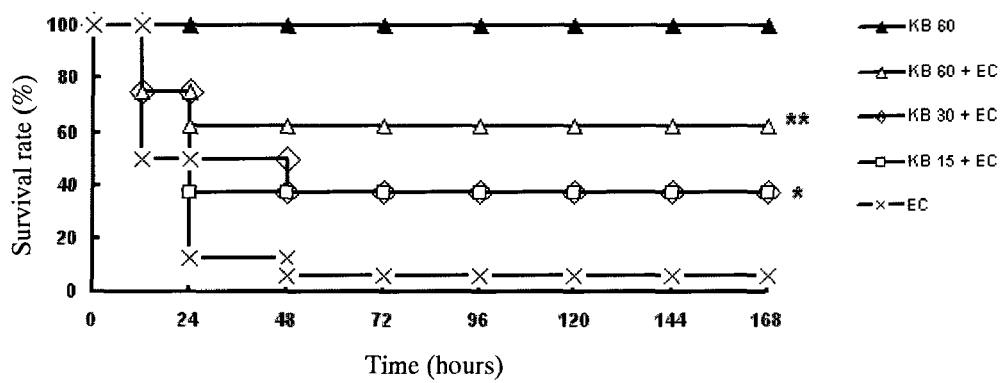
Figure 31C:
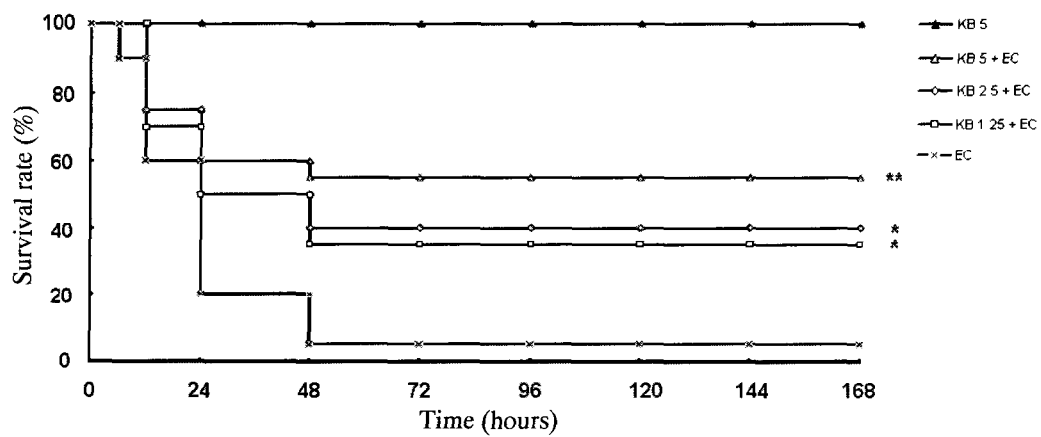

27.2 Result: (1) Single dose experiment: After heat-killed *Escherichia coli* injection, KM mice gathered and shivered, do not drink and eat. The symptoms became worse 6 h after injection. Their reactivity to external stimuli greatly decreased, and body temperature dropped. Death began to occur in severe cases, and peaked at 12-24 h. After 24 h, only a few individual death occurred, and there were no additional deaths after 72 h. The mortality rate in 7 days decreased with the increasing doses of KB. The results were shown in FIGS. 31a and 31b. Wherein FIG. 31a shows the protection of KB (30 mg/kg) on mice challenged by lethal dose of heat-killed *Escherichia coli.*, and FIG. 31b shows the protection of KB (15, 30 and 60 mg/kg) on mice challenged by lethal dose of heat-killed *Escherichia coli.*;

(2) Multiple dose experiment: In multiple dose experiment (administration every 8 h for 3 days), results also show that KB can improve survival rates in model animal. The results were shown in FIG. 31c.

Embodiment 28: Observation on Therapeutic Effect of KB on Mice Challenged by Sublethal Dose of Heat-Killed *Escherichia coli*

28.1 Methods: Kunming mice were randomly divided into two groups, and there were 56 mice in each group; heat-killed *E. coli* was diluted to make $1.0\times10^9$ CFU/ml suspension, and KB was dissolved to 6 mg/ml with sterile saline; caudal vein injection was adopted; medium group was injected with heat-killed *Escherichia coli* (0.2 ml per 20 g body weight) and sterile saline (0.2 ml per 20 g body weight); KB treatment groups were injected with heat-killed *E. coli* suspension S (0.2 ml per 20 g body weight) and KB (0.2 ml per 20 g body weight). Orbital venous blood of mice in medium group and KB treatment group was collected at time point of 0, 4, 8, 12, 24, 48 and 72 h after injection, the specific methods are: mice were killed by cervical dislocation, and immersed in 75% ethanol for skin degerming; the eye of mouse was removed, and blood was collected into a 1.5 ml EP tube; 10 µl blood were added into 190 µl nonpyrogenic water; solution was kept standing for 5-10 min for neutral sedimentation, and centrifuged at 1000 rpm for 10 min; the supernatant was transferred into a new centrifuge tube and stored at −20° C. for further detection; the rest was keep standing until aggregation and serum precipitation, then centrifuged at 3000 rpm for 10 min; the supernatant was transferred into a new centrifuge tube and stored at −20° C. for further detection;

(1) Detection of LPS levels in plasma: 10 µl plasma sample was dissolved in 190 µl sterile saline and mixed. Detection of LPS levels was performed according to the operating procedure of EDS-99 Bacterial Endotoxin Detecting system. Result was expressed by means of mean±standard deviation.

(2) Detection of serum cytokine levels: Because of the small blood volume of mouse, serum was diluted 2 times for detection. Detection of the TNF-α concentration was performed according to the manufacturer's instructions of ELISA kit. Result was expressed by means of mean±standard deviation.

Figure 32A:
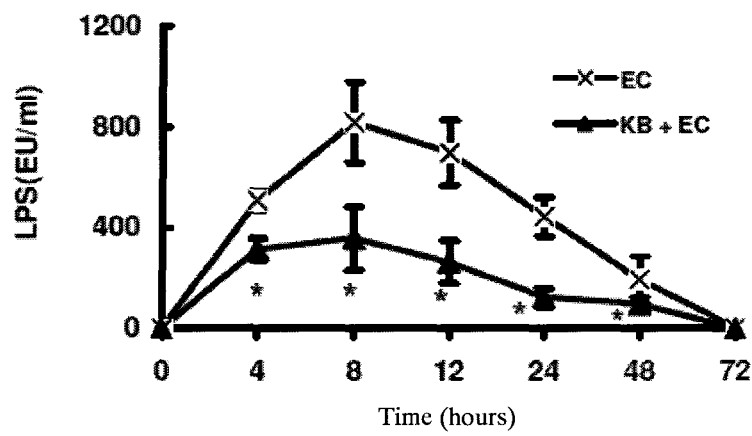
FIGS. 32a and 32b show the therapeutic action of KB to mice challenged by sublethal dose of heat-killed *Escherichia coli*.
Figure 32B:
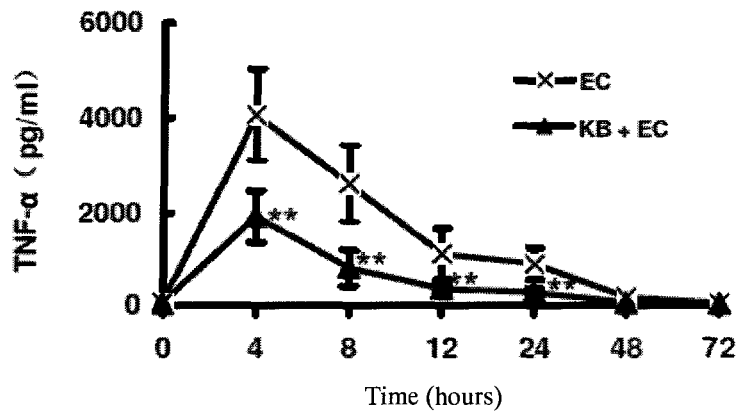

28.2 Result: LPS levels in normal KM mice plasma were below the detection limit (less than 0.0015 EU/ml); after injection of sublethal dose of heat-killed $E.\ coli$ ($1.0 \times 10^{10}$ CFU/ml), LPS levels in KM mice plasma increased rapidly, peaked at 8 h (819.42±159.02 EU/ml), then decreased gradually and close to normal levels at 72 h; the change tendency of LPS levels in mice plasma in KB treatment group were consistent with heat-killed $E.\ coli$ control group in this period, and LPS levels in mice plasma in KB treatment group were significantly lower ($p<0.05$ or $p<0.01$) than heat-killed $E.\ coli$ control group in time point of 4, 8, 12, 24 and 48 h; there were only basic levels of TNF-α exist in normal KM mice serum (less than 100 µg/ml); after injection of sublethal dose of heat-killed $E.\ coli$ ($1.0 \times 10^{10}$ CFU/ml), LPS levels in KM mice serum increased rapidly, peaked at 4 h (4068.40±962.49 µg/ml), then decreased gradually and close to normal levels at 72 h; the change tendency of TNF-α levels in mice serum in KB treatment group were consistent with heat-killed $E.\ coli$ control group in this period, and TNF-α levels in mice serum in KB treatment group were significantly lower ($p<0.01$) than heat-killed $E.\ coli$ control group in time point of 4, 8, 12 and 24 h. The results were shown in FIG. 32. Wherein FIG. 32$a$ shows the influence of KB on LPS levels in plasma of mice challenged by sublethal dose of heat-killed $Escherichia\ coli.$, and FIG. 32$b$ shows the influence of KB on TNF-α levels in serum of mice challenged by sublethal dose of heat-killed $Escherichia\ coli.$ Embodiment 29: Observation of KB Protection (Time-Dependent Relationship) on Mice Challenged by Lethal Dose of Heat-Killed *Escherichia coli*

29.1 Methods: KB was diluted to 6.0 mg/ml with sterile saline, and heat-killed $E.\ coli$ suspension was diluted to $1.0 \times 10^{10}$ CFU/ml with sterile saline for further detection; a total of 96 Kunming mice, half male and half female, were randomly divided into heat-killed $E.\ coli$ control group, 0 h KB treatment group, 2 h KB treatment group, 4 h KB treatment group, 6 h KB treatment group and 8 h KB treatment group; each group has 16 mice; after animal weighing, heat-killed $E.\ coli$ group was injected with heat-killed $Escherichia\ coli$ (200 µl per 20 g body weight) and sterile saline (200 µl per 20 g body weight); KB treatment groups were respectively injected with KB (200 µl per 20 g body weight) at time point of 0, 2, 4, 6 and 8 h after heat-killed $E.\ coli$ injection. After injection, mice in each group were housed separately and feed with sufficient and equivalent food and water. The general status (mental status, appetite, activity and response to stimuli), mortality rate and time of death, of mice in each group, were observed in 7 days after injection.

Figure 33:
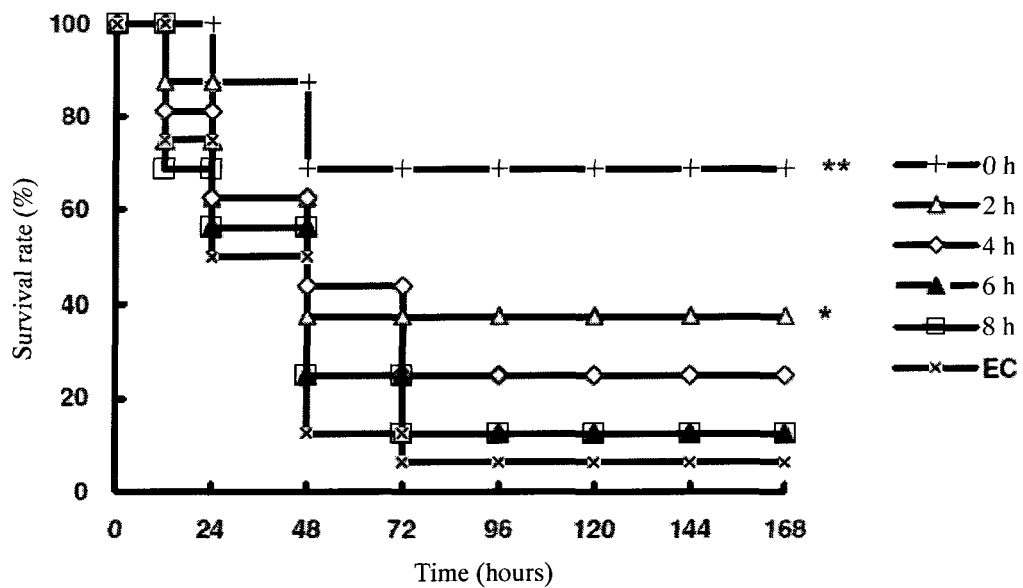
FIG. 33 shows the observation of KB protection (time-dependent relationship) on mice challenged by lethal dose of heat-killed *Escherichia coli.
Figure 34A:
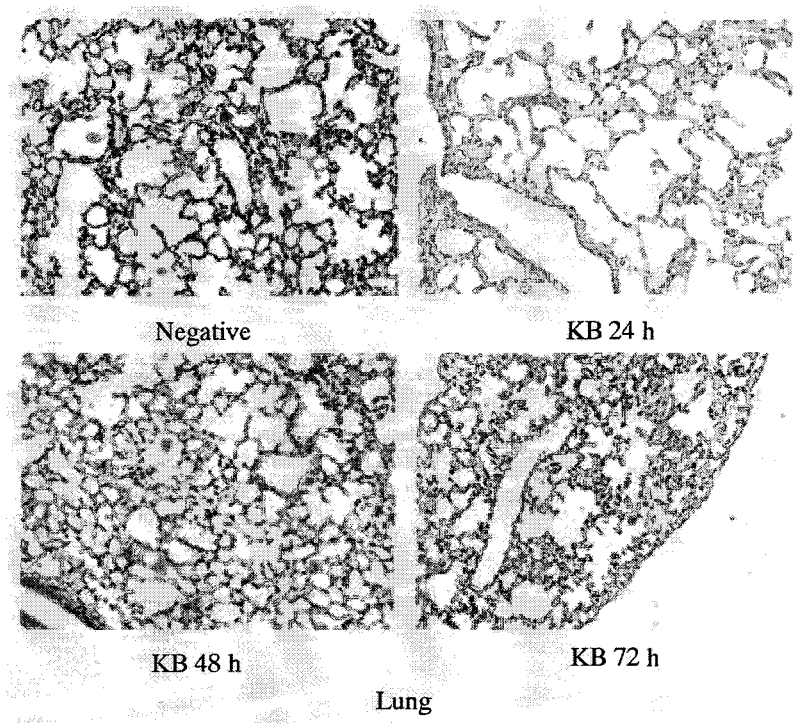
FIGS. 34*a*, 34*b*, 34*c* and 34*d* show the influence of KB on major organ pathological morphous of mice.
Figure 34B:
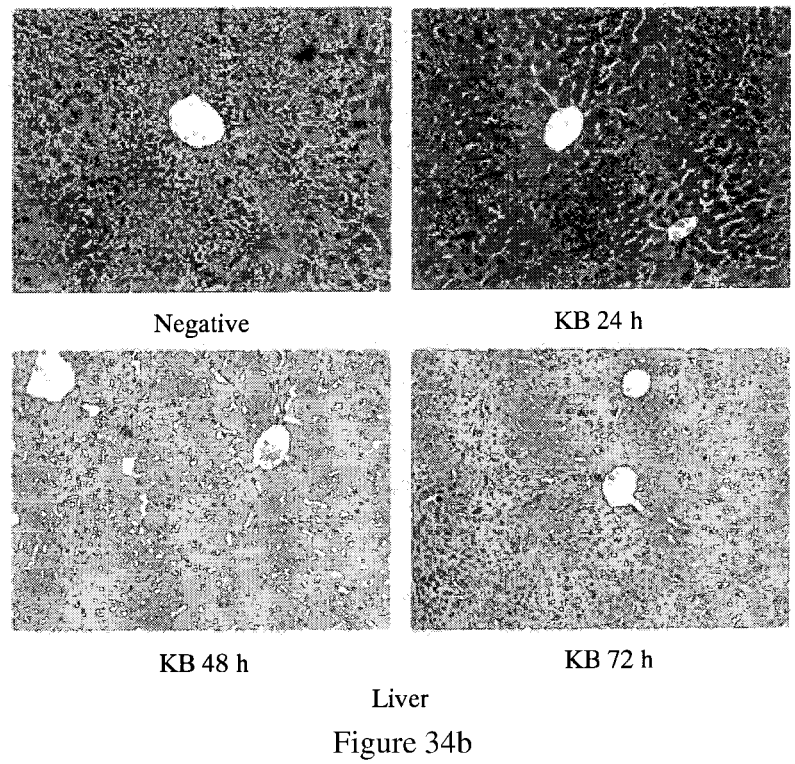
Figure 34C:
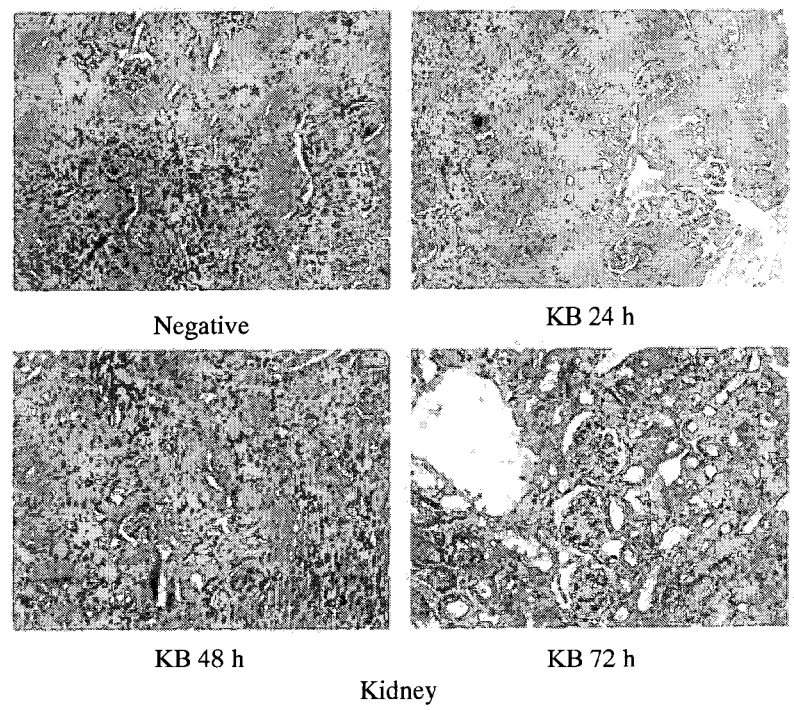
Figure 34D:
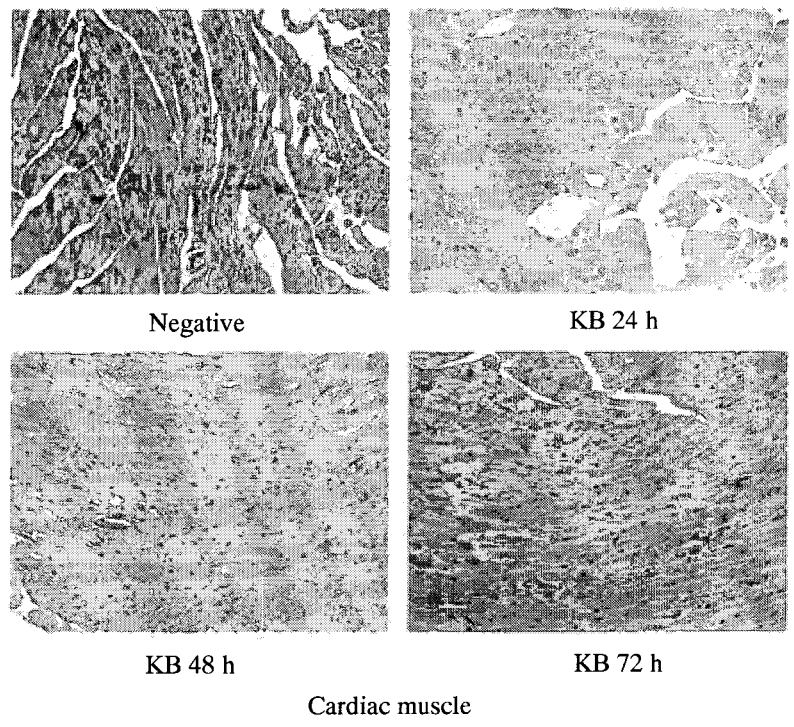

29.2 Results: Intervention by single dose of KB (60 mg/kg) at 2 h after heat-killed $E.\ coli$ injection ($1.0 \times 10^{11}$ CFU/kg) still can increase the survival rate of model animal. But treatment after 2 h (4, 6 and 8 h) no longer has a significant protective effect. The results were shown in FIG. 33.

Embodiment 30: Influence of KB on Major Organ Pathological Morphous of Mice 30.1 Methods: A total of 16 Kunming mice were randomly divided into four groups; each group has 4 mice, half male and half female; for the purpose of experiment a medium group and a KB (60 mg/kg) treatment group were established; mice in medium group were immediately killed by cervical dislocation, and KB treatment group were killed separately killed at 24, 48 and 72 h after injection; the cavitas thoracis and abdominal cavity of mice were cut open; organs such as heart, liver, lung, kidney and intestine were moved out, rinsed with sterile saline, plunged into 10% formaldehyde solution for fixing, dehydrated, embedded in paraffin, HE dyed and mounted; organ histopathological changes were observed under a light microscope.

30.2 Result: As compared with the medium group, in mouse lung of the KB treatment group there were no congestion and inflammatory cell infiltration; in mouse liver of KB the treatment group, liver cell surrounded central veins had a clear structure, and there were no pathological changes such as cellular swelling and necrosis; in mouse kidney of the KB treatment group, glomeruli and bowman's capsule in each time point had normal morphology and no obvious changes; in mouse cardiac muscle of the KB treatment group, myocardial cells arranged in clear rules and there were no cell necrosis and inflammatory cell infiltration; the above results show that morphous of heart, lung, liver and kidney in mice of the KB treatment group in each time point (24, 48 and 72 h) had no obvious changes under light microscope, which suggests that there were no significant changes in major organs of mice after single dose injection of KB (60 mg/kg). The results were shown in FIG. 34. Wherein FIG. 34$a$ shows the lung morphology of mice after KB injection; FIG. 34$b$ shows the liver morphology of mice after KB injection; FIG. 34$c$ shows the kidney morphology of mice after KB injection; FIG. 34$d$ shows the cardiac muscle morphology of mice after KB injection.

What is claimed is:

1. A method of treating sepsis in a subject in need thereof comprising:
   administering to the subject a therapeutically effective amount of Kukoamine B.

2. The method according to claim 1, wherein the therapeutically effective amount of Kukoamine B antagonizes bacterial endotoxin/lipopolysaccharide (LPS) and unmethylated DNA (CpG DNA) of bacteria.

3. The method according to claim 1, wherein the therapeutically effective amount of Kukoamine B is 1.25 to 60 mg/kg.

4. The method according to claim 1, wherein Kukoamine B is extracted from *Lycii cortex*.

5. The method according to claim 4, wherein the *Lycii cortex* is the dried root bark of *Lycium chinense* Mill. or *Lycium barbarum* L of the Solanaceae family.

\* \* \* \* \*

SEQUENCE LISTING

<160> NUMBER OF SEQ ID NOS: 24

<210> SEQ ID NO 1
<211> LENGTH: 24
<212> TYPE: DNA
<213> ORGANISM: Artificial Sequence
<220> FEATURE:
<223> OTHER INFORMATION: Upstream primer for PCR amplification of mouse
      TNF-a mRNA
<220> FEATURE:
<221> NAME/KEY: primer_bind
<222> LOCATION: (1)..(24)

<400> SEQUENCE: 1
caggttctgt ccctttcact cact                                              24

<210> SEQ ID NO 2
<211> LENGTH: 24
<212> TYPE: DNA
<213> ORGANISM: Artificial Sequence
<220> FEATURE:
<223> OTHER INFORMATION: Downstream primer for PCR amplification of
      mouse TNF-a mRNA
<220> FEATURE:
<221> NAME/KEY: primer_bind
<222> LOCATION: (1)..(24)

<400> SEQUENCE: 2
gttcagtaga cagaagagcg tggt                                              24

<210> SEQ ID NO 3
<211> LENGTH: 24
<212> TYPE: DNA
<213> ORGANISM: Artificial Sequence
<220> FEATURE:
<223> OTHER INFORMATION: Upstream primer for PCR amplification of mouse
      IL-6 mRNA
<220> FEATURE:
<221> NAME/KEY: primer_bind
<222> LOCATION: (1)..(24)

<400> SEQUENCE: 3
tggagtacca tagctacctg gagt                                              24

<210> SEQ ID NO 4
<211> LENGTH: 24
<212> TYPE: DNA
<213> ORGANISM: Artificial Sequence
<220> FEATURE:
<223> OTHER INFORMATION: Downstream primer for PCR amplification of
      mouse IL-6 mRNA
<220> FEATURE:
<221> NAME/KEY: primer_bind
<222> LOCATION: (1)..(24)

<400> SEQUENCE: 4
tccttagcca ctccttctgt gact                                              24

<210> SEQ ID NO 5
<211> LENGTH: 18
<212> TYPE: DNA
<213> ORGANISM: Artificial Sequence
<220> FEATURE:
<223> OTHER INFORMATION: Upstream primer for PCR amplification of mouse
      iNOS mRNA
<220> FEATURE:
<221> NAME/KEY: primer_bind
<222> LOCATION: (1)..(18)

<400> SEQUENCE: 5

```
tcctacacca caccaaac                                                    18

<210> SEQ ID NO 6
<211> LENGTH: 19
<212> TYPE: DNA
<213> ORGANISM: Artificial Sequence
<220> FEATURE:
<223> OTHER INFORMATION: Downstream primer for PCR amplification of
      mouse iNOS mRNA
<220> FEATURE:
<221> NAME/KEY: primer_bind
<222> LOCATION: (1)..(19)

<400> SEQUENCE: 6
ctccaatctc tgcctatcc                                                   19

<210> SEQ ID NO 7
<211> LENGTH: 20
<212> TYPE: DNA
<213> ORGANISM: Artificial Sequence
<220> FEATURE:
<223> OTHER INFORMATION: Upstream primer for PCR amplification of mouse
      COX-2 mRNA
<220> FEATURE:
<221> NAME/KEY: primer_bind
<222> LOCATION: (1)..(20)

<400> SEQUENCE: 7
tagcagatga ctgcccaact                                                  20

<210> SEQ ID NO 8
<211> LENGTH: 20
<212> TYPE: DNA
<213> ORGANISM: Artificial Sequence
<220> FEATURE:
<223> OTHER INFORMATION: Downstream primer for PCR amplification of
      mouse COX-2 mRNA
<220> FEATURE:
<221> NAME/KEY: primer_bind
<222> LOCATION: (1)..(20)

<400> SEQUENCE: 8
cacctctcca ccaatgacct                                                  20

<210> SEQ ID NO 9
<211> LENGTH: 24
<212> TYPE: DNA
<213> ORGANISM: Artificial Sequence
<220> FEATURE:
<223> OTHER INFORMATION: Upstream primer for PCR amplification of
      mouse beta-actin mRNA
<220> FEATURE:
<221> NAME/KEY: primer_bind
<222> LOCATION: (1)..(24)

<400> SEQUENCE: 9
gggaaatcgt gcgtgacatc aaag                                             24

<210> SEQ ID NO 10
<211> LENGTH: 24
<212> TYPE: DNA
<213> ORGANISM: Artificial Sequence
<220> FEATURE:
<223> OTHER INFORMATION: Downstream primer for PCR amplification of
      mouse beta-actin mRNA
<220> FEATURE:
<221> NAME/KEY: primer_bind
<222> LOCATION: (1)..(24)
```

```
<400> SEQUENCE: 10
catacccaag aaggaaggct ggaa                                          24

<210> SEQ ID NO 11
<211> LENGTH: 21
<212> TYPE: DNA
<213> ORGANISM: Artificial Sequence
<220> FEATURE:
<223> OTHER INFORMATION: Upstream primer for PCR amplification of mouse
      TLR4 mRNA
<220> FEATURE:
<221> NAME/KEY: primer_bind
<222> LOCATION: (1)..(21)

<400> SEQUENCE: 11
aaggcatggc atggcttaca c                                             21

<210> SEQ ID NO 12
<211> LENGTH: 21
<212> TYPE: DNA
<213> ORGANISM: Artificial Sequence
<220> FEATURE:
<223> OTHER INFORMATION: Downstream primer for PCR amplification of
      mouse TLR4 mRNA
<220> FEATURE:
<221> NAME/KEY: primer_bind
<222> LOCATION: (1)..(21)

<400> SEQUENCE: 12
ggccaatttt gtctccacag c                                             21

<210> SEQ ID NO 13
<211> LENGTH: 19
<212> TYPE: DNA
<213> ORGANISM: Artificial Sequence
<220> FEATURE:
<223> OTHER INFORMATION: Upstream primer for PCR amplification of mouse
      TLR9 mRNA
<220> FEATURE:
<221> NAME/KEY: primer_bind
<222> LOCATION: (1)..(19)

<400> SEQUENCE: 13
tcgctcaaca agtacacgc                                                19

<210> SEQ ID NO 14
<211> LENGTH: 19
<212> TYPE: DNA
<213> ORGANISM: Artificial Sequence
<220> FEATURE:
<223> OTHER INFORMATION: Downstream primer for PCR amplification of
      mouse TLR9 mRNA
<220> FEATURE:
<221> NAME/KEY: primer_bind
<222> LOCATION: (1)..(19)

<400> SEQUENCE: 14
gctctgcatc atctgcctc                                                19

<210> SEQ ID NO 15
<211> LENGTH: 24
<212> TYPE: DNA
<213> ORGANISM: Artificial Sequence
<220> FEATURE:
<223> OTHER INFORMATION: Upstream primer for PCR amplification of mouse
      beta-actin mRNA
<220> FEATURE:
<221> NAME/KEY: primer_bind
<222> LOCATION: (1)..(24)
```

```
<400> SEQUENCE: 15
gggaaatcgt gcgtgacatc aaag                                          24

<210> SEQ ID NO 16
<211> LENGTH: 24
<212> TYPE: DNA
<213> ORGANISM: Artificial Sequence
<220> FEATURE:
<223> OTHER INFORMATION: Downstream primer for PCR amplification of
      mouse beta-actin mRNA
<220> FEATURE:
<221> NAME/KEY: primer_bind
<222> LOCATION: (1)..(24)

<400> SEQUENCE: 16
catacccaag aaggaaggct ggaa                                          24

<210> SEQ ID NO 17
<211> LENGTH: 21
<212> TYPE: DNA
<213> ORGANISM: Artificial Sequence
<220> FEATURE:
<223> OTHER INFORMATION: Upstream primer for PCR amplification of mouse
      TLR4 mRNA
<220> FEATURE:
<221> NAME/KEY: primer_bind
<222> LOCATION: (1)..(21)

<400> SEQUENCE: 17
aaggcatggc atggcttaca c                                             21

<210> SEQ ID NO 18
<211> LENGTH: 21
<212> TYPE: DNA
<213> ORGANISM: Artificial Sequence
<220> FEATURE:
<223> OTHER INFORMATION: Downstream primer for PCR amplification of
      mouse TLR4 mRNA
<220> FEATURE:
<221> NAME/KEY: primer_bind
<222> LOCATION: (1)..(21)

<400> SEQUENCE: 18
ggccaatttt gtctccacag c                                             21

<210> SEQ ID NO 19
<211> LENGTH: 19
<212> TYPE: DNA
<213> ORGANISM: Artificial Sequence
<220> FEATURE:
<223> OTHER INFORMATION: Upstream primer for PCR amplification of mouse
      TLR9 mRNA
<220> FEATURE:
<221> NAME/KEY: primer_bind
<222> LOCATION: (1)..(19)

<400> SEQUENCE: 19
tcgctcaaca agtacacgc                                                19

<210> SEQ ID NO 20
<211> LENGTH: 19
<212> TYPE: DNA
<213> ORGANISM: Artificial Sequence
<220> FEATURE:
<223> OTHER INFORMATION: Downstream primer for PCR amplification of
      mouse TLR9 mRNA
<220> FEATURE:
<221> NAME/KEY: primer_bind
```

```
<222> LOCATION: (1)..(19)

<400> SEQUENCE: 20
gctctgcatc atctgcctc                                                    19

<210> SEQ ID NO 21
<211> LENGTH: 19
<212> TYPE: DNA
<213> ORGANISM: Artificial Sequence
<220> FEATURE:
<223> OTHER INFORMATION: Upstream primer for PCR amplification of mouse
      MyD88 mRNA
<220> FEATURE:
<221> NAME/KEY: primer_bind
<222> LOCATION: (1)..(19)

<400> SEQUENCE: 21
actcgcagtt tgttggatg                                                    19

<210> SEQ ID NO 22
<211> LENGTH: 19
<212> TYPE: DNA
<213> ORGANISM: Artificial Sequence
<220> FEATURE:
<223> OTHER INFORMATION: Downstream primer for PCR amplification of
      mouse MyD88 mRNA
<220> FEATURE:
<221> NAME/KEY: primer_bind
<222> LOCATION: (1)..(19)

<400> SEQUENCE: 22
cacctgtaaa ggcttctcg                                                    19

<210> SEQ ID NO 23
<211> LENGTH: 20
<212> TYPE: DNA
<213> ORGANISM: Artificial Sequence
<220> FEATURE:
<223> OTHER INFORMATION: Upstream primer for PCR amplification of mouse
      GAPDH mRNA
<220> FEATURE:
<221> NAME/KEY: primer_bind
<222> LOCATION: (1)..(20)

<400> SEQUENCE: 23
ctgcaccacc aactgcttag                                                   20

<210> SEQ ID NO 24
<211> LENGTH: 20
<212> TYPE: DNA
<213> ORGANISM: Artificial Sequence
<220> FEATURE:
<223> OTHER INFORMATION: Downstream primer for PCR amplification of
      mouse GAPDH mRNA
<220> FEATURE:
<221> NAME/KEY: primer_bind
<222> LOCATION: (1)..(20)

<400> SEQUENCE: 24
gtctgggatg gaaattgtga                                                   20
```